(12) United States Patent
Morris et al.

(10) Patent No.: US 7,329,744 B2
(45) Date of Patent: Feb. 12, 2008

(54) FUSION GENES ASSOCIATED WITH ACUTE MEGAKARYOBLASTOC LEUKEMIAS

(75) Inventors: Stephan W. Morris, Memphis, TN (US); Zhigui Ma, Memphis, TN (US); Johann K. Hitzler, Toronto (CA)

(73) Assignees: St. Jude Children's Research Hospital Inc., Memphis, TN (US); The Hospital for Sick Children (CA)

( * ) Notice: Subject to any disclaimer, the term of this patent is extended or adjusted under 35 U.S.C. 154(b) by 443 days.

(21) Appl. No.: 10/475,917

(22) PCT Filed: Apr. 23, 2002

(86) PCT No.: PCT/US02/12797

§ 371 (c)(1),
(2), (4) Date: Jun. 4, 2004

(87) PCT Pub. No.: WO02/088309

PCT Pub. Date: Nov. 7, 2002

(65) Prior Publication Data

US 2004/0203011 A1    Oct. 14, 2004

Related U.S. Application Data

(60) Provisional application No. 60/286,910, filed on Apr. 27, 2001.

(51) Int. Cl.
C07H 21/04    (2006.01)

(52) U.S. Cl. .................. 536/23.4; 536/23.1; 536/24.31; 530/350

(58) Field of Classification Search ............... 536/23.4, 536/23.1, 24.31; 530/350
See application file for complete search history.

(56) References Cited

U.S. PATENT DOCUMENTS 5,529,925 A    6/1996    Morris et al.
5,770,421 A    6/1998    Morris et al.
6,174,674 B1    1/2001    Morris et al.

OTHER PUBLICATIONS

Bernstein, J et al., "Nineteen cases of the t(1;22)(p13;q13) acute megakaryoblasic leukaemia of infants/children and a review of 39 cases: report from a t(1;22) study group," *Leukemia*, 2000, pp. 216-218, vol. 14.

Kirsch, I et al., "A systematic, high-resolution linkage of the cytogenetic and physical maps of the human genome," *Nature Genetics*, Apr. 2000, pp. 339-340, vol. 24.

Nagase, T et al., "Prediction of the Coding Sequences of Unidentified Human Genes. XVI. The Complete Sequences of 150 New cDNA Clones from Brain Which Code for large Proteinsin vitro," *DNA Research*, 2000, pp. 65-73, vol. 7.

Mercher, T. et al., "Involvement of a human gene related to the Drosophila spen gene in the recurrent t(1;22) translocation of acute megakaryocutic leukemia," *PNAS*, May 8, 2001, pp. 5776-5779, vol. 98(10).

Li, Y. et al., "Fusion of two novel genes, RBM15 and MKL1, in the t(1;22)(p13;q13) of acute megakaryoblastic leukemia," *Nature Genetics*, Jul. 2001, pp. 220-221, vol. 28.

GenBank Database Report for Accession No. AB037859, May 10, 2002.

GenBank Database Report for Accession No. Q96T37, Jun. 26, 2007.

GenBank Database Report for Accession No. Q969V6, Jun. 26, 2007.

GenBank Database Report for Accession No. AAB95111, Jan. 6, 1998.

GenBank Database Report for Accession No. AF368061, Sep. 7, 2001.

GenBank Database Report for Accession No. Q96FE8, Nov. 28, 2006.

GenBank Database Report for Accession No. AC005915, Nov. 3, 1998.

GenBank Database Report for Accession No. AAF47681, Apr. 26, 2007.

GenBank Database Report for Accession No. AF145664, Jun. 14, 1999.

*Primary Examiner*—Larry R. Helms
*Assistant Examiner*—Minh-Tam Davis
(74) *Attorney, Agent, or Firm*—Alston & Bird LLP

(57) ABSTRACT

The invention relates to human nucleotide sequences which occur as a result of the t(1;22)(p13;q13) chromosomal translocation event which is known to occur almost invariable in young children with acute megakaryoblastic leukemia. The translocation results in the formation of fusion genes which encode fusion proteins. The invention provides the nucleotide sequences of transcripts of the fusion genes and the amino acid sequences of the fusion proteins encoded thereby. Also provided are methods for detecting the t(1, 22) translocation, for identifying agents capable of binding to the fusion protein and for identifying agents useful for treating patients with acute megakaryoblastic leukemia.

1 Claim, 1 Drawing Sheet

FUSION GENES ASSOCIATED WITH ACUTE MEGAKARYOBLASTOC LEUKEMIAS

FEDERALLY SPONSORED RESEARCH OR DEVELOPMENT

This invention was made in part with U.S. Government support under Cancer Center Support (CORE) grants CA-21765 and CA-87064 from the National Cancer Institute. The Government may have certain rights in this invention.

FIELD OF THE INVENTION

The present invention is directed to the field of the molecular genetics of cancer. Specifically, the present invention relates to human acute megakaryoblastic leukemias in which a translocation between chromosomes 1 and 22 (referred to in the art as "t(1;22)") has occurred. On a molecular level, the DNA rearrangement in t(1;22) results in two reciprocal fusion genes that each comprise segments of the RBM15 and MKL1 genes.

BACKGROUND OF THE INVENTION

Chromosomal abnormalities are frequently associated with malignant diseases. In a number of instances, specific chromosomal translocations have been characterized, which generate fusion genes encoding proteins with oncogenic properties (Sawyers et al., Cell 64:337-350 (1991)).

Recently, the cloning of chromosomal translocations has led to identification of pathogenically relevant oncogenic fusion transcripts and proteins in specific subsets of acute nonlymphocytic leukemia (ANLL), such as promyelocytic leukemia-retinoic acid receptor alpha fusion gene (PML-RARα) in acute promyelocytic leukemia (FAB-M3 subtype), the acute myeloid leukemia 1-eight twenty one fusion gene (AML1-ETO) in ANLL with maturation (FAB-M2), and various mixed lineage leukemia (MLL) fusions in acute myelomonocytic and monocytic leukemias (FAB-M4 and -M5) (Melnick, A. & Licht, J. D., Blood 93, 3167-3215 (1999); Downing, J. R., Br. J Haematol. 106, 296-308 (1999); Rowley, J. D., Semin. Hematol. 36, 59-72 (1999); Look, A. T., Science 278, 1059-1064 (1997); Faretta, M., Di Croce, L. & Pelicci, P. G., Sem. Hematol. 38, 42-53 (2001)). Despite these significant advances, little is known about the genetic mechanisms underlying acute leukemias of the megakaryoblastic (platelet precursor) lineage (AMKL, FAB-M7) (Cripe, L. D, infra). Almost invariably, AMKL in non-Down syndrome infants and young children harbor the t(1;22)(p13;q13) translocation, in most cases as the sole cytogenetic abnormality (Carroll, A. et al; Lion, T. et al., and Bernstein, J. et al., infra). Phenotypically, AMKL presents de novo (i.e., without a so-called preleukemic stage), with a large leukemia cell mass, and frequent fibrosis of bone marrow and other organs. Progression is usually rapid despite therapy, with a median overall patient survival of only eight months. Thus, compositions and methods for the early and accurate diagnosis and treatment of leukemia, particularly AMKL, are needed.

SUMMARY OF THE INVENTION

Compositions and methods associated with the diagnosis and treatment of leukemia are provided. The invention discloses the identification, cloning and sequencing of human nucleotide sequences corresponding to the t(1;22) (p13;q13) chromosomal translocation event which occurs in individuals with acute megakaryoblastic leukemia (AMKL). The rearrangement recombines sequences from the RNA-binding motifprotein-15 gene (RBM15) on chromosome 1p13 with those from the Megakaryoblastic Leukemia-1 gene (MKL1) on chromosome 22q13. As a result of the t(1;22)(p13;q13) rearrangement, two fusion genes, one on each of the two derivative chromosomes (der(1) and der (22)), are produced. The first fusion gene, designated RBM15-MKL1, resides on der(22) and comprises a 5' portion of the RBM15 and a 3' segment of the MKL1. The second fusion gene, designated as MKL1-RBM15, resides on der(1) and comprises a 5' portion of the MKL1 and a 3' segment of the RBM15. Both fusion genes are transcribed. A single transcript is expressed from RBM15-MKL1. Two transcripts are found to be expressed from MKL1-RBM15. Isolated nucleotide molecules comprising the nucleotide sequences of the RBM15-MKL1 gene transcript and the two MKL1-RBM15 gene transcripts, MKL1-RBM15$_S$ and MKL1-RBM15$_{S+AE}$ are provided. Additionally provided are the amino acid sequences of the fusion proteins encoded by the RBM15-MKL1 transcript and the two MKL1-RBM15 transcripts.

Utilizing the sequences of the present invention, the present invention provides methods of identifying the presence of nucleic acids containing the RBM15-MKL1 fusion gene and/or MKL1-RBM15 fusion gene and the transcripts of these fusion genes in a sample. Such methods can be used in diagnosis and treatment, for example, to determine if particular cells or tissues express RBM15-MKL1 or MKL1-RBM15 coding sequences, or diagnostic assays to determine if a mammal has leukemia or a genetic predisposition to (i.e., is at an increased risk of developing) leukemia.

The RBM15-MKL1 and MKL1-RBM15 fusion proteins and polypeptide sequences of the invention, whether produced by host/vector systems or otherwise, can be used to produce antibodies which specifically recognize (i.e., bind) the RBM15-MKL1 and MKL1-RBM15 fusion proteins, respectively. The invention provides methods of identifying the presence of nucleic acids encoding the RBM15-MKL1 fusion protein and/or MKL1-RBM15 fusion protein in a sample involving the use of such antibodies. Such methods find use in diagnosis and treatment of AMKL, for example, to determine if particular cells or tissues express the RBM15-MKL1 fusion protein and/or the MKL1-RBM15 fusion proteins and to inhibit the activity of these fusion proteins.

The present invention also provides for transgenic cells and animals, preferably mice, which (a) contain and express an RBM15-MKL1 fusion gene derived from an exogenous source and subsequently introduced into the genome of the cell or animal, (b) contain and express a gene encoding an RBM15-MKL1 fusion protein derived from an exogenous source and subsequently introduced into the genome of the cell or animal, (c) contain and express an MKL1-RBM15 fusion gene derived from an exogenous source and subsequently introduced into the genome of the cell or animal (d) contain and express a gene encoding an MKL1-RBM15 fusion protein derived from an exogenous source and subsequently introduced into the genome of the cell or animal, (e) contain and express both a gene encoding an MKL1-RBM15 fusion protein and a gene encoding an RBM15-MKL1 fusion protein, with both genes derived from an exogenous source and subsequently introduced into the genome of the animal, (f) knock-out the expression of the RBM15 and/or MKL1 genes, or (g) knock-out the expression of the RBM15-MKL1 and/or MKL1-RBM15 fusion proteins in an AMKL cell line. Methods of utilizing such cells and mice to identify and test carcinogenic or therapeutic compositions are also described herein.

The nucleotide sequences of the RBM15-MKL1 and MKL1-RBM15 genes and the coding sequences of the RBM15-MKL1 and the two MKL1-RBM15 fusion proteins of the invention can also be utilized to design and prepare agents which specifically inhibit the expression of the RBM15-MKL1 or MKL1-RBM15 genes in cells for therapeutic and other purposes. The RBM15-MKL1 and MKL1-RBM15 nucleotide sequences of the invention can be further utilized in methods of producing the RBM15-MKL1 and MKL1-RBM15 fusion proteins, respectively.

The present invention further provides methods for isolating and identifying the natural ligand(s) and gene targets bound by the RBM15-MKL1 and MKL1-RBM15 fusion proteins, and for identifying derivatives of the ligand(s) or synthetic compounds that act to inhibit the action of the RBM15-MKL1 and MKL1-RBM15 fusion proteins.

Additionally provided are compartmentalized kits to receive in close confinement one or more containers containing the reagents used in one or more of the above described detection methods.

DETAILED DESCRIPTION OF THE INVENTION

Figure 1:
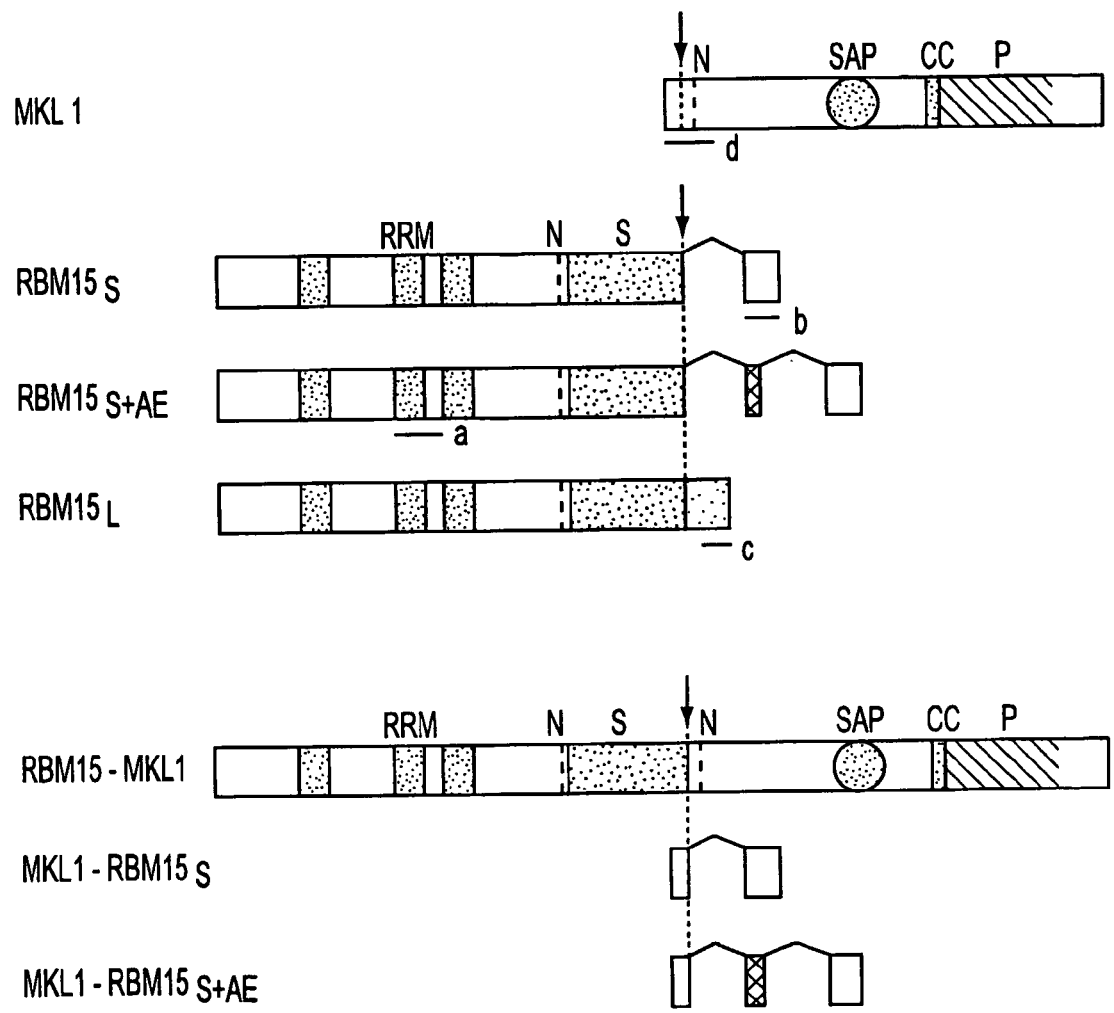
FIG. 1 is a schematic representation of the normal RBM15 and MKL1 proteins, and the fusion proteins formed by t(1;22). The locations of the fusion junctions in the proteins are indicated by vertical arrows. The 931-aa MKL1 protein (predicted mass, 98.9 kDa; SEQ ID. NO: 14) contains a bipartite nuclear localization signal (N, residues 14-31 of SEQ ID NO: 14), a single SAP DNA-binding motif (residues 347-381 of SEQ ID NO: 14), a coiled-coil region (CC, residues 521-563 of SEQ ID NO: 14), and a long C-terminal proline-rich segment (P, residues 564-811 of SEQ ID NO: 14). The three isoforms of RBM15 (RBM15$_S$, RBM15$_{S+AE}$ and RBM15$_L$) share an identical 2863-bp 5' coding sequence (nucleotides 84 to 2946 of SEQ ID Nos. 7, 9, and 11) and differ only in their extreme C-termini, distal to the location of the t(1;22) fusion junction, due to splicing of alternative exons. Specifically, RBM15$_L$, the longest RBM15 transcript (approx. 9 kb), contains a unique 416-bp 3' exon (nucleotides 2947 to 3362 of SEQ ID NO: 11) and encodes a predicted 957-aa protein (mass, 104.6 kDa; SEQ ID NO: 12), whereas the shortest transcript, RBM15$_S$ (approx. 4 kb), possesses a divergent 3' sequence (nucleotides 2947 to 3312 of SEQ ID NO: 7) and encodes a 969-aa protein (mass, 106.2 kDa; SEQ ID NO: 8). Detailed analysis of the approximately 4-kb RBM15 transcript revealed a variant, RBM15$_{S+AE}$ (short transcript plus alternative exon), which contains an additional 111-bp exon (nucleotides 2947 to 3057 of SEQ ID NO: 9) interposed between the 2,863-bp common sequence and the 366-bp sequence in RBM15$_S$ and encodes a polypeptide of 977 aa (mass, 107.1 kDa; SEQ ID NO: 10). All RBM15 isoforms contain three RNA recognition motifs (RRM; residues 170-252, 374-451 and 455-529 of SEQ ID Nos. 8, 10, and 12), a bipartite nuclear localization signal (N, residues 716-733 of SEQ ID Nos. 8, 10, and 12), and a SPOC domain (S, residues 714-954 of SEQ ID Nos. 8, 10, and 12). Several regions in RBM15 of potential functional importance are characterized by a high content of specific aa, including a glycine/serine-rich segment (residues 60-166 of SEQ ID Nos. 8, 10, and 12), a small proline-rich (LPPPPPPPLP) motif (residues 315-324 of SEQ ID Nos. 8, 10, and 12), an arginine-rich portion (residues 616-732 of SEQ ID Nos. 8, 10, and 12), and a short C-terminal serine-rich segment (GSSDSRSSSSSAASD) at amino acids 865-879 of SEQ ID Nos. 8, 10, and 12. The 1883-aa RBM15-MKL1 chimeric protein (mass, 203.1 kDa; SEQ ID NO: 2) is comprised of the common N-terminal portion of RBM15 (residues 1 to 954 of SEQ ID Nos. 8, 10, and 12) and all but the first two residues of MKL1, thus containing all identified motifs of each normal protein. By contrast, the reciprocal MKL1-RBM15 fusions contain only the first two aa of MKL1 fused to the short C-terminal sequences of either RBM15$_S$ or RBM15$_{S+AE}$, and are predicted to encode peptides of only 17 (SEQ ID NO: 4) and 25 (SEQ ID NO: 6) amino acids, respectively. The portions of the schematic illustrating the alternative C-termini of RBM15 and the predicted MKL1-RBM15 fusion peptides are enlarged for clarity, and are thus not to scale.

Compositions and methods for the identification, diagnosis, and treatment of leukemia or a genetic predisposition to leukemia are provided. The present invention is based on the discovery of two reciprocal fusion genes, RBM15-MKL1 and MKL1-RBM15, that result from the t(1;22)(p13;q13) chromosomal translocation event associated with acute megakaryoblastic leukemia (AMKL). In particular, the invention provides the novel nucleotide sequences of a transcript of the RBM15-MKL1 fusion gene (SEQ ID NO: 1) and two transcripts, MKL1-RBM15$_S$ (SEQ ID NO: 3) and MKL1-RBM15$_{S+AE}$ (SEQ ID NO: 5), of the MKL1-RBM15 fusion gene. Additionally provided are the amino acid sequences (SEQ ID NOS: 2, 4, and 6, respectively) of the fusion proteins encoded by such nucleotide sequences. Such nucleotide sequences and amino acid sequences find use, for example, in methods for detecting the t(1;22)(p13;q13) chromosomal translocation event associated with AMKL, methods for identifying agents that bind to the fusion proteins and methods for identifying agents useful for treating AMKL.

In addition to the RBM15-MKL1 and MKL1-RBM15 nucleotide and amino acid sequences, the invention provides isolated nucleotide molecules comprising nucleotide sequences of three transcripts of the RBM15 gene, RBM15$_S$ (SEQ ID NO: 7), RBM15$_{S+AE}$ (SEQ ID NO: 9), and RBM15$_L$ (SEQ ID NO: 11) and the nucleotide sequence of MKL1 (SEQ ID NO: 13). Further provided are isolated proteins comprising the amino acids sequences of the proteins encoded thereby, RBM15$_S$ (SEQ ID NO: 8), RBM15$_{S+AE}$ (SEQ ID NO: 10), and RBM15$_L$ (SEQ ID NO: 12) and MKL1 (SEQ ID NO: 14) respectively. Such nucleotide and amino acid sequences find use, for example, in methods for detecting the t(1;22)(p13;q13) chromosomal translocation event associated with AMKL and methods for identifying agents useful for treating AMKL.

The RBM15 and MKL1 proteins, as well as the noted fusion proteins derived from RBM15 and MKL1, are contemplated to act as transcription factors which bind to corresponding DNA regulatory sequences. Thus these proteins may be used to regulate the expression of genes that include the regulatory DNA sequences that these proteins recognize. Methods for identifying such regulatory DNA sequences based on their ability to bind RBM15, MKL1, RBM15-MKL1 and MKL1-RBM15 are also included in the present invention.

The nucleotide and amino acid sequences of the invention are set forth in the sequence listing. Below is a brief description of the sequences in the sequences listing.

SEQ ID NO: 1 is the nucleotide sequence RBM15-MKL1 cDNA. The open reading frame is from nucleotide 84 through nucleotide 5732.

SEQ ID NO: 2 is the amino acid sequence of the RBM15-MKL1 fusion protein.

SEQ ID NO: 3 is the nucleotide sequence MKL1-RBM15$_S$ cDNA. The open reading frame is from nucleotide 551 through nucleotide 601.

SEQ ID NO: 4 is the amino acid sequence of the MKL1-RBM15$_S$ fusion protein.

SEQ ID NO: 5 is the nucleotide sequence MKL1-RBM15$_{S+AE}$ cDNA. The open reading frame is from nucleotide 551 through nucleotide 625.

SEQ ID NO: 6 is the amino acid sequence of the MKL1-RBM15$_{S+AE}$ fusion protein.

SEQ ID NO: 7 is the nucleotide sequence RBM15$_S$ cDNA. The open reading frame is from nucleotide 84 through nucleotide 2990.

SEQ ID NO: 8 is the amino acid sequence of the RBM15$_S$ protein.

SEQ ID NO: 9 is the nucleotide sequence RBM15$_{S+AE}$ cDNA. The open reading frame is from nucleotide 84 through nucleotide 3014.

SEQ ID NO: 10 is the amino acid sequence of the RBM15$_{S+AE}$ protein.

SEQ ID NO: 11 is the nucleotide sequence RBM15$_L$ cDNA. The open reading frame is from nucleotide 84 through nucleotide 2954.

SEQ ID NO: 12 is the amino acid sequence of the RBM15$_L$ protein.

SEQ ID NO: 13 is the nucleotide sequence MKL1 cDNA. The open reading frame is from nucleotide 551 through nucleotide 3346.

SEQ ID NO: 14 is the amino acid sequence of the MKL1 protein.

SEQ ID NO: 15 is the nucleotide sequence of the synthetic oligonucleotide primer herein designated MKL1-294R.

SEQ ID NO: 16 is the nucleotide sequence of the synthetic oligonucleotide primer herein designated MKL1-73R.

SEQ ID NO: 17 is the nucleotide sequence of the synthetic oligonucleotide primer herein designated MKL1-59R.

SEQ ID NO: 18 is the nucleotide sequence of the synthetic oligonucleotide primer herein designated RBM15(S)-2746F.

SEQ ID NO: 19 is the nucleotide sequence of the synthetic oligonucleotide primer herein designated MKL1-204R.

SEQ ID NO: 20 is the nucleotide sequence of the synthetic oligonucleotide primer herein designated MKL1-F.

SEQ ID NO: 21 is the nucleotide sequence of the synthetic oligonucleotide primer herein designated RBM15(S)-2930R.

SEQ ID NO: 22 is the nucleotide sequence of the synthetic oligonucleotide primer herein designated RBM15(L)-1636R.

SEQ ID NO: 23 is the nucleotide sequence of the synthetic oligonucleotide primer herein designated RBM15-1118F.

SEQ ID NO: 24 is the nucleotide sequence of the synthetic oligonucleotide primer herein designated RBM15-1551R.

SEQ ID NO: 25 is the nucleotide sequence of the synthetic oligonucleotide primer herein designated RBM15-2831F.

SEQ ID NO: 26 is the nucleotide sequence of the synthetic oligonucleotide primer herein designated RBM15-3149R.

SEQ ID NO: 27 is the nucleotide sequence of the synthetic oligonucleotide primer herein designated RBM15-1616F.

SEQ ID NO: 28 is the nucleotide sequence of the synthetic oligonucleotide primer herein designated RBM15-2004R.

SEQ ID NO: 29 is the nucleotide sequence of the synthetic oligonucleotide primer herein designated MKL1-155F.

Based on these observations, one embodiment of the present invention provides a first isolated nucleotide molecule comprising the coding sequence (SEQ ID NO: 1) of the RBM15-MKL1 fusion protein, which encodes the RBM15-MKL1 fusion protein (SEQ ID NO: 2), a second isolated nucleotide molecule, comprising the coding sequence (SEQ ID NO: 3) of the MKL1-RBM15$_S$ fusion protein, which encodes the MKL1-RBM15$_S$ fusion protein (SEQ ID NO: 4), a third isolated nucleotide molecule comprising the coding sequence (SEQ ID NO: 5) of the MKL1-RBM15$_{S+AE}$ fusion protein which encodes the MKL1-RBM15$_{S+AE}$ fusion protein (SEQ ID NO: 6), a fourth isolated nucleotide molecule, comprising the coding sequence (SEQ ID NO: 7) of the RBM15$_S$ protein, which encodes the RBM15$_S$ protein (SEQ ID NO: 8), a fifth isolated nucleotide molecule comprising the coding sequence (SEQ ID NO: 9) of the RBM15$_{S+AE}$ protein which encodes the RBM15$_{S+AE}$ protein (SEQ ID NO: 10), a sixth isolated nucleotide molecule, comprising the coding sequence (SEQ ID NO: 11) of the RBM15$_L$ protein, which encodes the RBM15$_L$ protein (SEQ ID NO: 12), and a seventh isolated nucleotide molecule comprising the coding sequence (SEQ ID NO: 13) of the MKL1 protein, which encodes the MKL1 protein (SEQ ID NO: 14).

It is recognized that nucleotide molecules and proteins of the invention will have a nucleotide or an amino acid sequence sufficiently identical to a nucleotide sequence of SEQ ID NO: 1, 3, 5, 7, 9, 11, or 13 or to an amino acid sequence of SEQ ID NO: 2, 4, 6, 8, 10, 12, or 14. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the nucleic acid molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul el al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

The invention encompasses RBM15-MKL1, MKL1-RBM15$_S$, MKL1-RBM15$_{S+AE}$, RBM15$_S$, RBM15$_{S+AE}$, RBM15$_L$, and MKL1 nucleic acid molecules and fragments thereof. Nucleic acid molecules that are fragments of these nucleotide sequences are also encompassed by the present invention. By "fragment" is intended a portion of the nucleotide sequence encoding an RBM15-MKL1, MKL1-RBM15$_S$, MKL1-RBM15$_{S+AE}$, RBM15$_S$, RBM15$_{S+AE}$, RBM15$_L$ or MKL1 protein. A fragment of an RBM15-MKL1, MKL1-RBM15$_S$, MKL1-RBM15$_{S+AE}$, RBM15$_S$, RBM15$_{S+AE}$, RBM15$_L$ or MKL1 nucleotide sequence may encode a biologically active portion of an RBM15-MKL1, MKL1-RBM15$_S$, MKL1-RBM15$_{S+AE}$, RBM15$_S$, RBM15$_{S+AE}$, RBM15$_L$ or MKL1 protein, or it may be a fragment that can be used as a hybridization probe or PCR primer using methods disclosed below. A biologically active portion of an RBM15-MKL1, MKL1-RBM15$_S$, MKL1-RBM15$_{S+AE}$, RBM15$_S$, RBM15$_{S+AE}$, RBM15$_L$ or MKL1 protein can be prepared by isolating a portion of one of the RBM15-MKL1, MKL1-RBM15$_S$, MKL1-RBM15$_{S+AE}$, RBM15$_S$, RBM15$_{S+AE}$, RBM15$_L$, and MKL1 nucleotide sequences of the invention, expressing the encoded portion of the RBM15-MKL1, MKL1-RBM15$_S$, MKL1-RBM15$_{S+AE}$, RBM15$_S$, RBM15$_{S+AE}$, RBM15$_L$ or MKL1 protein (e.g., by recombinant expression in vitro), and assessing the activity of the encoded portion of the RBM15-MKL1, MKL1-RBM15$_S$, MKL1-RBM15$_{S+AE}$, RBM15$_S$, RBM15$_{S+AE}$, RBM15$_L$, and MKL1 protein. Nucleic acid molecules that are fragments of an RBM15-MKL1, MKL1-RBM15$_S$, MKL1-RBM15$_{S+AE}$, RBM15$_S$, RBM15$_{S+AE}$, RBM15$_L$, and MKL1 nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1500, 1600, 1700, 1800, 1900, 2000, 2500, 3000, 3500, 4500, 5000, 5500, 6000, or 6500 nucleotides, or up to the number of nucleotides present in a full-length nucleotide sequence disclosed herein (for example, 6836, 923, 1034, 3312, 3423, 3383, and 4447 nucleotides for SEQ ID NOS: 1, 3, 5, 7, 9, 11, and 13, respectively) depending upon the intended use.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of an RBM15-MKL1, MKL1-RBM15$_S$, MKL1-RBM15$_{S+AE}$, RBM15$_S$, RBM15$_{S+AE}$, RBM15$_L$ or MKL1 nucleotide sequence that encodes a biologically active portion of an RBM15-MKL1, MKL1-RBM15$_S$, MKL1-RBM15$_{S+AE}$, RBM15$_S$, RBM15$_{S+AE}$, RBM15$_L$, or MKL1 protein of the invention will encode at least about 15, 25, 30, 50, 75, 100, 125, 150, 175, 200, 250, or 300 contiguous amino acids, or up to the total number of amino acids present in a full-length RBM15-MKL1, MKL1-RBM15$_S$, MKL1-RBM15$_{S+AE}$, RBM15$_S$, RBM15$_{S+AE}$, RBM15$_L$, or MKL1 protein of the invention (for example, 1883, 17, 25, 969, 977, 957, and 931 amino acids for SEQ ID NOS: 2, 4, 6, 8, 10, 12, and 14, respectively). Fragments of an RBM15-MKL1, MKL1-RBM15$_S$, MKL1-RBM15$_{S+AE}$, RBM15$_S$, RBM15$_{S+AE}$, RBM15$_L$ and MKL1 nucleotide sequence that are useful as hybridization probes for PCR primers generally need not encode a biologically active portion of an RBM15-MKL1, MKL1-RBM15$_S$, MKL1-RBM15$_{S+AE}$, RBM15$_S$, RBM15$_{S+AE}$, RBM15$_L$, and MKL1 protein, respectively.

Nucleic acid molecules that are variants of the nucleotide sequences disclosed herein are also encompassed by the present invention. "Variants" of the RBM15-MKL1, MKL1-RBM15$_S$, MKL1-RBM15$_{S+AE}$, RBM15$_S$, RBM15$_{S+AE}$, RBM15$_L$, and MKL1 nucleotide sequences include those sequences that encode the RBM15-MKL1, MKL1-RBM15$_S$, MKL1-RBM15$_{S+AE}$, RBM15$_S$, RBM15$_{S+AE}$, RBM15$_L$, and MKL1 proteins, respectively, disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the RBM15-MKL1, MKL1-RBM15$_S$, MKL1-RBM15$_{S+AE}$, RBM15$_S$, RBM15$_{S+AE}$, RBM15$_L$, or MKL1 protein disclosed in the present invention as discussed below. Generally, nucleotide sequence variants of the invention will have at least about 45%, 55%, 65%, 75%, 85%, 90%, 91%, 92%, 93%, 94%, 95%, 96%, 97, 98%, or 99% identity to a particular nucleotide sequence disclosed herein. A variant RBM15-MKL1, MKL1-RBM15$_S$, MKL1-RBM15$_{S+AE}$, RBM15$_S$, RBM15$_{S+AE}$, RBM15$_L$ or MKL1 nucleotide sequence will encode a variant RBM15-MKL1, MKL1-

RBM15$_S$, MKL1-RBM15$_{S+AE}$, RBM15$_S$, RBM15$_{S+AE}$, RBM15$_L$, or MKL1 protein, respectively, that has an amino acid sequence having at least about 45%, 55%, 65%, 75%, 85%, 90%, 91%, 92%, 93%, 94%, 95%, 96%, 97, 98%, or 99% identity to the amino acid sequence of an RBM15-MKL1, MKL1-RBM15$_S$, MKL1-RBM15$_{S+AE}$, RBM15$_S$, RBM15$_{S+AE}$, RBM15$_L$, or MKL1 protein disclosed herein.

In addition to the RBM15-MKL1, MKL1-RBM15$_S$, MKL1-RBM15$_{S+AE}$, RBM15$_S$, RBM15$_{S+AE}$, RBM15$_L$ and MKL1 nucleotide sequences shown in SEQ ID NOS: 1, 3, 5, 7, 9, 11, and 13 , it will be appreciated by those skilled in the art that DNA sequence polymorphisms that lead to changes in the amino acid sequences of RBM5-MKL1, MKL1-RBM15$_S$, MKL1-RBM15$_{S+AE}$, RBM15$_S$, RBM15$_{S+AE}$, RBM15$_L$, or MKL1 proteins may exist within a population (e.g., the human population). Such genetic polymorphism in an RBM15-MKL1, MKL1-RBM15, RBM15, and MKL1 gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding an RBM15-MKL1, MKL1-RBM15$_S$, MKL1-RBM15$_{S+AE}$, RBM15$_S$, RBM15$_{S+AE}$, RBM15$_L$, or MKL1 protein, preferably a mammalian RBM15-MKL1, MKL1-RBM15$_S$, MKL1-RBM15$_{S+AE}$, RBM15$_S$, RBM$^{15}$$_{S+AE}$, RBM15$_L$, or MKL1 protein. As used herein, the phrase "allelic variant" refers to a nucleotide sequence that occurs at an RBM15-MKL1, MKL1-RBM15, RBM15, and MKL1 locus or to a polypeptide encoded by the nucleotide sequence. Such natural allelic variations can typically result in 1-5% variance in the nucleotide sequence of the RBM15-MKL1, MKL1-RBM15, RBM15, and MKL1 gene. Any and all such nucleotide variations and resulting amino acid polymorphisms or variations in an RBM15-MKL1, MKL1-RBM15, RBM15, and MKL1 amino acid sequence that are the result of natural allelic variation and that do not alter the functional activity of RBM15-MKL1, MKL1-RBM15$_S$, MKL1-RBM15$_{S+AE}$, RBM15$_S$, RBM15$_{S+AE}$, RBM15$_L$, and MKL1 proteins are intended to be within the scope of the invention.

Moreover, nucleic acid molecules encoding RBM15-MKL1, MKL1-RBM15$_S$, MKL1-RBM15$_{S+AE}$, RBM15$_S$, RBM15$_{S+AE}$, RBM15$_L$, and MKL1 proteins from other species (RBM15-MKL1, MKL1-RBM15$_S$, MKL1-RBM15$_{S+AE}$, RBM15$_S$, RBM15$_{S+AE}$, RBM15$_L$, and MKL1 homologues), which have a nucleotide sequence differing from that of the RBM15-MKL1, MKL1-RBM15$_S$, MKL1-RBM15$_{S+AE}$, RBM15$_S$, RBM15$_{S+AE}$, RBM15$_L$, and MKL1 sequences disclosed herein, are intended to be within the scope of the invention. For example, nucleic acid molecules corresponding to natural allelic variants and homologues of the human RBM15-MKL1, MKL1-RBM15$_S$, MKL1-RBM15$_{S+AE}$, RBM15$_S$, RBM15$_{S+AE}$, RBM15$_L$ and MKL1 cDNAs of the invention can be isolated based on their identity to the human RBM15-MKL1, MKL1-RBM15$_S$, MKL1-RBM15$_{S+AE}$, RBM15$_S$, RBM15$_{S+AE}$, RBM15$_L$, and MKL1 nucleic acids disclosed herein using the human cDNA, or a portion thereof, as a hybridization probe according to standard hybridization techniques under stringent hybridization conditions as disclosed herein.

In addition to naturally occurring allelic variants of the RBM15-MKL1, MKL1-RBM15$_S$, MKL1-RBM15$_{S+AE}$, RBM15$_S$, RBM15$_{S+AE}$, RBM15$_L$, and MKL1 sequences that may exist in the population, the skilled artisan will further appreciate that changes can be introduced by mutation into the nucleotide sequences of the invention thereby leading to changes in the amino acid sequence of the encoded RBM15-MKL1, MKL1-RBM15$_S$, MKL1-RBM15$_{S+AE}$, RBM15$_S$, RBM15$_{S+AE}$, RBM15$_L$, and MKL1 proteins, respectively, without altering the biological activity of the RBM15-MKL1, MKL1-RBM15$_S$, MKL1-RBM15$_{S+AE}$, RBM15$_S$, RBM15$_{S+AE}$, RBM15$_L$, and MKL1 proteins. Thus, an isolated nucleic acid molecule encoding an RBM15-MKL1, MKL1-RBM15$_S$, MKL1-RBM15$_{S+AE}$, RBM15$_S$, RBM15$_{S+AE}$, RBM15$_L$, or MKL1 protein having a sequence that differs from that of SEQ ID NOS: 2, 4, 6, 8, 10, 12, or 14, respectively, can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of an RBM15-MKL1, MKL1-RBM15$_S$, MKL1-RBM15$_{S+AE}$, RBM15$_S$, RBM15$_{S+AE}$, RBM15$_L$, or MKL1 protein (e.g., the sequence of SEQ ID NOS: 2, 4, 6, 8, 10, 12, or 14, respectively) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif.

Alternatively, variant RBM15-MKL1, MKL1-RBM15$_S$, MKL1-RBM15$_{S+AE}$, RBM15$_S$, RBM15$_{S+AE}$, RBM15$_L$, and MKL1 nucleotide sequences can be made by introducing mutations randomly along all or part of an RBM15-MKL1, MKL1-RBM15$_S$, MKL1-RBM15$_{S+AE}$, RBM15$_S$, RBM15$_{S+AE}$, RBM15$_L$ or MKL1 coding sequence, such as by saturation mutagenesis, and the resultant mutants can be screened for RBM15-MKL1, MKL1-RBM15$_S$, MKL1-RBM15$_{S+AE}$, RBM15$_S$, RBM15$_{S+AE}$, RBM15$_L$, or MKL1 biological activity to identify mutants that retain activity. Following mutagenesis, the encoded protein can be expressed recombinantly, and the activity of the protein can be determined using standard assay techniques.

Thus, the nucleotide sequences of the invention include the sequences disclosed herein as well as fragments and variants thereof. The RBM15-MKL1, MKL1-RBM15$_S$, MKL1-RBM15$_{S+AE}$, RBM15$_S$, RBM15$_{S+AE}$, RBM15$_L$, and MKL1 nucleotide sequences of the invention, and fragments and variants thereof, can be used as probes and/or primers to identify and/or clone RBM15-MKL1, MKL1-RBM15$_S$, MKL1-RBM15$_{S+AE}$, RBM15$_S$, RBM15$_{S+AE}$, RBM15$_L$, and MKL1 homologues in other cell types, e.g., from other tissues, as well as homologues from other mammals. Such probes can be used to detect transcripts or genomic sequences encoding the same or identical proteins.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). RBM15-MKL1, MKL1-RBM15$_S$, MKL1-RBM15$_{S+AE}$, RBM15$_S$, RBM15$_{S+AE}$, RBM15$_L$, and MKL1 nucleotide sequences isolated based on their sequence identity to the RBM15-MKL1, MKL1-RBM15$_S$, MKL1-RBM15$_{S+AE}$, RBM15$_S$, RBM15$_{S+AE}$, RBM15$_L$ and MKL1 nucleotide sequences set forth herein or to fragments and variants thereof are encompassed by the present invention.

In a hybridization method, all or part of a known RBM15-MKL1, MKL1-RBM15$_S$, MKL1-RBM15$_{S+AE}$, RBM15$_S$, RBM15$_{S+AE}$, RBM15$_L$ or MKL1 nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known RBM15-MKL1, MKL1-RBM15$_S$, MKL1-RBM15$_{S+AE}$, RBM15$_S$, RBM15$_{S+AE}$, RBM15$_L$, and MKL1 nucleotide sequence disclosed herein. Degenerate primers designed on the basis of conserved nucleotides or amino acid residues in a known RBM15-MKL1, MKL1-RBM15$_S$, MKL1-RBM15$_{S+AE}$, RBM$_{15S}$, RBM15$_{S+AE}$, RBM15$_L$ and MKL1 nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of an RBM15-MKL1, MKL1-RBM15$_S$, MKL1-RBM15$_{S+AE}$, RBM15$_S$, RBM15$_{S+AE}$, RBM15$_L$, and MKL1 nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

As used herein, the term "hybridizes under stringent conditions" is intended to describe conditions for hybridization and washing under which nucleotide sequences having at least about 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1-6.3.6. A preferred, non-limiting example of stringent hybridization conditions is hybridization in 6× sodium chloride/sodium citrate (SSC) at about 45° C., followed by one or more washes in 0.2×SSC, 0.1% SDS at 50-65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to an RBM15-MKL1, MKL1-RBM15$_S$, MKL1-RBM15$_{S+AE}$, RBM15$_S$, RBM15$_{S+AE}$, RBM15$_L$, or MKL1 nucleotide sequence of the invention corresponds to a naturally occurring nucleic acid molecule. As used herein, a "naturally occurring" nucleic acid molecule refers to an RNA or DNA molecule having a nucleotide sequence that occurs in nature (e.g., encodes a natural protein).

Thus, in addition to the RBM15-MKL1, MKL1-RBM15$_S$, MKL1-RBM15$_{S+AE}$, RBM15$_S$, RBM15$_{S+AE}$, RBM15$_L$, and MKL1 nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the RBM15-MKL1, MKL1-RBM15$_S$, MKL1-RBM15$_{S+AE}$, RBM15$_S$, RBM15$_{S+AE}$, RBM15$_L$, and MKL1. By inserting any of the nucleotide sequences of the present invention into an appropriate vector, one skilled in the art can readily produce large quantities of the specific sequence. Alternatively, the RBM15-MKL1, MKL1-RBM15$_S$ and MKL1-RBM15$_{S+AE}$, nucleotide sequences of the invention can be further utilized in methods of producing the RBM15-MKL1, MKL1-RBM15$_S$ and MKL1-RBM15$_{S+AE}$ fusion proteins, respectively, by introduction of the appropriate coding sequence into a host/vector expression system. There are numerous host/vectors systems available for the propagation of nucleotide sequences and/or the production of expressed proteins. These include, but are not limited to, plasmid and viral vectors, and prokaryotic and eukaryotic host. One skilled in the art can readily adapt any host/vector system which is capable of propagating or expressing heterologous DNA to produce or express the sequences of the present invention. Of course, the RBM15-MKL1, MKL1-RBM15$_S$ and MKL1-RBM15$_{S+AE}$ fusion proteins or polypeptides derived therefrom may also be produced by other means known in the art such as, for example, chemical synthesis or in vitro transcription/translation.

Also provided by the present invention are an isolated RBM15-MKL1 fusion protein (SEQ ID NO: 2), an isolated MKL1-RBM15$_S$ fusion protein (SEQ ID NO: 4), and an isolated MKL1-RBM15$_{S+AE}$ fusion protein (SEQ ID NO: 6), an isolated RBM15$_S$ protein (SEQ ID NO: 8), an isolated RBM15$_{S+AE}$ protein (SEQ ID NO: 10), an isolated RBM15$_L$ protein (SEQ ID NO: 12), and an isolated MKL1 protein (SEQ ID NO: 14), which are encoded by their cognate nucleotides, that is, by SEQ ID NO: 1, 3, 5, 7, 9, 11, and 13, respectively. Synthetic oligopeptides derived from SEQ ID NO: 2, 4, 6, 8, 10, 12, and 14 are also provided in this embodiment of the invention.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated nucleic acid molecules can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

An isolated protein that is substantially free of cellular material includes preparations of RBM15-MKL1, MKL1-

RBM15$_S$, MKL1-RBM15$_{S+AE}$, RBM15$_S$, RBM15$_{S+AE}$, RBM15$_L$, or MKL1 protein having less than about 30%, 20%, 10%, or 5% (by dry weight) of non-like protein (also referred to herein as a "contaminating protein"). When the RBM15-MKL1, MKL1-RBM15$_S$, MKL1-RBM15$_{S+AE}$, RBM15$_S$, RBM15$_{S+AE}$, RBM15$_L$, or MKL1 protein or biologically active portion thereof is recombinantly produced, preferably, culture medium represents less than about 30%, 20%, 10%, or 5% of the volume of the protein preparation. When RBM15-MKL1, MKL1-RBM15$_S$, MKL1-RBM15$_{S+AE}$, RBM15$_S$, RBM15$_{S+AE}$, RBM15$_L$, or MKL1 protein is produced by chemical synthesis, preferably the protein preparations have less than about 30%, 20%, 10%, or 5% (by dry weight) of chemical precursors or non-like chemicals.

In Example 1, the present invention provides evidence that the nucleotide sequences containing the RBM15-MKL1 and MKL1-RBM15 fusion genes are present in patients with t(1;22) AMKL. Based on this observation, the present invention provides methods of assaying for the presence of nucleotide sequences containing the RBM15-MKL1 and MKL1-RBM15 fusions in a sample and thus provides an assay for the detection of t(1;22) leukemias, as explained in Example 1. The methods of the invention can involve any means known in the art for detecting the presence of specific nucleotide sequences in a sample including, but not limited to, nucleic acid hybridization and detection methods (e.g., "Southerns," "Northerns" and the like) fluorescence in situ hybridization (FISH) and detection methods, or polymerase chain reaction (PCR) amplification and detection methods, particularly reverse transcriptase-polymerase chain reaction amplification (RT-PCR).

One example of the assay methods of the present invention which are used to detect RBM15-MKL1 or MKL1-RBM15 fusion gene are based on the preferential amplification of sequences within a sample which contain the nucleotide sequences encoding the RBM15-MKL1, MKL1-RBM15$_S$ or MKL1-RBM15$_{S+AE}$ fusion proteins. In one embodiment of the invention, RT-PCR is utilized to detect the t(1,22) rearrangement that is associated with AMLK. The method involves the use of RT-PCR to detect the presence of transcripts from the RBM15-MKL1 or MKL1-RBM15 fusion genes. The method involves reverse transcription via reverse transcriptase of an RNA sample from a patient to produce cDNA. For reverse transcription, an oligo-dT primer can be use, or alternatively, a primer designed to specifically anneal to RBM15-MKL1 mRNA, MKL1-RBM15$_S$mRNA, or MKL1-RBM15$_{S+AE}$mRNA can be employed to prime cDNA synthesis. Such primers can be designed from the nucleotide sequences of the invention as set forth in SEQ ID NOS: 1, 3, and 5 using methods known to those of ordinary skill in the art. Then, PCR amplification of the cDNA can be performed utilizing primers designed to amplify at least a portion of the nucleotide sequences of to RBM15-MKL1, MKL1-RBM15$_S$ or MKL1-RBM15$_{S+AE}$. The amplified cDNA can be detected by methods known in the art such as, for example, agarose gel electrophoresis and ethidium bromide staining. The detection of the desired cDNA corresponding to at least a portion of the RBM15-MKL1, MKL1-RBM15$_S$ or MKL1-RBM15$_{S+AE}$ indicates that the sample is from a patient with the t(1,22) rearrangement.

The methods of the invention involve the use of PCR amplification, particularly RT-PCR. Methods for PCR amplification are known in the art. Oligonucleotide primers can be designed for use in PCR reactions to amplify corresponding DNA sequences from genomic DNA or cDNA extracted from any organism of interest. Methods for PCR amplification and for designing PCR primers are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Other known methods of PCR that can be used in the methods of the invention include, but are not limited to, methods using paired primers, nested primers, single specific primers, degenerate primers, gene-specific primers, mixed DNA/RNA primers, vector-specific primers, partially mismatched primers, and the like.

In addition to methods which rely on the amplification of a target sequence, the present invention further provides methods for identifying nucleic acids containing the RBM15-MKL1 fusion gene which do not require sequence amplification and are based on the known methods of Southern (DNA:DNA) and Northern (DNA:RNA) blot hybridizations, and FISH of chromosomal material, using probes derived from the nucleotide sequences of the invention. Additionally, other nucleotide sequences of chromosomes 1 and 22 that are known to art and for which are disclosed herein to occur in the vicinity of the chromosomal breakpoint for the t(1;22)(p13;q13) chromosomal translocation event associated with AMKL can be used in the methods of the invention. That is, nucleic acid probes can be used that comprise nucleotide sequences in proximity to the t(1;22)(p13;q13) chromosomal translocation event, or breakpoint. By "in proximity to" is intended within about 10 kilobases (kb) of the t(1;22) breakpoint. Such other nucleotide sequences include, but are not limited to, RP11-260A24 (Accession no. AC025987), RP5-1042K10 (Accession no. AL022238), RP11-313L7, RP5-1125M8 (Accession no. AL356387), RP4-665N5, RP4-743K1, RP11-50F6, RP3-377F16 (Accession no. Z93783), RP4-591N18 (Accession no. AL031594), RP1-229A8 (Accession no. Z86090), and RP4-735G18 (Accession no. AL096703). The clones not identified with Accession numbers are also available from the Roswell Park Cancer Institute (RPCI-BAC library).

In another embodiment of the invention, methods are provided detecting the t(1,22) rearrangement involving FISH (fluorescence in situ hybridization ) of human chromosomal material. For example, a probe that is comprised of nucleotide sequences that span the breakpoint in either a wild-type chromosome 1 or 22 can be used. Such a probe can hybridize to both derivative chromosomes in the case of a t(1,22) rearrangement. Alternatively, two probes, each labeled with a different detection reagent, can be utilized. The first probe is capable of hybridizing to sequences within the region of chromosomal band 1p13, and the second probe is capable of binding to the region of chromosomal band 22q13. The two probes are also selected such that, in a t(1,22) rearrangement, both probes hybridize to the same derivative chromosome, whether it be chromosome 1 or 22. In such a case, a signal from each of the probes is observed on the same chromosome.

The nucleic acid probes of the present invention include DNA as well as RNA probes, such probes being generated using techniques known in the art (Sambrook et al., eds., Molecular Cloning, Cold Spring Harbor Press, Cold Spring Harbor, N.Y. (1989)). A skilled artisan can employ such known techniques using the RBM15$_S$, RBM15$_{S+AE}$, RBM15$_L$, MKL1, RBM15-MKL1, MKL1-RBM15$_S$, and MKL1-RBM15$_{S+AE}$ nucleotide sequences herein described, or fragments thereof, as probes.

For nucleic acid probes, examples of detection reagents include, but are not limited to radiolabeled probes, enzymatic labeled probes (horse radish peroxidase, alkaline phosphatase), and affinity labeled probes (biotin, avidin, or steptavidin). For antibodies, examples of detection reagents include, but are not limited to, labeled secondary antibodies, or in the alternative, if the primary antibody is labeled, the chromophoric, enzymatic, or antibody binding reagents which are capable of reacting with the labeled antibody. One skilled in the art will readily recognize that the antibodies and nucleic acid probes described in the present invention can readily be incorporated into one of the established kit formats which are well known in the art.

The samples used in the detection methods of the present invention include, but are not limited to, cells or tissues, protein, membrane, or nucleic acid extracts of the cells or tissues, and biological fluids such as blood, serum, and plasma. The sample used in the methods of the invention will vary based on the assay format, nature of the detection method, and the tissues, cells or extracts which are used as the sample. Methods for preparing protein extracts, membrane extracts or nucleic acid extracts of cells are well known in the art and can be readily be adapted in order to obtain a sample which is compatible with the method utilized (see, for example, K. Budelier et al., Chapter 2, "Preparation and Analysis of DNA," M. E. Greenberg et al., Chapter 4, "Preparation and Analysis of RNA" and M. Moos et al., Chapter 10, "Analysis of Proteins," in Ausubel et al., Current Protocols in Molecular Biology, Wiley Press, Boston, Mass. (1993)). One preferred type of sample which can be utilized in the present invention is derived from isolated lymphoma cells. Such cells can be used to prepare a suitable extract or can be used in procedures based on in situ analysis.

The present invention further provides antibodies specific to epitopes of the RBM15-MKL1, MKL1-RBM15$_S$, or MKL1-RBM15$_{S+AE}$ fusion proteins and methods of detecting the RBM15-MKL1, MKL1-RBM15$_S$, or MKL1-RBM15$_{S+AE}$ fusion proteins, or any combination thereof, that rely on the ability of these antibodies to selectively bind to specific portions of the RBM15-MKL1, MKL1-RBM15$_S$, or MKL1-RBM15$_{S+AE}$ proteins that are unique to that fusion protein. Such antibodies do not bind preferentially to the RBM15 or MKL1 proteins.

The present invention further provides methods of detecting the presence of at least one of the RBM15-MKL1, MKL1-RBM15$_S$, and MKL1-RBM15$_{S+AE}$ fusion proteins. Antibodies can be prepared which recognize a fusion protein of the invention. Such antibodies can be used to detect the presence of the fusion protein in samples from human cells. The methods of the invention involve the use of antibodies that bind to at least one of the fusion proteins of the invention and antibody detection systems that are known to those of ordinary skill in the art. Such methods find use in diagnosis and treatment of AMKL, for example, to determine if particular cells or tissues express the RBM15-MKL1, MKL1-RBM15$_S$, and/or the MKL1-RBM15$_{S+AE}$ fusion proteins.

Conditions for incubating an antibody with a test sample vary depending on the format employed for the assay, the detection methods employed, the nature of the test sample, and the type and nature of the antibody used in the assay. One skilled in the art will recognize that any one of the commonly available immunological assay formats (such as radioimmunoassays, enzyme-linked immunosorbent assays, diffusion based ouchterlony, or rocket inmunofluorescent assays) can readily be adapted to employ the antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of Enzyme Immunoassays: Laboratory Techniques in Biochemistry and Molecular Biology, Elsevier Science Publishers, Amsterdam, The Netherlands (1985).

In another embodiment of the immunoassays of the invention, the anti-RBM15-MKL1 antibody, the anti-MKL1-RBM15$_S$ antibody, or the anti-MKL1-RBM15$_{S+AE}$ antibody is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling antibodies to such solid supports are well known in the art (see, for example, Weir, D. M. et al., Handbook of Experimental Immunology, 4th Ed., Blackwell Scientific Publications, Oxford, England, Chapter 10 (1986)).

Additionally, one or more of the antibodies used in the above described methods can be detectably labeled prior to use. Antibodies can be detectably labeled through the use of radioisotopes, affinity labels (such as biotin, avidin, etc.), enzymatic labels (such as horse radish peroxidase, alkaline phosphatase, etc.) fluorescent labels (such as FITC or rhodamine, etc.), paramagnetic atoms, etc. Procedures for accomplishing such labeling are well-known in the art; see, for example, Stemberger, L. A. et al., J. Histochem. Cytochem. 18:315-333 (1970); Bayer, E. A. et al., Meth. Enzym. 62:308-315 (1979); Engrall, E. et al., J. Immunol. 109:129-135 (1972); Goding, J. W., J. Immunol. Meth. 13:215-226 (1976).

The present invention further includes methods for selectively killing cells expressing the RBM15-MKL1 fusion protein, the MKL1-RBM15$_S$ fusion protein, and/or the MKL1-RBM15$_{S+AE}$ fusion protein by, for example, contacting a cell expressing the RBM15-MKL1, MKL1-RBM15$_S$, and/or MKL1-RBM15$_{S+AE}$ fusion protein with a toxin derivatized antibody, wherein the antibody is capable of selectively binding to the fusion protein with only weak or no binding to non-fusion RBM15 or MKL1 protein. An example of such an antibody is toxin derivatized antibodies which bind to the RBM15-MKL1 fusion protein junction. As used herein, an antibody is said to be "toxin-derivatized" when the antibody is covalently attached to a toxin moiety. Procedures for coupling such moieties to a molecule are well known in the art. The binding of a toxin derivatized antibody to a cell brings the toxin moiety into close proximity to the cell and thereby promotes cell death. By providing such an antibody molecule to a mammal, the cell expressing the fusion protein can be preferentially killed. Any suitable toxin moiety may be employed; however, it is preferable to employ toxins such as, for example, the ricin toxin, the cholera toxin, the diphtheria toxin, radioisotopic toxins, or membrane-channel-forming toxins.

The antibodies or toxin-derivatized antibodies of the present invention may be administered to a mammal intravenously, intramuscularly, subcutaneously, enterally, topically or parenterally. When administering antibodies or peptides by injection, the administration may be by continuous injections, or by single or multiple injections.

The antibodies or toxin-derivatized antibodies of the present invention are intended to be provided to recipient mammal in a "pharmaceutically acceptable form" in an amount sufficient to "therapeutically effective." An amount is said to be therapeutically effective if the dosage, route of administration, etc. of the agent are sufficient to preferentially kill a portion of the cells expressing the RBM15-MKL1 or MKL1-RBM15 fusion protein. An antibody is said to be in a "pharmacologically acceptable form" if its administration can be tolerated by a recipient patient. The antibodies of the present invention can be formulated according to known methods of preparing pharmaceutically useful compositions, whereby these materials, or their functional derivatives, are combined with a pharmaceutically acceptable carrier vehicle. Suitable vehicles and their formulation, inclusive of other human proteins, e.g., human serum albumin, are described, for example, in Remington's Pharmaceutical Sciences, 16th ed., Osol, A., ed., Mack, Easton Pa. (1980). In order to form a pharmaceutically acceptable composition which is suitable for effective administration, such compositions will contain an effective amount of an antibody of the present invention together with a suitable amount of carrier. In addition to carriers, the antibodies of the present invention may be supplied in humanized form. Humanized antibodies may be produced, for example by replacing an immunogenic portion of an antibody with a corresponding, but non-immunogenic portion (i.e., chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041-1043 (1988); Liu, A. Y. et al., Proc. Natl. Acad. Sci. USA 84:3439-3443 (1987); Liu, A. Y. et al., J. Immunol. 139: 3521-3526 (1987); Sun, L. K. et al., Proc. Natl. Acad. Sci. USA 84:214-218 (1987); Nishimura, Y. et al., Cancer Res. 47:999-1005 (1987); Wood, C. R. et al., Nature 314:446-449 (1985)); Shaw el al., J. Natl. Cancer Inst. 80:1553-1559 (1988).

In providing a patient with an antibody or toxin-derivatized antibody, the dosage of administered agent will vary depending upon such factors as the patient's age, weight, height, sex, general medical condition, previous medical history, etc. In general, it is desirable to provide the recipient with a dosage of the antibody which is in the range of from about 1 pg/kg to 10 mg/kg (body weight of patient), although a lower or higher dosage may be administered.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to a noncoding region of the coding strand of a nucleotide sequence encoding a protein of interest. The noncoding regions are the 5' and 3' sequences that flank the coding region and are not translated into amino acids.

Given the coding-strand sequence encoding, for example, an RBM15-MKL1 fusion protein disclosed herein (e.g., SEQ ID NO: 1), antisense nucleic acids of the invention can be designed according to the rules of Watson and Crick base pairing. The antisense nucleic acid molecule can be complementary to the entire coding region of RBM15-MKL1 mRNA, but more preferably is an oligonucleotide that is antisense to only a portion of the coding or noncoding region of RBM15-MKL1 mRNA. For example, the antisense oligonucleotide can be complementary to the region surrounding the translation start site of RBM15-MKL1 mRNA. A preferred antisense oligonucleotide for selective hybridisation to fusion transcripts will include the region spanning the RBM15 portion of the fusion transcript and the MKL1 portion of the fusion transcript. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art. Similarly, antisense nucleotide molecules can be prepared for the nucleotide sequences encoding the MKL1-RBM15$_S$, and MKL1-RBM15$_{S+AE}$ fusion proteins (SEQ ID NOS: 3 and 5, respectively).

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

When used therapeutically, the antisense nucleic acid molecules of the invention are typically administered to a subject or generated in situ such that they hybridize with or bind to cellular mRNA and/or genomic DNA encoding a protein of the invention to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In another embodiment of the present invention, methods are provided for modulating the translation of at least one RNA selected from the group consisting of those RNAs encoding the RBM15-MKL1, MKL1-RBM15$_S$, or MKL1-RBM15$_{S+AE}$ fusion protein in the cell. Specifically, such methods comprise introducing into a cell a DNA sequence which is capable of transcribing RNA which is complimentary to the mRNA encoding either the RBM15-MKL1, MKL1-RBM15$_S$, or MKL1-RBM15$_{S+AE}$ fusion protein. By introducing such a sequence into a cell, antisense RNA will be produced that will hybridize to RBM15-MKL1, MKL1-RBM15$_S$, or MKL1-RBM15$_{S+AE}$ mRNA and block the translation of the RBM15-MKL1 or MKL1-RBM15 fusion protein, respectively. Antisense cloning has been described elsewhere in more detail by Methis et al., Blood 82:1395-1401 (1993); Stein et al., Science 261:1004-1012 (1993); Mirabella et al., Anti-Cancer Drug Design 6:647-661 (1991); Rosenberg et al., Nature 313:703-706 (1985); Preiss et al., Nature 313:27-32 (1985), Melton, Proc. Natl. Acad. Sci. USA 82:144-148 (1985) and Kim et al., Cell 42:129-138 (1985). Transcription of the introduced DNA will result in multiple copies of the antisense RNA being generated. By controlling the level of transcription of antisense RNA, and the tissue specificity of expression via promoter selection or gene targeting of the antisense expression sequence, one skilled in the art can regulate the level of translation of the RBM15-MKL1, MKL1-RBM15$_S$, and/or MKL1-RBM15$_{S+AE}$ fusion proteins in specific cells within a patient. In a related method, one or more synthetic antisense oligonucleotides that are complementary to the RBM15-MKL1, MKL1-RBM15$_S$, and/or MKL1-RBM15$_{S+AE}$ coding sequences of the invention, optionally including chemical modifications designed to stabilize the oligonucleotide or enhance its uptake into cells, are administered to cells of a patient by known methods (see, for example, R. W. Wagner, Nature 372:333-335 (1994); J. Lisziewicz et al., Proc. Natl. Acad. Sci. (USA) 90:3860-3864 (1993); S. Fitzpatrick-McElligott, Bio/Technology 10: 1036-1040 (1992); E. Uhlmann et al., Chemical Reviews 90:543-583 (1990); and B. Tseng et al., Cancer Gene Therapy 1:65-71 (1994)).

The invention also encompasses ribozymes, which are catalytic RNA molecules with ribonuclease activity that are capable of cleaving a single-stranded nucleic acid, such as an mRNA, to which they have a complementary region. The level of expression of the RBM15-MKL1, MKL1-RBM15$_S$, and/or MKL1-RBM15$_{S+AE}$ fusion proteins can also be controlled through the use of ribozyme technology. Ribozymes (e.g., hammerhead ribozymes (described in Haselhoff and Gerlach (1988) Nature 334:585-591)) can be used to catalytically cleave RBM15-MKL1, MKL1-RBM1$_S$, or MKL1-RBM15$_{S+AE}$ mRNA transcripts to thereby inhibit translation of RBM15-MKL1, MKL1-RBM15$_S$, and MKL1-RBM15$_{S+AE}$ mRNA, respectively. A ribozyme having specificity for an RBM15-MKL1-, MKL1-RBM15$_S$-, or MKL1-RBM$_{15S+AE}$-encoding nucleic acid can be designed based upon the nucleotide sequence of the corresponding cDNA disclosed herein (e.g., SEQ ID NOS: 1, 3, and 5, respectively). See, e.g., Cech et al., U.S. Pat. No. 4,987,071; and Cech et al., U.S. Pat. No. 5,116,742. Alternatively, RBM15-MKL1, MKL1-RBM15$_S$, or MKL1-RBM15$_{S+AE}$ mRNA can be used to select a catalytic RNA having a specific ribonuclease activity from a pool of RNA molecules. See, e.g., Bartel and Szostak (1993) Science 261:1411-1418.

The present invention further provides methods of generating transgenic animals and transformed cell lines which contain the RBM15-MKL1, MKL1-RBM15$_S$, and/or MKL1-RBM15$_{S+AE}$ nucleotide sequences. Such animals and cell lines are useful as animal models for human t(1;22) leukemias. In general, methods of generating transgenic animals and transformed cell lines are well known in the art (for example, see Grosveld et al., Transgenic Animals, Academic Press Ltd., San Diego, Calif. (1992)). Using the nucleotide sequences disclosed herein for the RBM15-MKL1, MKL1-RBM15$_S$, or MKL1-RBM15$_{S+AE}$ or coding sequences for the RBM15-MKL1, MKL1-RBM15$_S$, and/or MKL1-RBM15$_{S+AE}$ fusion proteins, a skilled artisan can readily generate a transgenic animal and transformed cell lines which contains and expresses the RBM15-MKL1 fusion protein, the MKL1-RBM15$_S$ fusion protein, and/or MKL1-RBM15$_{S+AE}$ fusion protein. Transgenic animals (such as mice and pigs) which express the RBM15-MKL1 fusion gene can be used as an animal model for human t(1;22) leukemia. Transgenic animals which express the RBM15-MKL1 fusion protein, the MKL1-RBM15$_S$ fusion protein, or MKL1-RBM15$_{S+AE}$ fusion protein, or any combination thereof, are useful for determining, at the molecular level, the roles of the RBM15-MKL1, MKL1-RBM15$_S$, and MKL1-RBM15$_{S+AE}$ fusion proteins in the development of acute megakaryoblastic leukemia. Such animals serve as models for the development of alternative therapies for t(1;22) lymphoma.

Transformed eukaryotic cell lines that express on or more of the fusion of proteins of the invention can be used, for example, to screen for agents that are useful for treating AMKL. Preferably such cell lines are mammalian cell lines. More preferably, such cell lines are human cell lines. Generally, desired agents are those that suppress or eliminate phenotypic changes that occur as a result of the expression of one or more fusion proteins of the invention in the cell. Phenotypic changes that occur as a result of the expression of one or more fusion proteins of the invention in the cell include, for example, the presence of CD61 and absence of peroxidase and esterase (See, e.g. Bennett et al., Ann. Intern Med 103:460-462 (1985); Skinnider L. F. et al., Acta Haematologica 98 (1): 26 (1997); Avanzi et al., J. Cell Physiol. 145: 458-464 (1990); Avanzi et al., Brit. J Haematol. 69: 359 (1988)).

Such desired agents may be further screened for selectivity by determining whether they suppress or eliminate phenotyic changes or activities associated with expression of unfused RBM15 and/or MKL1 proteins in cells that either express such unfused proteins naturally or are engineered to express such proteins. Selective agents are those which suppress or eliminate phenotypes associated with expression of the fusion protein but which do not suppress or eliminate the phenotypes associated with the unfused RBM15 and MKL1 proteins. Typically, the agents are screened by administering the agent to the cell. It is recognized that it is preferable that a range of dosages of a particular agent be administered to the cells to determine if the agent is useful for treating AMKL. Appropriate cell lines that can be used in this method include, but are not limited to, DAMI, MEG-01, M-07e, CMK, CHRF-288-11 and UT7 cells. In another embodiment of the present invention, methods are provided for identifying agents which are capable of binding to the RBM15-MKL1, MKL1-RBM15$_S$, or MKL1-RBM15$_{S+AE}$ fusion proteins herein described. Such methods comprise (a) contacting a candidate agent with RBM15-MKL1, MKL1-RBM15$_S$, or MKL1-RBM15$_{S+AE}$ fusion protein, or fragment thereof, and (b) determining whether the candidate agent binds to the fusion protein. Using this method, agents which can be used to modulate the activity of the RBM15-MKL1, MKL1-RBM15$_S$, or MKL1-RBM15$_{S+AE}$ fusion protein can be identified. Such methods can additionally comprise an additional step to select from the identified agents those which do not bind RBM15 or MKL1 proteins. Such an additional step involves contacting the agent with an RBM15 or MKL1 protein, or fragment thereof and determining whether the agent binds to the protein or fragment.

There are numerous variations of the above assays which can be used by a skilled artisan without the need for undue experimentation in order to isolate agonists, antagonists, and ligands of the RBM15-MKL1, MKL1-RBM15$_S$, and/or MKL1-RBM15$_{S+AE}$ fusion protein; see, for example, Burch, R. M., in Medications Development. Drug Discovery, Databases, and Computer-Aided Drug Design, NIDA Research Monograph 134, NIH Publication No. 93-3638, Rapaka, R. S., and Hawks, R. L., eds., U.S. Dept. of Health and Human Services, Rockville, Md. (1993), pages 37-45. For example, an idiotypic antibody to RBM15-MKL1, MKL1-RBM15$_S$, or MKL1-RBM15$_{S+AE}$ fusion protein can be used to co-precipitate fusion protein-bound agents in the purification and characterization of such agents. Harlow, E., et al., Chapter 11 in Antibodies: A Laboratory Manual, Cold Spring Harbor Laboratories, Cold Spring harbor, N.Y. (1988), pages 421-470. Further, an anti-idiotypic antibody to RBM15-MKL1, MKL1-RBM15$_S$, or MKL1-RBM15$_{S+AE}$ can be used to design synthetic RBM15-MKL1, MKL1-RBM15$_S$, or MKL1-RBM15$_{S+AE}$ ligands. Ertl, H., et al., Vaccine 6:80-84 (1988); Wolff, M. E., in Medications Development: Drug Discovery, Databases, and Computer-Aided Drug Design, NIDA Research Monograph 134, NIH Publication No. 93-3638, Rapaka, R. S., and Hawks, R. L., eds., U.S. Dept. of Health and Human Services, Rockville, Md. (1993), pages 46-57. In addition, an anti-idiotypic antibody to the RBM15-MKL1, MKL1-RBM15$_S$, or MKL1-RBM15$_{S+AE}$ fusion proteins, the RBM15-MKL1, MKL1-RBM15$_S$, or MKL1-RBM15$_{S+AE}$ fusion proteins, or a fragment thereof containing the active (ligand binding) site of the fusion protein, can be used to screen an expression library for genes encoding proteins which bind the fusion protein.

Alternatively, cells expressing the RBM15-MKL1, MKL1-RBM15$_S$, or MKL1-RBM15$_{S+AE}$ fusion proteins on their surfaces can be used to screen expression libraries or synthetic combinatorial oligopeptide libraries. Cwirla, S. E., et al., Proc. Natl. Acad. Sci. (USA) 87:6378-6382 (1990); Houghten, R. A., et al., Nature 354:84-86 (1991); Houghten, R. A., et al., in Medications Development: Drug Discovery, Databases, and Computer-Aided Drug Design, NIDA Research Monograph 134, NIH Publication No. 93-3638, Rapaka, R. S., and Hawks, R. L., eds., U.S. Dept. of Health and Human Services, Rockville, Md. (1993), pages 66-74. In particular, cells that have been genetically engineered to express and display the RBM15-MKL1, MKL1-RBM15$_S$, and/or MKL1-RBM15$_{S+AE}$ fusion protein via the use of the nucleic sequences of the invention are preferred in such methods, as host cell lines may be chosen which are devoid of related receptors. Hartig, P. R., in Medications Development: Drug Discovery, Databases, and Computer-Aided Drug Design, NIDA Research Monograph 134, NIH Publication No. 93-3638, Rapaka, R. S., and Hawks, R. L., eds., U.S. Dept. of Health and Human Services, Rockville, Md. (1993), pages 58-65.

The agents screened in the above assay can be, but are not limited to, small molecules, peptides, carbohydrates, or vitamin derivatives. The agents can be selected and screened at random or rationally selected or designed using protein modeling techniques. For random screening, agents such as peptides or carbohydrates are selected at random and are assayed for their ability to bind to the pseudogene peptide. Alternatively, agents may be rationally selected or designed. As used herein, an agent is said to be "rationally selected or designed" when the agent is chosen based on the configuration of the pseudogene peptide. For example, one skilled in the art can readily adapt currently available procedures to generate peptides capable of binding to a specific peptide sequence in order to generate rationally designed antipeptide peptides, see, for example, Hurby et al., "Application of Synthetic Peptides: Antisense Peptides," in Synthetic Peptides: A User's Guide, W. H. Freeman, New York (1992), pp. 289-307; and Kaspczak et al., Biochemistry 28:9230-2938 (1989).

Using the above procedures, the present invention provides agents capable of binding to the the RBM15-MKL1, MKL1-RBM15$_S$, and/or MKL1-RBM15$_{S+AE}$ fusion proteins, produced by a method comprising the steps of (a) contacting said agent with the the RBM15-MKL1, MKL1-RBM15$_S$, and/or MKL1-RBM15$_{S+AE}$ fusion protein, or a fragment thereof, and (b) determining whether said agent binds to the RBM15-MKL1, MKL1-RBM15$_S$, or MKL1-RBM15$_{S+AE}$ fusion protein. Additional step(s) to determine whether such binding is selective for the fusion protein relative to the corresponding unfused RBM15 and MKL1 proteins may also be employed.

The materials used in the above assay methods (both nucleic acid and protein based) are ideally suited for the preparation of a kit. For example, for amplification based detection systems, the invention provides a compartmentalized kit to receive in close confinement, one or more containers which comprises (a) a first container comprising one or more of the amplification primers of the present invention, and (b) one or more other containers comprising one or more of the following: a sample reservoir, amplification reagents, wash reagents, and detection reagents.

For antibody based detection systems, the present invention provides a compartmentalized kit to receive in close confinement, one or more containers which comprises (a) a first container comprising an antibody capable of binding to the RBM15-MKL1, MKL1-RBM15$_S$, or MKL1-RBM15$_{S+AE}$ fusion protein and (b) one or more other containers comprising one or more of the following: wash reagents and reagents capable of detecting the presence of bound antibodies from the first and the second containers.

The invention further provides a kit compartmentalized to receive in close confinement one or more containers which comprises (a) a first container comprising an antibody capable of binding to an epitope which is present in the fusion junction of the RBM15-MKL1, MKL1-RBM15$_S$, or MKL1-RBM15$_{S+AE}$ fusion protein and which is not present in either of the two non-fusion proteins; and (b) one or more other containers comprising one or more of the following: wash reagents and reagents capable of detecting the presence of bound antibodies from the first container.

In detail, a compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers may include a container which will accept the test sample, a container which contains the antibodies or probes used in the assay, containers which contain wash reagents (such as phosphate buffered saline, Tris-buffers, etc.), and containers which contain the reagents used to detect the bound antibody or the hybridized probe. Any detection reagents known in the art can be used including, but not limited to those described supra.

The following examples are offered by way of illustration and not by way of limitation.

EXPERIMENTAL

EXAMPLE 1

Fusion of RNA Recognition Motif-Encoding Gene, RBM15, to the SAP DNA-Binding Domain Gene, MegaKaryoblastic Leukemia-1 (MKL1), in Acute Megakaryoblastic Leukemias with t(1;22)(p13;q13)

Summary

Acute megakaryoblastic leukemia (AMKL) in young children is almost invariably caused by leukemic blasts harboring t(1;22)(p13;q13) (Carroll, A. et al., *Blood* 78:748-752 (1991); Lion, T. et al., *Blood* 79:3325-3330 (1992); Bernstein, J. et al., *Leukemia* 14:216-218 (2000)). Despite its remarkable disease specificity and a lack of knowledge of AMKL pathogenesis (Cripe, L. D. & Hromas, R., *Semin. Hematol.* 35:200-209 (1998)), t(1;22) has yet to be characterized molecularly. Disclosed herein is the identification of the reciprocal fusion transcripts derived from two novel genes, RNA-binding motif protein-15 (RBM15) at chromosome 1p13 and Megakaryoblastic Leukemia-1 (MKL1) at 22q13, as the consequence of t(1;22). RBM15, detected in three isoforms—RBM15$_L$, RBM15$_S$, and RBM15$_{S+AE}$—contains three RNA recognition motifs (RRM) (Burd, C. G. & Dreyfuss, G., *Science* 265:615-621 (1994)) and a Spen paralog and ortholog C-terminal (SPOC) domain (Wiellette, E. L. et al., *Development* 126:5373-5385 (1999)), thus showing significant homology to spen, a homeotic *Drosophila* gene capable of enhancing Ras/MAP kinase signaling (Wiellette, E. L. et al., *Development* 126:5373-5385 (1999); Rebay, I. et al., *Genetics* 154:695-712 (2000); Chen, F. & Rebay, I., *Curr. Biol.* 10:943-946 (2000); Kuang, B. et al., *Development* 127:1517-1529 (2000)). MKL1 contains a SAP (SAF-A/B, Acinus and PIAS) DNA-binding motif (Aravind, L. & Koonin, E. V., *Trends Biochem. Sci.* 25:112-114 (2000)) that in homologous proteins such as SAF-B functions to recruit domains involved in chromatin remodeling, transcriptional control, and pre-mRNA processing to the matrix attachment regions (MAR) of transcriptionally active chromatin, effectively coupling transcription and splicing (Naylor, O. et al., *Nucleic Acids Res.* 26:3542-3549 (1998)). Although both reciprocal fusion transcripts are expressed in AMKL, RBM15-MKL1, from the der(22) chromosome, encodes all putative functional motifs of each gene and is the candidate oncogene of t(1;22), through a mechanism that may involve deregulation of RNA processing and/or Hox and Ras/MAP kinase signaling.

Description

Cloning of chromosomal translocations has led to identification of pathogenically relevant oncogenic fusion transcripts and proteins in specific subsets of acute nonlymphocytic leukemia (ANLL), such as promyelocytic leukemia-retinoic acid receptor alpha fusion gene (PML-RARα) in acute promyelocytic leukemia (FAB-M3 subtype), acute myeloid leukemia 1-eight twenty one fusion gene (AML1-ETO) in ANLL with maturation (FAB-M2), and various mixed lineage leukemia (MLL) gene fusions in acute myelomonocytic and monocytic leukemias (FAB-M4 and -M5) (Melnick, A. & Licht, J. D., *Blood* 93:3167-3215 (1999); Downing, J. R., *Br. J. Haematol.* 106:296-308 (1999); Rowley, J. D., *Semin. Hematol.* 36:59-72 (1999); Look, A. T., *Science* 278:1059-1064 (1997); Faretta, M., Di Croce, L. & Pelicci, P. G., *Sem. Hematol.* 38:42-53 (2001)). Despite these significant advances, little is known about the genetic mechanisms underlying acute leukemias of the megakaryoblastic (platelet precursor) lineage (AMKL, FAB-M7) (Cripe, L. D, infra). Almost invariably, AMKL in non-Down syndrome infants and young children harbor the t(1;22)(p13;q13), in most cases as the sole cytogenetic abnormality(Carroll, A. et al; Lion, T. et al., and Bernstein, J. et al., infra). Phenotypically, AMKL presents de novo (i.e., without a so-called preleukemic stage), with a large leukemia cell mass, and frequent fibrosis of bone marrow and other organs. Progression is usually rapid despite therapy, with a median overall patient survival of only 8 months.

To clone t(1;22), a fluorescence in situ hybridization (FISH)-based positional cloning strategy was used to define the 1p13 and 22q13 breakpoints. Bacterial artificial chromosome (BAC) clones mapping to each chromosomal band were selected using the public and Celera human sequence databases and used pairwise in a series of two-color, two-probe FISH analyses of metaphase chromosomes from t(1; 22)-containing leukemia blasts to identify closely flanking clones. With this strategy, a single chromosome 22 BAC clone, RP5-1042K10, was found that hybridized to both the der(1) and der(22) chromosomes formed by the reciprocal balanced t(1;22) and thus contained the altered 22q13 gene locus. Additional FISH experiments using DNA subfragments of RP5-1042K10 prepared by long-distance PCR (LD-PCR) methods allowed refinement of the chromosome 22 breakpoint to within the most telomeric gene in this clone, and revealed that all cases with t(1;22) possessed genomic breakpoints in a single ~28-kb intron of this gene. The same approach demonstrated the breakpoint on chromosome 1p13 to be encompassed by BAC clone RP 11-260A24. After complete annotation of the sequence by combining entries in the public and Celera databases, the 1p13 breakpoint was sublocalized to within an ~6-kb genomic interval (extending from nucleotide 1,798,871 to 1,804,858 in Celera scaffold GA_x2HTBL4WN8M) using RP11-260A24 LD-PCR subfragments in metaphase FISH. FISH analyses with probes closely flanking the identified breakpoint regions on chromosome 1 and chromosome 22 confirmed the results of our 'split signal' analysis, highlighting both the der(1) and der(22) chromosomes. The breakpoint-spanning clones from each chromosome identified by FISH analysis are RP11-260A24 (chromosome 1) and RP5-1042K10 (chromosome 22). An additional 22q13 BAC, clone RP11-313L7, that spanned the breakpoint was subsequently also identified, the end sequences (accession nos. AQ506839 (Sp6) and AQ537696 (T7)) of which revealed a 65,460 bp overlap with RP5-1042K10 and a 76,650 bp overlap with an additional chromosome 22 clone for this region designated RP4-591N18.

Database searches using the exon sequences flanking the breakpoint-containing intron on chromosome 22 identified an anonymous human brain cDNA library clone (accession no. AB037859). This 3,907-bp cDNA encoded a 2,793-nucleotide ORF, with the putative ATG initiator codon in a context (ATCatgC) adequate to support translational initiation (Kozak, M., *Mammalian Genome* 7:563-574 (1996)). Because RNA blot hybridizations using this clone revealed an approximately 4.5-kb transcript expressed ubiquitously in normal human tissues, additional 5' untranslated sequence was obtained by RACE, resulting in a complete cDNA of 4,447 bp (SEQ ID NO: 13). To denote its involvement in AMKL, this gene was named MKL1 (Megakaryoblastic Leukemia-1, official HUGO Nomenclature Committee designation). Motif searches of the deduced 931-amino acid (aa) MKL1 protein (predicted mass, 98.9 kDa; SEQ ID NO: 14) identified a bipartite nuclear localization signal (BP-NLS) (residues 14-31 of SEQ ID NO: 14; RRSLERART-EDYLKRKIR), a single SAP DNA-binding motif (Aravind, L. & Koonin, E. V., *Trends Biochem. Sci.* 25, 112-114 (2000)) (residues 347-381 of SEQ ID NO: 14), a coiled-coil region (residues 521-563 of SEQ ID NO: 14) that likely mediates protein oligomerization (Lupas, A., *Trends Biochem. Sci.* 21, 375-382 (1996)), and a long C-terminal proline-rich segment (residues 564-811 of SEQ ID NO: 14) similar to proline-rich regions shown to act as transcriptional activators (Mitchell, P. J. & Tjian, R., *Science* 245, 372-378 (1989)). In addition, a short glutamine-rich segment (residues 264-286 of SEQ ID NO: 14; QQQQLFLQLQILN-QQQQQHHNYQ) was found that is highly reminiscent of the more extensive glutamine-rich regions of the MLL acute leukemia-associated transcription factor family, as well as a number of other proteins involved in transcriptional control (Prasad, R. et al., *Oncogene* 15, 549-560 (1997)). Of note, MKL1 showed significant cross-species homology to the product of a *Drosophila* gene of undetermined function, CG12188 (accession no. AAF47681), exhibiting 41% identity (57% similarity) over the initial 161 amino acids of MKL1 and 63% identity (76% similarity) in the SAP domains of the two proteins.

The MKL1 SAP domain shares sequence similarities with SAP domains from (a) THO1—yeast protein Tho1p, which regulates transcriptional elongation by RNA polymerase II; (b) E1B-55 kDa, a transforming adenovirus protein that binds and inhibits p53, and mediates nucleocytoplasmic transport of adenoviral and cellular mRNAs; (c) PIAS1 (protein inhibitor of activated Stat1) which binds and inhibits Stat1, coactivates transcription by various steroid receptors, regulates RNA helicase II function, and has also been reported to bind wt and mutant p53; (d) SAF-B (scaffold attachment factor B), a RRM-containing protein that binds both RNA polymerase II and a subset of serine-/arginine-rich RNA splicing factors; and (e) ACINUS (apoptotic chromatin condensation inducer in the nucleus) which mediates chromatin condensation during programmed cell death (reviewed in Aravind, L. & Koonin, E. V., *Trends Biochem. Sci.* 25, 112-114 (2000)).

With the hypothesis that t(1;22) generates an oncogenic fusion analogous to breakpoint cluster region-Abelson tyrosine kinase fusion gene (BCR-ABL) or the Mixed-lineage leukemia (MLL)fusion genes in leukemias, 5' RACE was performed with total RNA from our leukemia patient samples using MKL1 oligonucleotide primers to identify the 1p13 fusion partner. The obtained sequences corresponded to two anonymous, partially overlapping cDNA clones (accession nos. AK025596, AK022541) from chromosome 1 that were also contained within the approximately 6-kb genomic interval in BAC RP11-260A24 previously demonstrated by FISH to span the 1p13 breakpoint. Due to the presence of three RNA recognition motifs (RRM) encoded by these sequences, the corresponding gene was named RBM15 (RNA-binding motif protein-15, official HUGO Nomenclature Committee name). Using 5' RACE and human placenta cDNA library screening, the complete RBM15 coding sequence was obtained by identification of an ATG initiator codon 132 nucleotides (nts) upstream of the previously deposited sequences and preceded 30 nts by an in-frame TGA stop. Sequencing of RT-PCR products obtained with RBM15-specific primers from normal leukocyte mRNA demonstrated three transcripts that share an identical 2,863-bp 5' coding sequence, differing only in their extreme 3' coding portions due to alternative exon usage (FIG. 1)

RBM15 contains three RRM motifs and a BP-NLS in its C-terminus, and is highly homologous to *Drosophila* gene product GH11110 (accession no. AF 145664) (40% identity, 56% similarity with the RRM-containing region of RBM15 from residues 170-529; 39% identity, 54% similarity with the RBM15 C-terminus from residues 714-954; percent identity determined using BLAST 2.1.3 (Altschul, S. F. et al., *Nucleic Acids Res.* 25: 3389 (1997)) with default parameters selected). These regions of RBM15 and *Drosophila* GH11110 (also previously referred to as *D. melanogaster* Short spen-like protein-2, DmSSLP2) (Wiellette, E. L. et al., *Development* 126, 5373-5385 (1999)) are closely related to *Drosophila* spen (split ends)—an RRM protein that modulates Hox homeotic function (e.g., cooperating with *Antennapedia* to suppress head-like development in the thoracic region), and regulates neuronal cell fate and axon extension by enhancing Ras/MAP kinase signaling (Wiellette, E. L. et al., *Development* 126, 5373-5385 (1999); Rebay, I. et al., *Genetics* 154, 695-712 (2000); Chen, F. & Rebay, I., *Curr. Biol.* 10, 943-946 (2000); Kuang, B. et al., *Development* 127, 1517-1529 (2000)). Thus, the RBM15 C-terminus also contains a so-called SPOC (Spen paralog and ortholog C-terminal) domain, a 165-aa conserved motif of undetermined function found in Spen and Spen-like proteins (Wiellette, E. L. et al., *Development* 126, 5373-5385 (1999)) including the mammalian spen ortholog, MINT (Msx2-interacting nuclear target), which binds homeoprotein Msx2 (Hox 8) and coregulates osteoblast gene expression during craniofacial development (Newberry, E. P. et al., *Biochemistry* 38, 10678-10690 (1999)).

In t(1;22)-positive AMKL blasts, RT-PCR demonstrated expression of both reciprocal fusion transcripts, RBM15-MKL1 and MKL1-RBM15. RT-PCR reactions using RBM15 sense (RBM15(S)-2746F) and MKL1 antisense (MKL1-204R) primers amplify a single 268-bp RBM15-MKL1 product in all patients (nucleotides 2866 to 3133 of SEQ ID NO: 1). Using MKL1 sense (MKL1-F) and RBM15 antisense (RBM15(S)-2930R), corresponding to sequences of the 3' most exon unique to RBM15$_S$ and RBM15$_{S+AE}$) primers, two reciprocal MKL1-RBM15 fusion transcripts are detected, one (251 bp; nucleotides 411 to 661 of SEQ ID NO: 3) containing the 3' sequences from RBM15$_S$ and the other (362 bp; nucleotides 411 to 772 of SEQ ID NO: 5) with 3' sequences found in RBM15$_{S+AE}$. No MKL1-RBM15 RT-PCR products were obtained using MKL1-F and an antisense primer specific for RBM15$_L$ (RBM15(L)-1636R) in any patients examined.

The predicted RBM15-MKL1 chimeric protein encoded on the der(22) contains all putative functional motifs of each normal protein (FIG. 1). Frequent duplication of der(1) in t(1;22)-containing blasts has led to speculation that this abnormal chromosome likely encodes the oncogenic AMKL fusion protein(s) (Carroll, A. et al.; Lion, T. et al., Bernstein, J. et al., infra.); however, a functional role for MKL1-RBM15$_S$ and MKL1-RBM15$_{S+AE}$ in leukemogenesis is unclear given they encode predicted products of only 17 and 25 aa, respectively.

The SAP motif mediates DNA binding of proteins to the AT-rich matrix attachment regions (MAR) associated with transcriptionally active chromatin (Aravind, L. & Koonin, E. V., *Trends Biochem. Sci.* 25, 112-114 (2000)). SAP proteins include SAF-B (Chen, F. & Rebay, I., *Curr. Biol.* 10, 943-946 (2000)), involved in RNA processing; Acinus (Sahara, S. et al., *Nature* 401, 168-173 (1999)), which induces chromatin condensation; and PIAS proteins (Valdez, B. C. et al., *Biochem. Biophys. Res. Commun.* 234, 335-340 (1997); Chung, C. D. et al., *Science* 278, 1803-1805 (1997); Kotaja, N. et al., *Mol. Endocrinol.* 14, 1986-2000 (2000)) that bind RNA helicase II, inhibit STAT signal transduction, and modulate steroid receptor-dependent transcription. Thus, the SAP targets a diverse set of functional domains to MAR sequences, coupling transcription and splicing. In addition to modulating homeotic protein functions (and in the case of spen, enhancing Ras/MAP kinase signals), Spen family proteins like MINT can bind specific DNA sequences via their RRM domains, an RRM function seen also in other transcriptional regulators such as sea urchin SSAP (Stage-specific activator protein) (DeAngelo, D. J. et al., *Mol. Cell. Biol.* 15, 1254-1264 (1995); DeFalco, J. & Childs, G., *Proc. Natl. Acad. Sci.* 93, 5802-5807 (1996)) and hTAFII68, an RNA/ssDNA-binding protein homologous to pro-oncoproteins TLS/FUS and EWS (Bertolotti, A. et al., *EMBO J* 15, 5022-5031 (1996); Bertolotti, A. et al., *Oncogene* 18, 8000-8010 (1999)). In RBM15-MKL1, the MKL1 SAP motif would be expected to relocalize the RRM domains of RBM15 aberrantly to sites of transcriptionally active chromatin, targeting genes critical for the normal proliferation or differentiation of megakaryoblasts.

Methods

Clinical Cases

Leukemia specimens with histopathological and immunophenotypic features typical of AMKL were studied from five infants and young children. All cases contained t(1;22)(p13;q13) with the exception of patient 2, whose blasts possessed a complex t(1;6;22)(p13;p12;q13). All five specimens were shown to contain rearrangement of RBM15 and MKL1 by RT-PCR and/or FISH analysis.

Fluorescence In Situ Hybridization (FISH)

DNA was labeled by nick translation with digoxigenin-11-dUTP and/or biotin-16-dUTP (Roche Molecular Biochemicals). Labeled probes were combined with sheared human DNA and hybridized to fixed interphase nuclei and metaphase cells in 50% formamide, 10% dextran sulfate and 2×SSC at 37° C. and subsequently washed in a 50% formamide, 2×SSC solution at 37° C. Hybridization signals were detected with fluorescein-labeled anti-digoxigenin (Ventana Medical Systems) for digoxigenin-labeled probes and Texas red-avidin for biotinylated probes. Chromosomes and nuclei were stained with 4,6-diamidino-2-phenylindole (DAPI) prior to analysis.

Rapid Amplification of cDNA Ends (RACE) and DNA Sequencing

Total RNA was extracted from t(1;22)-positive frozen AMKL specimens using RNA STAT-60 (Tel-Test, Inc.). Approximately 0.2 μg RNA was used for 5' RACE experiments that identified RBM15 as the chromosome 1p13 partner gene of MKL1. Reverse transcription was performed with primer MKL1-294R (SEQ ID NO: 15). After purification and tailing of the cDNA, PCR was performed with an oligo-dT anchor primer and MKL1 reverse primer MKL1-73R (SEQ ID NO: 16), using temperature cycling conditions recommended by the manufacturer (Roche Molecular Biochemicals) and a Thermal Cycle Model 2400 (Perkin-Elmer Cetus). Twenty microliters of PCR product were separated on a 2% agarose gel, and specific bands were purified (Qiaquick gel extraction kit, Qiagen, Inc.) and sequenced using MKL1 reverse primer MKL1-59R (SEQ ID NO: 17).

RT-PCR of RBM15-MKL1 and MKL1-RBM15 Fusion Transcripts

For RBM15-MKL1 detection, 1 μg of total RNA was reverse transcribed using primer MKL1-294R (SEQ ID NO: 15). PCR was performed using primers RBM15(S)-2746F (SEQ ID NO: 18) and MKL1-204R (SEQ ID NO: 19) and 35 cycles (94° C. for 15 s, 60° C. for 30 s, 72° C. for 30 s). Primer pair MKL1-F (SEQ ID NO: 20) and MKL1-204R, designed to amplify a portion of the ubiquitously expressed MKL1, were included in control experiments to verify RNA quality and RT-PCR technique. PCR products were gel purified, then cycle sequenced using primers RBM15(S)-2746F and MKL1-204R. For detection of MKL1-RBM15 fusion transcripts, reverse transcription was done using an oligo-dT primer and PCR performed with primers MKL1-F (SEQ ID NO: 20) and RBM15(S)-2930R (SEQ ID NO: 21) (to identify MKL1-RBM15$_S$ and MKL1-RBM15$_{S+AE}$) or MKL1-F (SEQ ID NO: 20) and RBM15(L)-1636R (SEQ ID NO: 22) (to detect MKL1-RBM15$_L$). Amplification of normal RBM15 sequences for quality control was performed with primer pairs RBM15(S)-2746F (SEQ ID NO: 18) and RBM15(S)-2930R (SEQ ID NO: 21) or RBM15(L)-1636R (SEQ ID NO: 22).

Northern Blot Analysis

Normal human peripheral blood leukocyte total RNA was extracted (RNEasy kit, Qiagen), then treated with RNase-free DNase for 15 m at room temp. This RNA was reverse transcribed and used as the template in PCR amplifications (35 cycles: 94° C. for 10 s, 62° C. for 10 s, 68° C. for 1 m) to generate cDNA fragments corresponding to probes a-d (FIG. 1). The following PCR primer pairs were used: RBM15 probe a (433 bp), RBM15-1118F (SEQ ID NO: 23) and RBM15-1551R (SEQ ID NO: 24); RBM15 probe b (318 bp), RBM15-2831F (SEQ ID NO: 25) and RBM15-3149R (SEQ ID NO: 26); RBM15 probe c (388 bp), RBM15-1616F (SEQ ID NO: 27) and RBM15-2004R (SEQ ID NO: 28); MKL1 probe d (449 bp), MKL1-155F (SEQ ID NO: 29) and MKL1-294R (SEQ ID NO: 15). Multiple tissue Northern blots (Clontech) containing approximately 2 μg of poly(A)+ RNA prepared from normal human tissues were hybridized at 68° C. for 2 h in ExpressHyb buffer (Clontech) using these RBM15 and MKL1 cDNA probes or a β-actin probe supplied by the manufacturer. Filters were autoradiographed at −80° C. with one intensifying screen for 3 d (probes a, c and d), 1 d (probe b) or 1 h (for β-actin).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the following embodiments.

The invention claimed is:

1. An isolated nucleotide molecule comprising a nucleotide sequence selected from the group consisting of:
   (a) a nucleotide sequence encoding the fusion protein having the amino acid sequence set forth in SEQ ID NO: 2; and
   (b) the nucleotide sequence set forth in SEQ ID NO: 1.

* * * * *

UNITED STATES PATENT AND TRADEMARK OFFICE
CERTIFICATE OF CORRECTION

PATENT NO. : 7,329,744 B2 Page 1 of 1
APPLICATION NO. : 10/475917
DATED : February 12, 2008
INVENTOR(S) : Morris et al.

It is certified that error appears in the above-identified patent and that said Letters Patent is hereby corrected as shown below:

Title Page:

Item (54): "MEGAKARYOBLASTOC" should read --MEGAKARYOBLASTIC--

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,329,744 B2  Page 1 of 1
APPLICATION NO. : 10/475917
DATED : February 12, 2008
INVENTOR(S) : Morris et al.

It is certified that error appears in the above-identified patent and that said Letters Patent is hereby corrected as shown below:

<u>Title Page, Item (54) and Column 1, line 2:</u> "MEGAKARYOBLASTOC" should read --MEGAKARYOBLASTIC--

This certificate supersedes the Certificate of Correction issued February 17, 2009.

Signed and Sealed this

Seventeenth Day of March, 2009

JOHN DOLL
*Acting Director of the United States Patent and Trademark Office*

SEQUENCE LISTING

<160> NUMBER OF SEQ ID NOS: 29

<210> SEQ ID NO 1
<211> LENGTH: 6836
<212> TYPE: DNA
<213> ORGANISM: Homo sapiens
<220> FEATURE:
<221> NAME/KEY: CDS
<222> LOCATION: (84)..(5732)

<400> SEQUENCE: 1

```
ggcgccttcc tggagcgcgg ggagatgtaa agatagacaa ataattttcc caatgagact      60
gtagaagaga gagcaattgg cca atg agg act gcg ggg cgg gac cct gtg ccg     113
                         Met Arg Thr Ala Gly Arg Asp Pro Val Pro
                          1               5                  10 cgg cgg agt cca aga tgg cgg cgt gcg gtt ccg ctg tgt gaa acg agc       161
Arg Arg Ser Pro Arg Trp Arg Arg Ala Val Pro Leu Cys Glu Thr Ser
             15                  20                  25 gcg ggg cgg cgg gtt act cag ctc cgc gga gac gac ctc cga cga ccc       209
Ala Gly Arg Arg Val Thr Gln Leu Arg Gly Asp Asp Leu Arg Arg Pro
         30                  35                  40 gca aca atg aag gga aaa gag cgc tcg cca gtg aag gcc aaa cgc tcc       257
Ala Thr Met Lys Gly Lys Glu Arg Ser Pro Val Lys Ala Lys Arg Ser
     45                  50                  55 cgt ggt ggt gag gac tcg act tcc cgc ggt gag cgg agc aag aag tta       305
Arg Gly Gly Glu Asp Ser Thr Ser Arg Gly Glu Arg Ser Lys Lys Leu
 60                  65                  70 ggg ggc tct ggt ggc agc aat ggg agc agc agc gga aag acc gat agc       353
Gly Gly Ser Gly Gly Ser Asn Gly Ser Ser Ser Gly Lys Thr Asp Ser
 75                  80                  85                  90 ggc ggt ggg tcg cgg cgg agt ctc ctc ctg gac aag tcc agc agt cga       401
Gly Gly Gly Ser Arg Arg Ser Leu Leu Leu Asp Lys Ser Ser Ser Arg
                 95                 100                 105 ggt ggc agc cgc gag tat gat acc ggt ggg ggc agc tcc agt agc cgc       449
Gly Gly Ser Arg Glu Tyr Asp Thr Gly Gly Gly Ser Ser Ser Ser Arg
             110                 115                 120 ttg cat agt tat agc tcc ccg agc acc aaa aat tct tcg ggc ggg ggc       497
Leu His Ser Tyr Ser Ser Pro Ser Thr Lys Asn Ser Ser Gly Gly Gly
         125                 130                 135 gag tcg cgc agc agc tcc cgg ggt gga ggc ggg gag tca cgt tcc tct       545
Glu Ser Arg Ser Ser Ser Arg Gly Gly Gly Gly Glu Ser Arg Ser Ser
     140                 145                 150 ggg gcc gcc tcc tca gct ccc ggc ggc ggg gac ggc gcg gaa tac aag       593
Gly Ala Ala Ser Ser Ala Pro Gly Gly Gly Asp Gly Ala Glu Tyr Lys
155                 160                 165                 170 act ctg aag ata agc gag ttg ggg tcc cag ctt agt gac gaa gcg gtg       641
Thr Leu Lys Ile Ser Glu Leu Gly Ser Gln Leu Ser Asp Glu Ala Val
                 175                 180                 185 gag gac ggc ctg ttt cat gag ttc aaa cgc ttc ggt gat gta agt gtg       689
Glu Asp Gly Leu Phe His Glu Phe Lys Arg Phe Gly Asp Val Ser Val
             190                 195                 200 aaa atc agt cat ctg tcg ggt tct ggc agc ggg gat gag cgg gta gcc       737
Lys Ile Ser His Leu Ser Gly Ser Gly Ser Gly Asp Glu Arg Val Ala
         205                 210                 215 ttt gtg aac ttc cgg cgg cca gag gac gcg cgg gcg gcc aag cat gcc       785
Phe Val Asn Phe Arg Arg Pro Glu Asp Ala Arg Ala Ala Lys His Ala
     220                 225                 230 aga ggc cgc ctg gtg ctc tat gac cgg cct ctg aag ata gaa gct gtg       833
Arg Gly Arg Leu Val Leu Tyr Asp Arg Pro Leu Lys Ile Glu Ala Val
```

-continued

| | | | | |
|---|---|---|---|---|
| 235 | 240 | 245 | 250 | |
| tat gtg agc cgg cgc cgc agc cgc tcc cct tta gac aaa gat act tat<br>Tyr Val Ser Arg Arg Arg Ser Arg Ser Pro Leu Asp Lys Asp Thr Tyr<br>255 260 265 | | | | 881 |
| cct cca tca gcc agt gtg gtc ggg gcc tct gta ggt ggt cac cgg cac<br>Pro Pro Ser Ala Ser Val Val Gly Ala Ser Val Gly Gly His Arg His<br>270 275 280 | | | | 929 |
| ccc cct gga ggt ggt gga ggc cag aga tca ctt tcc cct ggt ggc gct<br>Pro Pro Gly Gly Gly Gly Gly Gln Arg Ser Leu Ser Pro Gly Gly Ala<br>285 290 295 | | | | 977 |
| gct ttg gga tac aga gac tac cgg ctg cag cag ttg gct ctt ggc cgc<br>Ala Leu Gly Tyr Arg Asp Tyr Arg Leu Gln Gln Leu Ala Leu Gly Arg<br>300 305 310 | | | | 1025 |
| ctg ccc cct cca cct ccg cca cca ttg cct cga gac ctg gag aga gaa<br>Leu Pro Pro Pro Pro Pro Pro Pro Leu Pro Arg Asp Leu Glu Arg Glu<br>315 320 325 330 | | | | 1073 |
| aga gac tac ccg ttc tat gag aga gtg cgc cct gca tac agt ctt gag<br>Arg Asp Tyr Pro Phe Tyr Glu Arg Val Arg Pro Ala Tyr Ser Leu Glu<br>335 340 345 | | | | 1121 |
| cca agg gtg gga gct gga gca ggt gct gct cct ttc aga gaa gtg gat<br>Pro Arg Val Gly Ala Gly Ala Gly Ala Ala Pro Phe Arg Glu Val Asp<br>350 355 360 | | | | 1169 |
| gag att tca ccc gag gat gat cag cga gct aac cgg acg ctc ttc ttg<br>Glu Ile Ser Pro Glu Asp Asp Gln Arg Ala Asn Arg Thr Leu Phe Leu<br>365 370 375 | | | | 1217 |
| ggc aac cta gac atc act gta acg gag agt gat tta aga agg gcg ttt<br>Gly Asn Leu Asp Ile Thr Val Thr Glu Ser Asp Leu Arg Arg Ala Phe<br>380 385 390 | | | | 1265 |
| gat cgc ttt gga gtc atc aca gaa gta gat atc aag agg cct tct cgc<br>Asp Arg Phe Gly Val Ile Thr Glu Val Asp Ile Lys Arg Pro Ser Arg<br>395 400 405 410 | | | | 1313 |
| ggc cag act agt act tac ggc ttt ctc aaa ttt gag aac tta gat atg<br>Gly Gln Thr Ser Thr Tyr Gly Phe Leu Lys Phe Glu Asn Leu Asp Met<br>415 420 425 | | | | 1361 |
| tct cac cgg gcc aaa tta gca atg tct ggc aaa att ata att cgg aat<br>Ser His Arg Ala Lys Leu Ala Met Ser Gly Lys Ile Ile Ile Arg Asn<br>430 435 440 | | | | 1409 |
| cct atc aaa att ggt tat ggt aaa gct aca ccc acc acc cgc ctc tgg<br>Pro Ile Lys Ile Gly Tyr Gly Lys Ala Thr Pro Thr Thr Arg Leu Trp<br>445 450 455 | | | | 1457 |
| gtg gga ggc ctg gga cct tgg gtt cct ctt gct gcc ctg gca cga gaa<br>Val Gly Gly Leu Gly Pro Trp Val Pro Leu Ala Ala Leu Ala Arg Glu<br>460 465 470 | | | | 1505 |
| ttt gat cga ttt ggc acc ata cgc acc ata gac tac cga aaa ggt gat<br>Phe Asp Arg Phe Gly Thr Ile Arg Thr Ile Asp Tyr Arg Lys Gly Asp<br>475 480 485 490 | | | | 1553 |
| agt tgg gca tat atc cag tat gaa agc ctg gat gca gcg cat gct gcc<br>Ser Trp Ala Tyr Ile Gln Tyr Glu Ser Leu Asp Ala Ala His Ala Ala<br>495 500 505 | | | | 1601 |
| tgg acc cat atg cgg ggc ttc cca ctt ggt ggc cca gat cga cgc ctt<br>Trp Thr His Met Arg Gly Phe Pro Leu Gly Gly Pro Asp Arg Arg Leu<br>510 515 520 | | | | 1649 |
| aga gta gac ttt gcc gac acc gaa cat cgt tac cag cag cag tat ctg<br>Arg Val Asp Phe Ala Asp Thr Glu His Arg Tyr Gln Gln Gln Tyr Leu<br>525 530 535 | | | | 1697 |
| cag cct ctg ccc ttg act cat tat gag ctg gtg aca gat gct ttt gga<br>Gln Pro Leu Pro Leu Thr His Tyr Glu Leu Val Thr Asp Ala Phe Gly<br>540 545 550 | | | | 1745 |
| cat cgg gca cca gac cct ttg agg ggt gct cgg gat agg aca cca ccc | | | | 1793 |

```
His Arg Ala Pro Asp Pro Leu Arg Gly Ala Arg Asp Arg Thr Pro Pro
555                 560                 565                 570 tta cta tac aga gat cgt gat agg gac ctt tat cct gac tct gat tgg         1841
Leu Leu Tyr Arg Asp Arg Asp Arg Asp Leu Tyr Pro Asp Ser Asp Trp
                575                 580                 585 gtg cca ccc cca ccc cca gtc cga gaa cgc agc act cgg act gca gct         1889
Val Pro Pro Pro Pro Pro Val Arg Glu Arg Ser Thr Arg Thr Ala Ala
                590                 595                 600 act tct gtg cct gct tat gag cca ctg gat agc cta gat cgc agg cgg         1937
Thr Ser Val Pro Ala Tyr Glu Pro Leu Asp Ser Leu Asp Arg Arg Arg
            605                 610                 615 gat ggt tgg tcc ttg gac cgg gac aga ggt gat cga gat ctg ccc agc         1985
Asp Gly Trp Ser Leu Asp Arg Asp Arg Gly Asp Arg Asp Leu Pro Ser
        620                 625                 630 agc aga gac cag cct agg aag cga agg ctg cct gag gag agt gga gga         2033
Ser Arg Asp Gln Pro Arg Lys Arg Arg Leu Pro Glu Glu Ser Gly Gly
635                 640                 645                 650 cgt cat ctg gat agg tct cct gag agt gac cgc cca cga aaa cgt cac         2081
Arg His Leu Asp Arg Ser Pro Glu Ser Asp Arg Pro Arg Lys Arg His
                655                 660                 665 tgc gct cct tct cct gac cgc agt cca gaa ttg agc agt agc cgg gat         2129
Cys Ala Pro Ser Pro Asp Arg Ser Pro Glu Leu Ser Ser Ser Arg Asp
                670                 675                 680 cgt tac aac agc gac aat gat cga tct tcc cgt ctt ctc ttg gaa agg         2177
Arg Tyr Asn Ser Asp Asn Asp Arg Ser Ser Arg Leu Leu Leu Glu Arg
            685                 690                 695 ccc tct cca atc aga gac gga cga ggt agt ttg gag aag agc cag ggt         2225
Pro Ser Pro Ile Arg Asp Gly Arg Gly Ser Leu Glu Lys Ser Gln Gly
700                 705                 710 gac aag cga gac cgt aaa aac tct gca tca gct gaa cga gat agg aag         2273
Asp Lys Arg Asp Arg Lys Asn Ser Ala Ser Ala Glu Arg Asp Arg Lys
715                 720                 725                 730 cac cgg aca act gct ccc act gag gga aaa agc cct ctg aaa aaa gaa         2321
His Arg Thr Thr Ala Pro Thr Glu Gly Lys Ser Pro Leu Lys Lys Glu
                735                 740                 745 gac cgc tct gat ggg agt gca cct agc acc agc act gct tcc tcc aag         2369
Asp Arg Ser Asp Gly Ser Ala Pro Ser Thr Ser Thr Ala Ser Ser Lys
                750                 755                 760 ctg aag tcc ccg tcc cag aaa cag gat ggg ggg aca gcc cct gtg gca         2417
Leu Lys Ser Pro Ser Gln Lys Gln Asp Gly Gly Thr Ala Pro Val Ala
            765                 770                 775 tca gcc tct ccc aaa ctc tgt ttg gcc tgg cag ggc atg ctt cta ctg         2465
Ser Ala Ser Pro Lys Leu Cys Leu Ala Trp Gln Gly Met Leu Leu Leu
780                 785                 790 aag aac agc aac ttt cct tcc aac atg cat ctg ttg cag ggt gac ctc         2513
Lys Asn Ser Asn Phe Pro Ser Asn Met His Leu Leu Gln Gly Asp Leu
795                 800                 805                 810 caa gtg gct agt agt ctt ctt gtg gag ggt tca act gga ggc aaa gtg         2561
Gln Val Ala Ser Ser Leu Leu Val Glu Gly Ser Thr Gly Gly Lys Val
                815                 820                 825 gcc cag ctc aag atc act cag cgt ctc cgt ttg gac cag ccc aag ttg         2609
Ala Gln Leu Lys Ile Thr Gln Arg Leu Arg Leu Asp Gln Pro Lys Leu
                830                 835                 840 gat gaa gta act cga cgc atc aaa gta gca ggg ccc aat ggt tat gcc         2657
Asp Glu Val Thr Arg Arg Ile Lys Val Ala Gly Pro Asn Gly Tyr Ala
            845                 850                 855 att ctt ttg gct gtg cct gga agt tct gac agc cgg tcc tcc tct tcc         2705
Ile Leu Leu Ala Val Pro Gly Ser Ser Asp Ser Arg Ser Ser Ser Ser
860                 865                 870
```

-continued

| | | |
|---|---|---|
| tca gct gca tca gac act gcc act tct act cag agg cca ctt agg aac<br>Ser Ala Ala Ser Asp Thr Ala Thr Ser Thr Gln Arg Pro Leu Arg Asn<br>875                      880                    885                  890 | | 2753 |
| ctt gtg tcc tat tta aag caa aag cag gca gcc ggg gtg atc agc ctc<br>Leu Val Ser Tyr Leu Lys Gln Lys Gln Ala Ala Gly Val Ile Ser Leu<br>                  895                    900                  905 | | 2801 |
| cct gtg ggg ggc aac aaa gac aag gaa aac acc ggg gtc ctt cat gcc<br>Pro Val Gly Gly Asn Lys Asp Lys Glu Asn Thr Gly Val Leu His Ala<br>        910                    915                  920 | | 2849 |
| ttc cca cct tgt gag ttc tcc cag cag ttc ctg gat tcc cct gcc aag<br>Phe Pro Pro Cys Glu Phe Ser Gln Gln Phe Leu Asp Ser Pro Ala Lys<br>925                      930                    935 | | 2897 |
| gca ctg gcc aaa tct gaa gaa gat tac ctg gtc atg atc att gtc cgt<br>Ala Leu Ala Lys Ser Glu Glu Asp Tyr Leu Val Met Ile Ile Val Arg<br>        940                    945                  950 | | 2945 |
| gct ttg aaa agt cca gcc gca ttt cat gag cag aga agg agc ttg gag<br>Ala Leu Lys Ser Pro Ala Ala Phe His Glu Gln Arg Arg Ser Leu Glu<br>955                      960                    965                  970 | | 2993 |
| cgg gcc agg aca gag gac tat ctc aaa cgg aag att cgt tcc cgg ccg<br>Arg Ala Arg Thr Glu Asp Tyr Leu Lys Arg Lys Ile Arg Ser Arg Pro<br>                  975                    980                  985 | | 3041 |
| gag aga tcg gag ctg gtc agg atg cac att ttg gaa gag acc tcg gct<br>Glu Arg Ser Glu Leu Val Arg Met His Ile Leu Glu Glu Thr Ser Ala<br>        990                    995                  1000 | | 3089 |
| gag cca tcc ctc cag gcc aag cag ctg aag ctg aag aga gcc aga<br>Glu Pro Ser Leu Gln Ala Lys Gln Leu Lys Leu Lys Arg Ala Arg<br>        1005                    1010                  1015 | | 3134 |
| cta gcc gat gac ctc aat gag aag att gca cag agg cct ggc ccc<br>Leu Ala Asp Asp Leu Asn Glu Lys Ile Ala Gln Arg Pro Gly Pro<br>        1020                    1025                  1030 | | 3179 |
| atg gag ctg gtg gag aag aac atc ctt cct gtt gag tcc agc ctg<br>Met Glu Leu Val Glu Lys Asn Ile Leu Pro Val Glu Ser Ser Leu<br>        1035                    1040                  1045 | | 3224 |
| aag gaa gcc atc att gtg ggc cag gtg aac tat ccc aaa gta gca<br>Lys Glu Ala Ile Ile Val Gly Gln Val Asn Tyr Pro Lys Val Ala<br>        1050                    1055                  1060 | | 3269 |
| gac agc tct tcc ttc gat gag gac agc agc gat gcc tta tcc ccc<br>Asp Ser Ser Ser Phe Asp Glu Asp Ser Ser Asp Ala Leu Ser Pro<br>        1065                    1070                  1075 | | 3314 |
| gag cag cct gcc agc cat gag tcc cag ggt tct gtg ccg tca ccc<br>Glu Gln Pro Ala Ser His Glu Ser Gln Gly Ser Val Pro Ser Pro<br>        1080                    1085                  1090 | | 3359 |
| ctg gag gcc cga gtc agc gaa cca ctg ctc agt gcc acc tct gca<br>Leu Glu Ala Arg Val Ser Glu Pro Leu Leu Ser Ala Thr Ser Ala<br>        1095                    1100                  1105 | | 3404 |
| tcc ccc acc cag gtt gtg tct caa ctt ccg atg ggc cgg gat tcc<br>Ser Pro Thr Gln Val Val Ser Gln Leu Pro Met Gly Arg Asp Ser<br>        1110                    1115                  1120 | | 3449 |
| aga gaa atg ctt ttc ctg gca gag cag cct cct ctg cct ccc cca<br>Arg Glu Met Leu Phe Leu Ala Glu Gln Pro Pro Leu Pro Pro Pro<br>        1125                    1130                  1135 | | 3494 |
| cct ctg ctg cct ccc agc ctc acc aat gga acc act atc ccc act<br>Pro Leu Leu Pro Pro Ser Leu Thr Asn Gly Thr Thr Ile Pro Thr<br>        1140                    1145                  1150 | | 3539 |
| gcc aag tcc acc ccc aca ctc att aag caa agc caa ccc aag tct<br>Ala Lys Ser Thr Pro Thr Leu Ile Lys Gln Ser Gln Pro Lys Ser<br>        1155                    1160                  1165 | | 3584 |
| gcc agt gag aag tca cag cgc agc aag aag gcc aag gag ctg aag<br>Ala Ser Glu Lys Ser Gln Arg Ser Lys Lys Ala Lys Glu Leu Lys<br>        1170                    1175                  1180 | | 3629 |

-continued

```
cca aag gtg aag aag ctc aag tac cac cag tac atc ccc ccg gac    3674
Pro Lys Val Lys Lys Leu Lys Tyr His Gln Tyr Ile Pro Pro Asp
        1185                1190                1195 cag aag cag gac agg ggg gca ccc ccc atg gac tca tcc tac gcc    3719
Gln Lys Gln Asp Arg Gly Ala Pro Pro Met Asp Ser Ser Tyr Ala
        1200                1205                1210 aag atc ctg cag cag cag cag ctc ttc ctc cag ctg cag atc ctc    3764
Lys Ile Leu Gln Gln Gln Gln Leu Phe Leu Gln Leu Gln Ile Leu
        1215                1220                1225 aac cag cag cag cag cag cac cac aac tac cag gcc atc ctg cct    3809
Asn Gln Gln Gln Gln Gln His His Asn Tyr Gln Ala Ile Leu Pro
        1230                1235                1240 gcc ccg cca aag tca gca ggc gag gcc ctg gga agc agc ggg acc    3854
Ala Pro Pro Lys Ser Ala Gly Glu Ala Leu Gly Ser Ser Gly Thr
        1245                1250                1255 ccc cca gta cgc agc ctc tcc act acc aat agc agc tcc agc tcg    3899
Pro Pro Val Arg Ser Leu Ser Thr Thr Asn Ser Ser Ser Ser Ser
        1260                1265                1270 ggc gcc cct ggg ccc tgt ggg ctg gca cgt cag aac agc acc tca    3944
Gly Ala Pro Gly Pro Cys Gly Leu Ala Arg Gln Asn Ser Thr Ser
        1275                1280                1285 ctg act ggc aag ccg gga gcc ctg ccg gcc aac ctg gac gac atg    3989
Leu Thr Gly Lys Pro Gly Ala Leu Pro Ala Asn Leu Asp Asp Met
        1290                1295                1300 aag gtg gca gag ctg aag cag gag ctg aag ttg cga tca ctg cct    4034
Lys Val Ala Glu Leu Lys Gln Glu Leu Lys Leu Arg Ser Leu Pro
        1305                1310                1315 gtc tcg ggc acc aaa act gag ctg att gag cgc ctt cga gcc tat    4079
Val Ser Gly Thr Lys Thr Glu Leu Ile Glu Arg Leu Arg Ala Tyr
        1320                1325                1330 caa gac caa atc agc cct gtg cca gga gcc ccc aag gcc cct gcc    4124
Gln Asp Gln Ile Ser Pro Val Pro Gly Ala Pro Lys Ala Pro Ala
        1335                1340                1345 gcc acc tct atc ctg cac aag gct ggc gag gtg gtg gta gcc ttc    4169
Ala Thr Ser Ile Leu His Lys Ala Gly Glu Val Val Val Ala Phe
        1350                1355                1360 cca gcg gcc cgg ctg agc acg ggg cca gcc ctg gtg gca gca ggc    4214
Pro Ala Ala Arg Leu Ser Thr Gly Pro Ala Leu Val Ala Ala Gly
        1365                1370                1375 ctg gct cca gct gag gtg gtg gtg gcc acg gtg gcc agc agt ggg    4259
Leu Ala Pro Ala Glu Val Val Val Ala Thr Val Ala Ser Ser Gly
        1380                1385                1390 gtg gtg aag ttt ggc agc acg ggc tcc acg ccc ccc gtg tct ccc    4304
Val Val Lys Phe Gly Ser Thr Gly Ser Thr Pro Pro Val Ser Pro
        1395                1400                1405 acc ccc tcg gag cgc tca ctg ctc agc acg ggc gat gaa aac tcc    4349
Thr Pro Ser Glu Arg Ser Leu Leu Ser Thr Gly Asp Glu Asn Ser
        1410                1415                1420 acc ccc ggg gac acc ttt ggt gag atg gtg aca tca cct ctg acg    4394
Thr Pro Gly Asp Thr Phe Gly Glu Met Val Thr Ser Pro Leu Thr
        1425                1430                1435 cag ctg acc ctg cag gcc tcg cca ctg cag atc ctc gtg aag gag    4439
Gln Leu Thr Leu Gln Ala Ser Pro Leu Gln Ile Leu Val Lys Glu
        1440                1445                1450 gag ggc ccc cgg gcc ggg tcc tgt tgc ctg agc cct ggg ggg cgg    4484
Glu Gly Pro Arg Ala Gly Ser Cys Cys Leu Ser Pro Gly Gly Arg
        1455                1460                1465 gcg gag cta gag ggg cgc gac aag gac cag atg ctg cag gag aaa    4529
Ala Glu Leu Glu Gly Arg Asp Lys Asp Gln Met Leu Gln Glu Lys
```

-continued

| | | | | | | | | | | | | |
|---|---|---|---|---|---|---|---|---|---|---|---|---|
| | | 1470 | | | | 1475 | | | | 1480 | | |
| gac | aag | cag | atc | gag | gcg | ctg | acg | cgc | atg | ctc | cgg | cag | aag | cag | 4574 |
| Asp | Lys | Gln | Ile | Glu | Ala | Leu | Thr | Arg | Met | Leu | Arg | Gln | Lys | Gln | |
| | | 1485 | | | | 1490 | | | | 1495 | | |
| cag | ctg | gtg | gag | cgg | ctc | aag | ctg | cag | ctg | gag | cag | gag | aag | cga | 4619 |
| Gln | Leu | Val | Glu | Arg | Leu | Lys | Leu | Gln | Leu | Glu | Gln | Glu | Lys | Arg | |
| | | 1500 | | | | 1505 | | | | 1510 | | |
| gcc | cag | cag | ccc | gcc | ccc | gcc | ccc | gcc | ccc | ctc | ggc | acc | ccc | gtg | 4664 |
| Ala | Gln | Gln | Pro | Ala | Pro | Ala | Pro | Ala | Pro | Leu | Gly | Thr | Pro | Val | |
| | | 1515 | | | | 1520 | | | | 1525 | | |
| aag | cag | gag | aac | agc | ttc | tcc | agc | tgc | cag | ctg | agc | cag | cag | ccc | 4709 |
| Lys | Gln | Glu | Asn | Ser | Phe | Ser | Ser | Cys | Gln | Leu | Ser | Gln | Gln | Pro | |
| | | 1530 | | | | 1535 | | | | 1540 | | |
| ctg | ggc | ccc | gct | cac | cca | ttc | aac | ccc | agc | ctg | gcg | gcc | cca | gcc | 4754 |
| Leu | Gly | Pro | Ala | His | Pro | Phe | Asn | Pro | Ser | Leu | Ala | Ala | Pro | Ala | |
| | | 1545 | | | | 1550 | | | | 1555 | | |
| acc | aac | cac | ata | gac | cct | tgt | gct | gtg | gcc | ccg | ggg | ccc | ccg | tcc | 4799 |
| Thr | Asn | His | Ile | Asp | Pro | Cys | Ala | Val | Ala | Pro | Gly | Pro | Pro | Ser | |
| | | 1560 | | | | 1565 | | | | 1570 | | |
| gtg | gtg | gtg | aag | cag | gaa | gcc | ttg | cag | cct | gag | ccc | gag | ccg | gtc | 4844 |
| Val | Val | Val | Lys | Gln | Glu | Ala | Leu | Gln | Pro | Glu | Pro | Glu | Pro | Val | |
| | | 1575 | | | | 1580 | | | | 1585 | | |
| ccc | gcc | ccc | cag | ttg | ctt | ctg | ggg | cct | cag | ggc | ccc | agc | ctc | atc | 4889 |
| Pro | Ala | Pro | Gln | Leu | Leu | Leu | Gly | Pro | Gln | Gly | Pro | Ser | Leu | Ile | |
| | | 1590 | | | | 1595 | | | | 1600 | | |
| aag | ggg | gtt | gca | cct | ccc | acc | ctc | atc | acc | gac | tcc | aca | ggg | acc | 4934 |
| Lys | Gly | Val | Ala | Pro | Pro | Thr | Leu | Ile | Thr | Asp | Ser | Thr | Gly | Thr | |
| | | 1605 | | | | 1610 | | | | 1615 | | |
| cac | ctt | gtc | ctc | acc | gtg | acc | aat | aag | aat | gca | gac | agc | cct | ggc | 4979 |
| His | Leu | Val | Leu | Thr | Val | Thr | Asn | Lys | Asn | Ala | Asp | Ser | Pro | Gly | |
| | | 1620 | | | | 1625 | | | | 1630 | | |
| ctg | tcc | agt | ggg | agc | ccc | cag | cag | ccc | tcg | tcc | cag | cct | ggc | tct | 5024 |
| Leu | Ser | Ser | Gly | Ser | Pro | Gln | Gln | Pro | Ser | Ser | Gln | Pro | Gly | Ser | |
| | | 1635 | | | | 1640 | | | | 1645 | | |
| cca | gcg | cct | gcc | ccc | tct | gcc | cag | atg | gac | ctg | gag | cac | cca | ctg | 5069 |
| Pro | Ala | Pro | Ala | Pro | Ser | Ala | Gln | Met | Asp | Leu | Glu | His | Pro | Leu | |
| | | 1650 | | | | 1655 | | | | 1660 | | |
| cag | ccc | ctc | ttt | ggg | acc | ccc | act | tct | ctg | ctg | aag | aag | gaa | cca | 5114 |
| Gln | Pro | Leu | Phe | Gly | Thr | Pro | Thr | Ser | Leu | Leu | Lys | Lys | Glu | Pro | |
| | | 1665 | | | | 1670 | | | | 1675 | | |
| cct | ggc | tat | gag | gaa | gcc | atg | agc | cag | cag | ccc | aaa | cag | cag | gaa | 5159 |
| Pro | Gly | Tyr | Glu | Glu | Ala | Met | Ser | Gln | Gln | Pro | Lys | Gln | Gln | Glu | |
| | | 1680 | | | | 1685 | | | | 1690 | | |
| aat | ggt | tcc | tca | agc | cag | cag | atg | gac | gac | ctg | ttt | gac | att | ctc | 5204 |
| Asn | Gly | Ser | Ser | Ser | Gln | Gln | Met | Asp | Asp | Leu | Phe | Asp | Ile | Leu | |
| | | 1695 | | | | 1700 | | | | 1705 | | |
| att | cag | agc | gga | gaa | att | tca | gca | gat | ttc | aag | gag | ccg | cca | tcc | 5249 |
| Ile | Gln | Ser | Gly | Glu | Ile | Ser | Ala | Asp | Phe | Lys | Glu | Pro | Pro | Ser | |
| | | 1710 | | | | 1715 | | | | 1720 | | |
| ctg | cca | ggg | aag | gag | aag | cca | tcc | ccg | aag | aca | gtc | tgt | ggg | tcc | 5294 |
| Leu | Pro | Gly | Lys | Glu | Lys | Pro | Ser | Pro | Lys | Thr | Val | Cys | Gly | Ser | |
| | | 1725 | | | | 1730 | | | | 1735 | | |
| ccc | ctg | gca | gca | cag | cca | tca | cct | tct | gct | gag | ctc | ccc | cag | gct | 5339 |
| Pro | Leu | Ala | Ala | Gln | Pro | Ser | Pro | Ser | Ala | Glu | Leu | Pro | Gln | Ala | |
| | | 1740 | | | | 1745 | | | | 1750 | | |
| gcc | cca | cct | cct | cca | ggc | tca | ccc | tcc | ctc | cct | gga | cgc | ctg | gag | 5384 |
| Ala | Pro | Pro | Pro | Pro | Gly | Ser | Pro | Ser | Leu | Pro | Gly | Arg | Leu | Glu | |
| | | 1755 | | | | 1760 | | | | 1765 | | |
| gac | ttc | ctg | gag | agc | agc | acg | ggg | ctg | ccc | ctg | ctg | acc | agt | ggg | 5429 |

|  |  |  |  |  |  |  |  |  |  |  |  |
|---|---|---|---|---|---|---|---|---|---|---|---|
| Asp | Phe | Leu | Glu | Ser | Ser | Thr | Gly | Leu | Pro | Leu | Leu | Thr | Ser | Gly |
|  |  |  | 1770 |  |  |  | 1775 |  |  |  | 1780 |

```
cat gac ggg cca gag ccc ctt tcc ctc att gac gac ctc cat agc       5474
His Asp Gly Pro Glu Pro Leu Ser Leu Ile Asp Asp Leu His Ser
        1785                1790                1795 cag atg ctg agc agc act gcc atc ctg gac cac ccc ccg tca ccc       5519
Gln Met Leu Ser Ser Thr Ala Ile Leu Asp His Pro Pro Ser Pro
    1800                1805                1810 atg gac acc tcg gaa ttg cac ttt gtt cct gag ccc agc agc acc       5564
Met Asp Thr Ser Glu Leu His Phe Val Pro Glu Pro Ser Ser Thr
1815                1820                1825 atg ggc ctg gac ctg gct gat ggc cac ctg gac agc atg gac tgg       5609
Met Gly Leu Asp Leu Ala Asp Gly His Leu Asp Ser Met Asp Trp
        1830                1835                1840 ctg gag ctg tcg tca ggt ggt ccc gtg ctg agc cta gcc ccc ctc       5654
Leu Glu Leu Ser Ser Gly Gly Pro Val Leu Ser Leu Ala Pro Leu
    1845                1850                1855 agc acc aca gcc ccc agc ctc ttc tcc aca gac ttc ctc gat ggc       5699
Ser Thr Thr Ala Pro Ser Leu Phe Ser Thr Asp Phe Leu Asp Gly
1860                1865                1870 cat gat ttg cag ctg cac tgg gat tcc tgc ttg tagctctctg           5742
His Asp Leu Gln Leu His Trp Asp Ser Cys Leu
        1875                1880 gctcaagacg gggtggggaa ggggctggga gccagggtac tccaatgcgt ggctctcctg  5802
cgtgattcgg cctctccaca tggttgtgag tcttgacaat cacagcccct gcttttccc   5862
ttccctggga ggctagaaca gagaagccct tactcctggt tcagtgccac gcagggcaga  5922
ggagagcagc tgtcaagaag cagccctggc tctcacgctg gggttttgga cacacggtca  5982
gggtcagggc catttcagct tgacctcctt ttttgaggtc agggggcact gtctgtctgg  6042
ctacaatttg gctaaggtag gtgaagcctg gccaggcggg aggcttctct tctgacccag  6102
ggctgagaca ggttaagggg tgaatctcct tcctttctct ccctgctttg ctgtgaaggg  6162
agaaattagc ctgggcctct acccctatt ccctgtgtct gccaacccca ggatcccagg   6222
gctccctgcc attttagtgt cttggtgtag tgtaaccatt tagtggttgg tgcaacaat   6282
tttatgtaca ggtgtatata cctctatatt atatatcgac atacatatat atttttgggg  6342
gggggcggac aggagatggg tgcaactccc tcccatccta ctctcacaga agggcctgga  6402
tgcaaggtta cccttgagct gtgtgccaca gtctggtgcc cagtctggca tgcagctacc  6462
cagcccacc catcacgtgt gattgacatg taggtaccct gccacggcct atgccccacc   6522
tgccctgctt cctggctcct tatcagtgcc atgagggcag aggtgctacc tggccttcct  6582
gccaggagct ctccacccac tcacattccg tccccgccgc ctcactgcag ccagcgtggt  6642
cctaggacag gaggagcttc gggcccagct tcaccctgcg gtgggctgga gggtggcca   6702
tctcctgccc tggggccact ggcttcacat tctgggctga ctcataggg agtaggggtg    6762
gagtcaccaa aaccagtgct gggacaaaga tggggaaggt gtgtgaactt tttaaaataa  6822
acacaaaaac acag                                                    6836
```

<210> SEQ ID NO 2
<211> LENGTH: 1883
<212> TYPE: PRT
<213> ORGANISM: Homo sapiens

<400> SEQUENCE: 2

```
Met Arg Thr Ala Gly Arg Asp Pro Val Pro Arg Arg Ser Pro Arg Trp
1               5                   10                  15
```

-continued

```
Arg Arg Ala Val Pro Leu Cys Glu Thr Ser Ala Gly Arg Arg Val Thr
             20                  25                  30

Gln Leu Arg Gly Asp Asp Leu Arg Arg Pro Ala Thr Met Lys Gly Lys
         35                  40                  45

Glu Arg Ser Pro Val Lys Ala Lys Arg Ser Arg Gly Gly Glu Asp Ser
     50                  55                  60

Thr Ser Arg Gly Glu Arg Ser Lys Lys Leu Gly Gly Ser Gly Gly Ser
 65                  70                  75                  80

Asn Gly Ser Ser Gly Lys Thr Asp Ser Gly Gly Ser Arg Arg
             85                  90                  95

Ser Leu Leu Asp Lys Ser Ser Arg Gly Gly Ser Arg Glu Tyr
            100                 105                 110

Asp Thr Gly Gly Ser Ser Ser Arg Leu His Ser Tyr Ser Ser
            115                 120                 125

Pro Ser Thr Lys Asn Ser Ser Gly Gly Glu Ser Arg Ser Ser Ser
            130                 135                 140

Arg Gly Gly Gly Glu Ser Arg Ser Ser Gly Ala Ala Ser Ser Ala
145                 150                 155                 160

Pro Gly Gly Asp Gly Ala Glu Tyr Lys Thr Leu Lys Ile Ser Glu
                165                 170                 175

Leu Gly Ser Gln Leu Ser Asp Glu Ala Val Glu Asp Gly Leu Phe His
            180                 185                 190

Glu Phe Lys Arg Phe Gly Asp Val Ser Val Lys Ile Ser His Leu Ser
            195                 200                 205

Gly Ser Gly Ser Gly Asp Glu Arg Val Ala Phe Val Asn Phe Arg Arg
210                 215                 220

Pro Glu Asp Ala Arg Ala Ala Lys His Ala Arg Gly Arg Leu Val Leu
225                 230                 235                 240

Tyr Asp Arg Pro Leu Lys Ile Glu Ala Val Tyr Val Ser Arg Arg Arg
                245                 250                 255

Ser Arg Ser Pro Leu Asp Lys Asp Thr Tyr Pro Pro Ser Ala Ser Val
            260                 265                 270

Val Gly Ala Ser Val Gly Gly His Arg His Pro Pro Gly Gly Gly Gly
        275                 280                 285

Gly Gln Arg Ser Leu Ser Pro Gly Gly Ala Ala Leu Gly Tyr Arg Asp
        290                 295                 300

Tyr Arg Leu Gln Gln Leu Ala Leu Gly Arg Leu Pro Pro Pro Pro
305                 310                 315                 320

Pro Pro Leu Pro Arg Asp Leu Glu Arg Glu Arg Asp Tyr Pro Phe Tyr
                325                 330                 335

Glu Arg Val Arg Pro Ala Tyr Ser Leu Glu Pro Arg Val Gly Ala Gly
            340                 345                 350

Ala Gly Ala Ala Pro Phe Arg Glu Val Asp Glu Ile Ser Pro Glu Asp
        355                 360                 365

Asp Gln Arg Ala Asn Arg Thr Leu Phe Leu Gly Asn Leu Asp Ile Thr
    370                 375                 380

Val Thr Glu Ser Asp Leu Arg Arg Ala Phe Asp Arg Phe Gly Val Ile
385                 390                 395                 400

Thr Glu Val Asp Ile Lys Arg Pro Ser Arg Gly Gln Thr Ser Thr Tyr
                405                 410                 415

Gly Phe Leu Lys Phe Glu Asn Leu Asp Met Ser His Arg Ala Lys Leu
            420                 425                 430
```

```
Ala Met Ser Gly Lys Ile Ile Ile Arg Asn Pro Ile Lys Ile Gly Tyr
        435                 440                 445
Gly Lys Ala Thr Pro Thr Thr Arg Leu Trp Val Gly Gly Leu Gly Pro
        450                 455                 460
Trp Val Pro Leu Ala Ala Leu Ala Arg Glu Phe Asp Arg Phe Gly Thr
465                 470                 475                 480
Ile Arg Thr Ile Asp Tyr Arg Lys Gly Asp Ser Trp Ala Tyr Ile Gln
                485                 490                 495
Tyr Glu Ser Leu Asp Ala Ala His Ala Ala Trp Thr His Met Arg Gly
                500                 505                 510
Phe Pro Leu Gly Gly Pro Asp Arg Arg Leu Arg Val Asp Phe Ala Asp
        515                 520                 525
Thr Glu His Arg Tyr Gln Gln Gln Tyr Leu Gln Pro Leu Pro Leu Thr
        530                 535                 540
His Tyr Glu Leu Val Thr Asp Ala Phe Gly His Arg Ala Pro Asp Pro
545                 550                 555                 560
Leu Arg Gly Ala Arg Asp Arg Thr Pro Pro Leu Leu Tyr Arg Asp Arg
                565                 570                 575
Asp Arg Asp Leu Tyr Pro Asp Ser Asp Trp Val Pro Pro Pro Pro Pro
                580                 585                 590
Val Arg Glu Arg Ser Thr Arg Thr Ala Ala Thr Ser Val Pro Ala Tyr
        595                 600                 605
Glu Pro Leu Asp Ser Leu Asp Arg Arg Arg Asp Gly Trp Ser Leu Asp
        610                 615                 620
Arg Asp Arg Gly Asp Arg Asp Leu Pro Ser Ser Arg Asp Gln Pro Arg
625                 630                 635                 640
Lys Arg Arg Leu Pro Glu Glu Ser Gly Gly Arg His Leu Asp Arg Ser
                645                 650                 655
Pro Glu Ser Asp Arg Pro Arg Lys Arg His Cys Ala Pro Ser Pro Asp
                660                 665                 670
Arg Ser Pro Glu Leu Ser Ser Ser Arg Asp Arg Tyr Asn Ser Asp Asn
        675                 680                 685
Asp Arg Ser Ser Arg Leu Leu Leu Glu Arg Pro Ser Pro Ile Arg Asp
        690                 695                 700
Gly Arg Gly Ser Leu Glu Lys Ser Gln Gly Asp Lys Arg Asp Arg Lys
705                 710                 715                 720
Asn Ser Ala Ser Ala Glu Arg Asp Arg Lys His Arg Thr Thr Ala Pro
                725                 730                 735
Thr Glu Gly Lys Ser Pro Leu Lys Lys Glu Asp Arg Ser Asp Gly Ser
                740                 745                 750
Ala Pro Ser Thr Ser Thr Ala Ser Ser Lys Leu Lys Ser Pro Ser Gln
        755                 760                 765
Lys Gln Asp Gly Gly Thr Ala Pro Val Ala Ser Ala Ser Pro Lys Leu
        770                 775                 780
Cys Leu Ala Trp Gln Gly Met Leu Leu Leu Lys Asn Ser Asn Phe Pro
785                 790                 795                 800
Ser Asn Met His Leu Leu Gln Gly Asp Leu Gln Val Ala Ser Ser Leu
                805                 810                 815
Leu Val Glu Gly Ser Thr Gly Gly Lys Val Ala Gln Leu Lys Ile Thr
        820                 825                 830
Gln Arg Leu Arg Leu Asp Gln Pro Lys Leu Asp Glu Val Thr Arg Arg
        835                 840                 845
Ile Lys Val Ala Gly Pro Asn Gly Tyr Ala Ile Leu Leu Ala Val Pro
```

-continued

```
            850             855             860
Gly Ser Ser Asp Ser Arg Ser Ser Ser Ser Ala Ala Ser Asp Thr
865                     870              875                 880
Ala Thr Ser Thr Gln Arg Pro Leu Arg Asn Leu Val Ser Tyr Leu Lys
                885                 890                 895
Gln Lys Gln Ala Ala Gly Val Ile Ser Leu Pro Val Gly Gly Asn Lys
            900                 905                 910
Asp Lys Glu Asn Thr Gly Val Leu His Ala Phe Pro Pro Cys Glu Phe
            915                 920                 925
Ser Gln Gln Phe Leu Asp Ser Pro Ala Lys Ala Leu Ala Lys Ser Glu
930                 935                 940
Glu Asp Tyr Leu Val Met Ile Ile Val Arg Ala Leu Lys Ser Pro Ala
945                 950                 955                 960
Ala Phe His Glu Gln Arg Arg Ser Leu Glu Arg Ala Arg Thr Glu Asp
                965                 970                 975
Tyr Leu Lys Arg Lys Ile Arg Ser Arg Pro Glu Arg Ser Glu Leu Val
            980                 985                 990
Arg Met His Ile Leu Glu Glu Thr Ser Ala Glu Pro Ser Leu Gln Ala
            995                 1000                1005
Lys Gln Leu Lys Leu Lys Arg Ala Arg Leu Ala Asp Asp Leu Asn
        1010                1015            1020
Glu Lys Ile Ala Gln Arg Pro Gly Pro Met Glu Leu Val Glu Lys
        1025                1030            1035
Asn Ile Leu Pro Val Glu Ser Ser Leu Lys Glu Ala Ile Ile Val
        1040                1045            1050
Gly Gln Val Asn Tyr Pro Lys Val Ala Asp Ser Ser Phe Asp
        1055                1060            1065
Glu Asp Ser Ser Asp Ala Leu Ser Pro Glu Gln Pro Ala Ser His
        1070                1075            1080
Glu Ser Gln Gly Ser Val Pro Ser Pro Leu Glu Ala Arg Val Ser
        1085                1090            1095
Glu Pro Leu Leu Ser Ala Thr Ser Ala Ser Pro Thr Gln Val Val
        1100                1105            1110
Ser Gln Leu Pro Met Gly Arg Asp Ser Arg Glu Met Leu Phe Leu
        1115                1120            1125
Ala Glu Gln Pro Pro Leu Pro Pro Pro Leu Leu Pro Pro Ser
        1130                1135            1140
Leu Thr Asn Gly Thr Thr Ile Pro Thr Ala Lys Ser Thr Pro Thr
        1145                1150            1155
Leu Ile Lys Gln Ser Gln Pro Lys Ser Ala Ser Glu Lys Ser Gln
        1160                1165            1170
Arg Ser Lys Lys Ala Lys Glu Leu Lys Pro Lys Val Lys Lys Leu
        1175                1180            1185
Lys Tyr His Gln Tyr Ile Pro Pro Asp Gln Lys Gln Asp Arg Gly
        1190                1195            1200
Ala Pro Pro Met Asp Ser Ser Tyr Ala Lys Ile Leu Gln Gln Gln
        1205                1210            1215
Gln Leu Phe Leu Gln Leu Gln Ile Leu Asn Gln Gln Gln Gln Gln
        1220                1225            1230
His His Asn Tyr Gln Ala Ile Leu Pro Ala Pro Pro Lys Ser Ala
        1235                1240            1245
Gly Glu Ala Leu Gly Ser Ser Gly Thr Pro Pro Val Arg Ser Leu
        1250                1255            1260
```

```
Ser Thr Thr Asn Ser Ser Ser Ser Gly Ala Pro Gly Pro Cys
    1265            1270            1275

Gly Leu Ala Arg Gln Asn Ser Thr Ser Leu Thr Gly Lys Pro Gly
    1280            1285            1290

Ala Leu Pro Ala Asn Leu Asp Asp Met Lys Val Ala Glu Leu Lys
    1295            1300            1305

Gln Glu Leu Lys Leu Arg Ser Leu Pro Val Ser Gly Thr Lys Thr
    1310            1315            1320

Glu Leu Ile Glu Arg Leu Arg Ala Tyr Gln Asp Gln Ile Ser Pro
    1325            1330            1335

Val Pro Gly Ala Pro Lys Ala Pro Ala Ala Thr Ser Ile Leu His
    1340            1345            1350

Lys Ala Gly Glu Val Val Val Ala Phe Pro Ala Ala Arg Leu Ser
    1355            1360            1365

Thr Gly Pro Ala Leu Val Ala Ala Gly Leu Ala Pro Ala Glu Val
    1370            1375            1380

Val Val Ala Thr Val Ala Ser Ser Gly Val Val Lys Phe Gly Ser
    1385            1390            1395

Thr Gly Ser Thr Pro Pro Val Ser Pro Thr Pro Ser Glu Arg Ser
    1400            1405            1410

Leu Leu Ser Thr Gly Asp Glu Asn Ser Thr Pro Gly Asp Thr Phe
    1415            1420            1425

Gly Glu Met Val Thr Ser Pro Leu Thr Gln Leu Thr Leu Gln Ala
    1430            1435            1440

Ser Pro Leu Gln Ile Leu Val Lys Glu Glu Gly Pro Arg Ala Gly
    1445            1450            1455

Ser Cys Cys Leu Ser Pro Gly Gly Arg Ala Glu Leu Glu Gly Arg
    1460            1465            1470

Asp Lys Asp Gln Met Leu Gln Glu Lys Asp Lys Gln Ile Glu Ala
    1475            1480            1485

Leu Thr Arg Met Leu Arg Gln Lys Gln Gln Leu Val Glu Arg Leu
    1490            1495            1500

Lys Leu Gln Leu Glu Gln Glu Lys Arg Ala Gln Gln Pro Ala Pro
    1505            1510            1515

Ala Pro Ala Pro Leu Gly Thr Pro Val Lys Gln Glu Asn Ser Phe
    1520            1525            1530

Ser Ser Cys Gln Leu Ser Gln Gln Pro Leu Gly Pro Ala His Pro
    1535            1540            1545

Phe Asn Pro Ser Leu Ala Ala Pro Ala Thr Asn His Ile Asp Pro
    1550            1555            1560

Cys Ala Val Ala Pro Gly Pro Pro Ser Val Val Lys Gln Glu
    1565            1570            1575

Ala Leu Gln Pro Glu Pro Glu Pro Val Pro Ala Pro Gln Leu Leu
    1580            1585            1590

Leu Gly Pro Gln Gly Pro Ser Leu Ile Lys Gly Val Ala Pro Pro
    1595            1600            1605

Thr Leu Ile Thr Asp Ser Thr Gly Thr His Leu Val Leu Thr Val
    1610            1615            1620

Thr Asn Lys Asn Ala Asp Ser Pro Gly Leu Ser Ser Gly Ser Pro
    1625            1630            1635

Gln Gln Pro Ser Ser Gln Pro Gly Ser Pro Ala Pro Ala Pro Ser
    1640            1645            1650
```

-continued

| | | | | | | | | | | |
|---|---|---|---|---|---|---|---|---|---|---|
| Ala | Gln | Met | Asp | Leu | Glu | His | Pro | Leu | Gln | Pro | Leu | Phe | Gly | Thr |
| | 1655 | | | | 1660 | | | | 1665 | |

Ala Gln Met Asp Leu Glu His Pro Leu Gln Pro Leu Phe Gly Thr
    1655                1660                1665

Pro Thr Ser Leu Leu Lys Lys Glu Pro Pro Gly Tyr Glu Glu Ala
    1670                1675                1680

Met Ser Gln Gln Pro Lys Gln Glu Asn Gly Ser Ser Ser Gln
    1685                1690                1695

Gln Met Asp Asp Leu Phe Asp Ile Leu Ile Gln Ser Gly Glu Ile
    1700                1705                1710

Ser Ala Asp Phe Lys Glu Pro Pro Ser Leu Pro Gly Lys Glu Lys
    1715                1720                1725

Pro Ser Pro Lys Thr Val Cys Gly Ser Pro Leu Ala Ala Gln Pro
    1730                1735                1740

Ser Pro Ser Ala Glu Leu Pro Gln Ala Ala Pro Pro Pro Gly
    1745                1750                1755

Ser Pro Ser Leu Pro Gly Arg Leu Glu Asp Phe Leu Glu Ser Ser
    1760                1765                1770

Thr Gly Leu Pro Leu Leu Thr Ser Gly His Asp Gly Pro Glu Pro
    1775                1780                1785

Leu Ser Leu Ile Asp Asp Leu His Ser Gln Met Leu Ser Ser Thr
    1790                1795                1800

Ala Ile Leu Asp His Pro Pro Ser Pro Met Asp Thr Ser Glu Leu
    1805                1810                1815

His Phe Val Pro Glu Pro Ser Ser Thr Met Gly Leu Asp Leu Ala
    1820                1825                1830

Asp Gly His Leu Asp Ser Met Asp Trp Leu Glu Leu Ser Ser Gly
    1835                1840                1845

Gly Pro Val Leu Ser Leu Ala Pro Leu Ser Thr Thr Ala Pro Ser
    1850                1855                1860

Leu Phe Ser Thr Asp Phe Leu Asp Gly His Asp Leu Gln Leu His
    1865                1870                1875

Trp Asp Ser Cys Leu
    1880

<210> SEQ ID NO 3
<211> LENGTH: 923
<212> TYPE: DNA
<213> ORGANISM: Homo sapiens
<220> FEATURE:
<221> NAME/KEY: CDS
<222> LOCATION: (551)..(601)

<400> SEQUENCE: 3 tcccatctttt cccaccctct tggttgccgc tggccacacg ccctccgctg gcggcgactt        60
ctcagctccg tgcgcccggg ctggacagtg agcctcgaga ggagacgcgg gcggctagag       120
ccggagtggg gcgagccgcg gaacccggcc gggagccgcg cgaggcgtga tcggagggta       180
tggttggcat ggaattgaat tcatctgtc tgtgggaatt gtaagcaaga ttgccatcac        240
gaaagccaaa gtggatttct ccagtgtggt gtgcctgccc ccttccgtca ttgctgtgaa       300
tgggctggac ggaggagggg ccggcgaaaa tgatgatgaa ccagtgctcg tgtccttatc      360
tgcggcaccc agtccccaga gtgaagctgt tgccaatgaa ctgcaggagc tctccttgca       420
gcccaagctg accctaggcc tccaccctgg caggaatccc aatttgcctc cacttagtga       480
gcggaagaat gtgctacagt tgaaactcca gcagcgccgg acccgggaag aactggtgag       540
ccaagggatc atg ccg cca aaa ctg gtt gaa cag cgg atg aag ata tgg       589
              Met Pro Pro Lys Leu Val Glu Gln Arg Met Lys Ile Trp

```
                    1               5              10
aat tca aag ctc taatggacct ttttgaagag aagttgtggc ttatgtggag          641
Asn Ser Lys Leu
         15 tttacatggg cctctgatgg aagaaagcta atctgtttag tatttgtgca ttttactaaa    701 atggcagctt aaagttgtgt atctgctatt gtgatgccaa tgccggtgtt ttaagtggaa    761 aaaaaatgac ctctttgatt tgtgctgtgt acacaagatt tctggaaaag taagaaaaa     821 cccttttat ggctcacaca gcttaagagt agctgtctct caaacgtgcg ctcacagttg     881 agctgctttt gttttattct aaataaattg tttcttttga gg                       923

<210> SEQ ID NO 4
<211> LENGTH: 17
<212> TYPE: PRT
<213> ORGANISM: Homo sapiens

<400> SEQUENCE: 4

Met Pro Pro Lys Leu Val Glu Gln Arg Met Lys Ile Trp Asn Ser Lys
1               5                  10                  15
Leu

<210> SEQ ID NO 5
<211> LENGTH: 1034
<212> TYPE: DNA
<213> ORGANISM: Homo sapiens
<220> FEATURE:
<221> NAME/KEY: CDS
<222> LOCATION: (551)..(625)

<400> SEQUENCE: 5
tcccatcttt ccacccctct tggttgccgc tggccacacg ccctccgctg gcggcgactt    60
ctcagctccg tgcgcccggg ctggacagtg agcctcgaga ggagacgcgg gcggctagag    120
ccggagtggg gcgagccgcg gaacccggcc gggagccgcg cgaggcgtga tcggagggta    180
tggttggcat ggaattgaat tcatctgtc tgtgggaatt gtaagcaaga ttgccatcac     240
gaaagccaaa gtggatttct ccagtgtggt gtgcctgccc ccttccgtca ttgctgtgaa    300
tgggctggac ggaggagggg ccggcgaaaa tgatgatgaa ccagtgctcg tgtccttatc    360
tgcggcaccc agtccccaga gtgaagctgt tgccaatgaa ctgcaggagc tctccttgca    420
gcccaagctg accctaggcc tccaccctgg caggaatccc aatttgcctc cacttagtga    480
gcggaagaat gtgctacagt tgaaactcca gcagcgccgg acccgggaag aactggtgag    540
ccaagggatc atg ccg cgg ttt ggt ttt cag ata gga gtt agg tat gag      589
            Met Pro Arg Phe Gly Phe Gln Ile Gly Val Arg Tyr Glu
            1               5                   10 aac aag aag aga gaa aac ttg gcg ctg acc ctg tta tagtggttat          635
Asn Lys Lys Arg Glu Asn Leu Ala Leu Thr Leu Leu
         15                  20                  25 agtggtgtcc ctaaagggag gaaatgattt cagcaaaact ggttgaacag cggatgaaga    695
tatggaattc aaagctctaa tggacctttt tgaagagaag ttgtggctta tgtgagtttt    755 acatggcct ctgatggaag aaagctaatc tgtttagtat tgtgcatttt actaaaatg     815 gcagcttaaa gttgtgtatc tgctattgtg atgccaatgc cggtgtttta agtggaaaaa    875
aaatgacctc tttgatttgt gctgtgtaca caagatttct ggaaaagtaa agaaaaaccc    935 ttttatggc tcacacagct taagagtagc tgtctctcaa acgtgcgctc acagttgagc     995
tgcttttgtt ttattctaaa taaattgttt cttttgagg                           1034
```

-continued

<210> SEQ ID NO 6
<211> LENGTH: 25
<212> TYPE: PRT
<213> ORGANISM: Homo sapiens

<400> SEQUENCE: 6

```
Met Pro Arg Phe Gly Phe Gln Ile Gly Val Arg Tyr Glu Asn Lys Lys
1               5                   10                  15

Arg Glu Asn Leu Ala Leu Thr Leu Leu
            20                  25
```

<210> SEQ ID NO 7
<211> LENGTH: 3312
<212> TYPE: DNA
<213> ORGANISM: Homo sapiens
<220> FEATURE:
<221> NAME/KEY: CDS
<222> LOCATION: (84)..(2990)

<400> SEQUENCE: 7

```
ggcgccttcc tggagcgcgg ggagatgtaa agatagacaa ataatttcc caatgagact     60 gtagaagaga gagcaattgg cca atg agg act gcg ggg cgg gac cct gtg ccg    113
                        Met Arg Thr Ala Gly Arg Asp Pro Val Pro
                        1               5                   10 cgg cgg agt cca aga tgg cgg cgt gcg gtt ccg ctg tgt gaa acg agc      161
Arg Arg Ser Pro Arg Trp Arg Arg Ala Val Pro Leu Cys Glu Thr Ser
                15                  20                  25 gcg ggg cgg cgg gtt act cag ctc cgc gga gac gac ctc cga cga ccc      209
Ala Gly Arg Arg Val Thr Gln Leu Arg Gly Asp Asp Leu Arg Arg Pro
        30                  35                  40 gca aca atg aag gga aaa gag cgc tcg cca gtg aag gcc aaa cgc tcc      257
Ala Thr Met Lys Gly Lys Glu Arg Ser Pro Val Lys Ala Lys Arg Ser
    45                  50                  55 cgt ggt ggt gag gac tcg act tcc cgc ggt gag cgg agc aag aag tta      305
Arg Gly Gly Glu Asp Ser Thr Ser Arg Gly Glu Arg Ser Lys Lys Leu
60                  65                  70 ggg ggc tct ggt ggc agc aat ggg agc agc agc gga aag acc gat agc      353
Gly Gly Ser Gly Gly Ser Asn Gly Ser Ser Ser Gly Lys Thr Asp Ser
75                  80                  85                  90 ggc ggt ggg tcg cgg cgg agt ctc ctc ctg gac aag tcc agc agt cga      401
Gly Gly Gly Ser Arg Arg Ser Leu Leu Leu Asp Lys Ser Ser Ser Arg
                95                  100                 105 ggt ggc agc cgc gag tat gat acc ggt ggg ggc agc tcc agt agc cgc      449
Gly Gly Ser Arg Glu Tyr Asp Thr Gly Gly Gly Ser Ser Ser Ser Arg
            110                 115                 120 ttg cat agt tat agc tcc ccg agc acc aaa aat tct tcg ggc ggg ggc      497
Leu His Ser Tyr Ser Ser Pro Ser Thr Lys Asn Ser Ser Gly Gly Gly
        125                 130                 135 gag tcg cgc agc agc tcc cgg ggt gga ggc ggg gag tca cgt tcc tct      545
Glu Ser Arg Ser Ser Ser Arg Gly Gly Gly Gly Glu Ser Arg Ser Ser
    140                 145                 150 ggg gcc gcc tcc tca gct ccc ggc ggc ggg gac ggc gcg gaa tac aag      593
Gly Ala Ala Ser Ser Ala Pro Gly Gly Gly Asp Gly Ala Glu Tyr Lys
155                 160                 165                 170 act ctg aag ata agc gag ttg ggg tcc cag ctt agt gac gaa gcg gtg      641
Thr Leu Lys Ile Ser Glu Leu Gly Ser Gln Leu Ser Asp Glu Ala Val
                175                 180                 185 gag gac ggc ctg ttt cat gag ttc aaa cgc ttc ggt gat gta agt gtg      689
Glu Asp Gly Leu Phe His Glu Phe Lys Arg Phe Gly Asp Val Ser Val
            190                 195                 200
```

-continued

```
aaa atc agt cat ctg tcg ggt tct ggc agc ggg gat gag cgg gta gcc        737
Lys Ile Ser His Leu Ser Gly Ser Gly Ser Gly Asp Glu Arg Val Ala
        205                 210                 215 ttt gtg aac ttc cgg cgg cca gag gac gcg cgg gcg gcc aag cat gcc        785
Phe Val Asn Phe Arg Arg Pro Glu Asp Ala Arg Ala Ala Lys His Ala
    220                 225                 230 aga ggc cgc ctg gtg ctc tat gac cgg cct ctg aag ata gaa gct gtg        833
Arg Gly Arg Leu Val Leu Tyr Asp Arg Pro Leu Lys Ile Glu Ala Val
235                 240                 245                 250 tat gtg agc cgg cgc cgc agc cgc tcc cct tta gac aaa gat act tat        881
Tyr Val Ser Arg Arg Arg Ser Arg Ser Pro Leu Asp Lys Asp Thr Tyr
                255                 260                 265 cct cca tca gcc agt gtg gtc ggg gcc tct gta ggt ggt cac cgg cac        929
Pro Pro Ser Ala Ser Val Val Gly Ala Ser Val Gly Gly His Arg His
            270                 275                 280 ccc cct gga ggt ggt gga ggc cag aga tca ctt tcc cct ggt ggc gct        977
Pro Pro Gly Gly Gly Gly Gly Gln Arg Ser Leu Ser Pro Gly Gly Ala
        285                 290                 295 gct ttg gga tac aga gac tac cgg ctg cag cag ttg gct ctt ggc cgc       1025
Ala Leu Gly Tyr Arg Asp Tyr Arg Leu Gln Gln Leu Ala Leu Gly Arg
    300                 305                 310 ctg ccc cct cca cct ccg cca cca ttg cct cga gac ctg gag aga gaa       1073
Leu Pro Pro Pro Pro Pro Pro Leu Pro Arg Asp Leu Glu Arg Glu
315                 320                 325                 330 aga gac tac ccg ttc tat gag aga gtg cgc cct gca tac agt ctt gag       1121
Arg Asp Tyr Pro Phe Tyr Glu Arg Val Arg Pro Ala Tyr Ser Leu Glu
                335                 340                 345 cca agg gtg gga gct gga gca ggt gct gct cct ttc aga gaa gtg gat       1169
Pro Arg Val Gly Ala Gly Ala Gly Ala Ala Pro Phe Arg Glu Val Asp
            350                 355                 360 gag att tca ccc gag gat gat cag cga gct aac cgg acg ctc ttc ttg       1217
Glu Ile Ser Pro Glu Asp Asp Gln Arg Ala Asn Arg Thr Leu Phe Leu
        365                 370                 375 ggc aac cta gac atc act gta acg gag agt gat tta aga agg gcg ttt       1265
Gly Asn Leu Asp Ile Thr Val Thr Glu Ser Asp Leu Arg Arg Ala Phe
    380                 385                 390 gat cgc ttt gga gtc atc aca gaa gta gat atc aag agg cct tct cgc       1313
Asp Arg Phe Gly Val Ile Thr Glu Val Asp Ile Lys Arg Pro Ser Arg
395                 400                 405                 410 ggc cag act agt act tac ggc ttt ctc aaa ttt gag aac tta gat atg       1361
Gly Gln Thr Ser Thr Tyr Gly Phe Leu Lys Phe Glu Asn Leu Asp Met
                415                 420                 425 tct cac cgg gcc aaa tta gca atg tct ggc aaa att ata att cgg aat       1409
Ser His Arg Ala Lys Leu Ala Met Ser Gly Lys Ile Ile Ile Arg Asn
            430                 435                 440 cct atc aaa att ggt tat ggt aaa gct aca ccc acc acc cgc ctc tgg       1457
Pro Ile Lys Ile Gly Tyr Gly Lys Ala Thr Pro Thr Thr Arg Leu Trp
        445                 450                 455 gtg gga ggc ctg gga cct tgg gtt cct ctt gct gcc ctg gca cga gaa       1505
Val Gly Gly Leu Gly Pro Trp Val Pro Leu Ala Ala Leu Ala Arg Glu
    460                 465                 470 ttt gat cga ttt ggc acc ata cgc acc ata gac tac cga aaa ggt gat       1553
Phe Asp Arg Phe Gly Thr Ile Arg Thr Ile Asp Tyr Arg Lys Gly Asp
475                 480                 485                 490 agt tgg gca tat atc cag tat gaa agc ctg gat gca gcg cat gct gcc       1601
Ser Trp Ala Tyr Ile Gln Tyr Glu Ser Leu Asp Ala Ala His Ala Ala
                495                 500                 505 tgg acc cat atg cgg ggc ttc cca ctt ggt ggc cca gat cga cgc ctt       1649
Trp Thr His Met Arg Gly Phe Pro Leu Gly Gly Pro Asp Arg Arg Leu
```

-continued

|     |     |     | 510 |     |     |     | 515 |     |     |     | 520 |     |     |     |      |
|-----|-----|-----|-----|-----|-----|-----|-----|-----|-----|-----|-----|-----|-----|-----|------|
| aga | gta | gac | ttt | gcc | gac | acc | gaa | cat | cgt | tac | cag | cag | cag | tat | ctg  | 1697 |
| Arg | Val | Asp | Phe | Ala | Asp | Thr | Glu | His | Arg | Tyr | Gln | Gln | Gln | Tyr | Leu  |
|     |     | 525 |     |     |     |     | 530 |     |     |     |     | 535 |     |     |      |

| cag | cct | ctg | ccc | ttg | act | cat | tat | gag | ctg | gtg | aca | gat | gct | ttt | gga  | 1745 |
|-----|-----|-----|-----|-----|-----|-----|-----|-----|-----|-----|-----|-----|-----|-----|------|
| Gln | Pro | Leu | Pro | Leu | Thr | His | Tyr | Glu | Leu | Val | Thr | Asp | Ala | Phe | Gly  |
|     | 540 |     |     |     |     |     | 545 |     |     |     |     | 550 |     |     |      |

| cat | cgg | gca | cca | gac | cct | ttg | agg | ggt | gct | cgg | gat | agg | aca | cca | ccc  | 1793 |
| His | Arg | Ala | Pro | Asp | Pro | Leu | Arg | Gly | Ala | Arg | Asp | Arg | Thr | Pro | Pro  |
| 555 |     |     |     |     | 560 |     |     |     |     | 565 |     |     |     |     | 570  |

| tta | cta | tac | aga | gat | cgt | gat | agg | gac | ctt | tat | cct | gac | tct | gat | tgg  | 1841 |
| Leu | Leu | Tyr | Arg | Asp | Arg | Asp | Arg | Asp | Leu | Tyr | Pro | Asp | Ser | Asp | Trp  |
|     |     |     |     | 575 |     |     |     |     | 580 |     |     |     |     | 585 |      |

| gtg | cca | ccc | cca | ccc | cca | gtc | cga | gaa | cgc | agc | act | cgg | act | gca | gct  | 1889 |
| Val | Pro | Pro | Pro | Pro | Val | Arg | Glu | Arg | Ser | Thr | Arg | Thr | Ala | Ala |      |
|     |     |     |     | 590 |     |     |     |     | 595 |     |     |     | 600 |     |      |

| act | tct | gtg | cct | gct | tat | gag | cca | ctg | gat | agc | cta | gat | cgc | agg | cgg  | 1937 |
| Thr | Ser | Val | Pro | Ala | Tyr | Glu | Pro | Leu | Asp | Ser | Leu | Asp | Arg | Arg | Arg  |
|     |     |     | 605 |     |     |     |     | 610 |     |     |     |     | 615 |     |      |

| gat | ggt | tgg | tcc | ttg | gac | cgg | gac | aga | ggt | gat | cga | gat | ctg | ccc | agc  | 1985 |
| Asp | Gly | Trp | Ser | Leu | Asp | Arg | Asp | Arg | Gly | Asp | Arg | Asp | Leu | Pro | Ser  |
|     |     | 620 |     |     |     |     | 625 |     |     |     |     | 630 |     |     |      |

| agc | aga | gac | cag | cct | agg | aag | cga | agg | ctg | cct | gag | gag | agt | gga | gga  | 2033 |
| Ser | Arg | Asp | Gln | Pro | Arg | Lys | Arg | Arg | Leu | Pro | Glu | Glu | Ser | Gly | Gly  |
| 635 |     |     |     |     | 640 |     |     |     |     | 645 |     |     |     |     | 650  |

| cgt | cat | ctg | gat | agg | tct | cct | gag | agt | gac | cgc | cca | cga | aaa | cgt | cac  | 2081 |
| Arg | His | Leu | Asp | Arg | Ser | Pro | Glu | Ser | Asp | Arg | Pro | Arg | Lys | Arg | His  |
|     |     |     |     | 655 |     |     |     |     | 660 |     |     |     |     | 665 |      |

| tgc | gct | cct | tct | cct | gac | cgc | agt | cca | gaa | ttg | agc | agt | agc | cgg | gat  | 2129 |
| Cys | Ala | Pro | Ser | Pro | Asp | Arg | Ser | Pro | Glu | Leu | Ser | Ser | Ser | Arg | Asp  |
|     |     |     | 670 |     |     |     |     | 675 |     |     |     |     | 680 |     |      |

| cgt | tac | aac | agc | gac | aat | gat | cga | tct | tcc | cgt | ctt | ctc | ttg | gaa | agg  | 2177 |
| Arg | Tyr | Asn | Ser | Asp | Asn | Asp | Arg | Ser | Ser | Arg | Leu | Leu | Leu | Glu | Arg  |
|     |     |     |     | 685 |     |     |     |     | 690 |     |     |     |     | 695 |      |

| ccc | tct | cca | atc | aga | gac | gga | cga | ggt | agt | ttg | gag | aag | agc | cag | ggt  | 2225 |
| Pro | Ser | Pro | Ile | Arg | Asp | Gly | Arg | Gly | Ser | Leu | Glu | Lys | Ser | Gln | Gly  |
|     | 700 |     |     |     |     | 705 |     |     |     |     | 710 |     |     |     |      |

| gac | aag | cga | gac | cgt | aaa | aac | tct | gca | tca | gct | gaa | cga | gat | agg | aag  | 2273 |
| Asp | Lys | Arg | Asp | Arg | Lys | Asn | Ser | Ala | Ser | Ala | Glu | Arg | Asp | Arg | Lys  |
| 715 |     |     |     |     | 720 |     |     |     |     | 725 |     |     |     |     | 730  |

| cac | cgg | aca | act | gct | ccc | act | gag | gga | aaa | agc | cct | ctg | aaa | aaa | gaa  | 2321 |
| His | Arg | Thr | Thr | Ala | Pro | Thr | Glu | Gly | Lys | Ser | Pro | Leu | Lys | Lys | Glu  |
|     |     |     | 735 |     |     |     |     | 740 |     |     |     |     | 745 |     |      |

| gac | cgc | tct | gat | ggg | agt | gca | cct | agc | acc | agc | act | gct | tcc | tcc | aag  | 2369 |
| Asp | Arg | Ser | Asp | Gly | Ser | Ala | Pro | Ser | Thr | Ser | Thr | Ala | Ser | Ser | Lys  |
|     |     |     | 750 |     |     |     |     | 755 |     |     |     |     | 760 |     |      |

| ctg | aag | tcc | ccg | tcc | cag | aaa | cag | gat | ggg | ggg | aca | gcc | cct | gtg | gca  | 2417 |
| Leu | Lys | Ser | Pro | Ser | Gln | Lys | Gln | Asp | Gly | Gly | Thr | Ala | Pro | Val | Ala  |
|     | 765 |     |     |     |     | 770 |     |     |     |     | 775 |     |     |     |      |

| tca | gcc | tct | ccc | aaa | ctc | tgt | ttg | gcc | tgg | cag | ggc | atg | ctt | cta | ctg  | 2465 |
| Ser | Ala | Ser | Pro | Lys | Leu | Cys | Leu | Ala | Trp | Gln | Gly | Met | Leu | Leu | Leu  |
| 780 |     |     |     |     | 785 |     |     |     |     | 790 |     |     |     |     |      |

| aag | aac | agc | aac | ttt | cct | tcc | aac | atg | cat | ctg | ttg | cag | ggt | gac | ctc  | 2513 |
| Lys | Asn | Ser | Asn | Phe | Pro | Ser | Asn | Met | His | Leu | Leu | Gln | Gly | Asp | Leu  |
| 795 |     |     |     |     | 800 |     |     |     |     | 805 |     |     |     |     | 810  |

| caa | gtg | gct | agt | agt | ctt | ctt | gtg | gag | ggt | tca | act | gga | ggc | aaa | gtg  | 2561 |
| Gln | Val | Ala | Ser | Ser | Leu | Leu | Val | Glu | Gly | Ser | Thr | Gly | Gly | Lys | Val  |
|     |     |     |     | 815 |     |     |     |     | 820 |     |     |     |     | 825 |      |

| gcc | cag | ctc | aag | atc | act | cag | cgt | ctc | cgt | ttg | gac | cag | ccc | aag | ttg  | 2609 |

```
Ala Gln Leu Lys Ile Thr Gln Arg Leu Arg Leu Asp Gln Pro Lys Leu
            830                 835                 840 gat gaa gta act cga cgc atc aaa gta gca ggg ccc aat ggt tat gcc       2657
Asp Glu Val Thr Arg Arg Ile Lys Val Ala Gly Pro Asn Gly Tyr Ala
        845                 850                 855 att ctt ttg gct gtg cct gga agt tct gac agc cgg tcc tcc tct tcc       2705
Ile Leu Leu Ala Val Pro Gly Ser Ser Asp Ser Arg Ser Ser Ser Ser
    860                 865                 870 tca gct gca tca gac act gcc act tct act cag agg cca ctt agg aac       2753
Ser Ala Ala Ser Asp Thr Ala Thr Ser Thr Gln Arg Pro Leu Arg Asn
875                 880                 885                 890 ctt gtg tcc tat tta aag caa aag cag gca gcc ggg gtg atc agc ctc       2801
Leu Val Ser Tyr Leu Lys Gln Lys Gln Ala Ala Gly Val Ile Ser Leu
            895                 900                 905 cct gtg ggg ggc aac aaa gac aag gaa aac acc ggg gtc ctt cat gcc       2849
Pro Val Gly Gly Asn Lys Asp Lys Glu Asn Thr Gly Val Leu His Ala
        910                 915                 920 ttc cca cct tgt gag ttc tcc cag cag ttc ctg gat tcc cct gcc aag       2897
Phe Pro Pro Cys Glu Phe Ser Gln Gln Phe Leu Asp Ser Pro Ala Lys
    925                 930                 935 gca ctg gcc aaa tct gaa gaa gat tac ctg gtc atg atc att gtc cgt       2945
Ala Leu Ala Lys Ser Glu Glu Asp Tyr Leu Val Met Ile Ile Val Arg
940                 945                 950 gca aaa ctg gtt gaa cag cgg atg aag ata tgg aat tca aag ctc           2990
Ala Lys Leu Val Glu Gln Arg Met Lys Ile Trp Asn Ser Lys Leu
955                 960                 965 taatggacct ttttgaagag aagttgtggc ttatgtggag tttacatggg cctctgatgg     3050
aagaaagcta atctgtttag tatttgtgca ttttactaaa atggcagctt aaagttgtgt     3110
atctgctatt gtgatgccaa tgccggtgtt ttaagtggaa aaaaaatgac ctctttgatt     3170
tgtgctgtgt acacaagatt tctggaaaag taaagaaaaa cccttttat ggctcacaca     3230 gcttaagagt agctgtctct caaacgtgcg ctcacagttg agctgctttt gttttattct    3290
aaataaattg tttcttttga gg                                              3312

<210> SEQ ID NO 8
<211> LENGTH: 969
<212> TYPE: PRT
<213> ORGANISM: Homo sapiens

<400> SEQUENCE: 8

Met Arg Thr Ala Gly Arg Asp Pro Val Pro Arg Arg Ser Pro Arg Trp
1               5                   10                  15

Arg Arg Ala Val Pro Leu Cys Glu Thr Ser Ala Gly Arg Arg Val Thr
            20                  25                  30

Gln Leu Arg Gly Asp Asp Leu Arg Arg Pro Ala Thr Met Lys Gly Lys
        35                  40                  45

Glu Arg Ser Pro Val Lys Ala Arg Ser Arg Gly Gly Glu Asp Ser
    50                  55                  60

Thr Ser Arg Gly Glu Arg Ser Lys Lys Leu Gly Gly Ser Gly Ser
65                  70                  75                  80

Asn Gly Ser Ser Ser Gly Lys Thr Asp Ser Gly Gly Ser Arg Arg
            85                  90                  95

Ser Leu Leu Leu Asp Lys Ser Ser Arg Gly Ser Arg Glu Tyr
            100                 105                 110

Asp Thr Gly Gly Gly Ser Ser Ser Ser Arg Leu His Ser Tyr Ser Ser
        115                 120                 125
```

```
Pro Ser Thr Lys Asn Ser Ser Gly Gly Glu Ser Arg Ser Ser
    130                 135             140
Arg Gly Gly Gly Glu Ser Arg Ser Ser Gly Ala Ala Ser Ser Ala
145                 150             155                 160
Pro Gly Gly Gly Asp Gly Ala Glu Tyr Lys Thr Leu Lys Ile Ser Glu
                165             170             175
Leu Gly Ser Gln Leu Ser Asp Glu Ala Val Glu Asp Gly Leu Phe His
            180             185             190
Glu Phe Lys Arg Phe Gly Asp Val Ser Val Lys Ile Ser His Leu Ser
        195             200             205
Gly Ser Gly Ser Gly Asp Glu Arg Val Ala Phe Val Asn Phe Arg Arg
    210             215             220
Pro Glu Asp Ala Arg Ala Ala Lys His Ala Arg Gly Arg Leu Val Leu
225             230             235             240
Tyr Asp Arg Pro Leu Lys Ile Glu Ala Val Tyr Val Ser Arg Arg Arg
            245             250             255
Ser Arg Ser Pro Leu Asp Lys Asp Thr Tyr Pro Pro Ser Ala Ser Val
            260             265             270
Val Gly Ala Ser Val Gly Gly His Arg His Pro Gly Gly Gly Gly
        275             280             285
Gly Gln Arg Ser Leu Ser Pro Gly Gly Ala Ala Leu Gly Tyr Arg Asp
    290             295             300
Tyr Arg Leu Gln Gln Leu Ala Leu Gly Arg Leu Pro Pro Pro Pro Pro
305             310             315             320
Pro Pro Leu Pro Arg Asp Leu Glu Arg Glu Arg Asp Tyr Pro Phe Tyr
                325             330             335
Glu Arg Val Arg Pro Ala Tyr Ser Leu Glu Pro Arg Val Gly Ala Gly
            340             345             350
Ala Gly Ala Ala Pro Phe Arg Glu Val Asp Glu Ile Ser Pro Glu Asp
            355             360             365
Asp Gln Arg Ala Asn Arg Thr Leu Phe Leu Gly Asn Leu Asp Ile Thr
        370             375             380
Val Thr Glu Ser Asp Leu Arg Arg Ala Phe Asp Arg Phe Gly Val Ile
385             390             395             400
Thr Glu Val Asp Ile Lys Arg Pro Ser Arg Gly Gln Thr Ser Thr Tyr
                405             410             415
Gly Phe Leu Lys Phe Glu Asn Leu Asp Met Ser His Arg Ala Lys Leu
            420             425             430
Ala Met Ser Gly Lys Ile Ile Ile Arg Asn Pro Ile Lys Ile Gly Tyr
        435             440             445
Gly Lys Ala Thr Pro Thr Thr Arg Leu Trp Val Gly Gly Leu Gly Pro
    450             455             460
Trp Val Pro Leu Ala Ala Leu Ala Arg Glu Phe Asp Arg Phe Gly Thr
465             470             475             480
Ile Arg Thr Ile Asp Tyr Arg Lys Gly Asp Ser Trp Ala Tyr Ile Gln
                485             490             495
Tyr Glu Ser Leu Asp Ala Ala His Ala Ala Trp Thr His Met Arg Gly
            500             505             510
Phe Pro Leu Gly Gly Pro Asp Arg Arg Leu Arg Val Asp Phe Ala Asp
        515             520             525
Thr Glu His Arg Tyr Gln Gln Gln Tyr Leu Gln Pro Leu Pro Leu Thr
    530             535             540
His Tyr Glu Leu Val Thr Asp Ala Phe Gly His Arg Ala Pro Asp Pro
```

```
                                        -continued 545              550              555              560

Leu Arg Gly Ala Arg Asp Arg Thr Pro Pro Leu Leu Tyr Arg Asp Arg
                565              570              575

Asp Arg Asp Leu Tyr Pro Asp Ser Asp Trp Val Pro Pro Pro Pro Pro
            580              585              590

Val Arg Glu Arg Ser Thr Arg Thr Ala Ala Thr Ser Val Pro Ala Tyr
        595              600              605

Glu Pro Leu Asp Ser Leu Asp Arg Arg Arg Asp Gly Trp Ser Leu Asp
    610              615              620

Arg Asp Arg Gly Asp Arg Asp Leu Pro Ser Ser Arg Asp Gln Pro Arg
625              630              635              640

Lys Arg Arg Leu Pro Glu Glu Ser Gly Gly Arg His Leu Asp Arg Ser
                645              650              655

Pro Glu Ser Asp Arg Pro Arg Lys Arg His Cys Ala Pro Ser Pro Asp
            660              665              670

Arg Ser Pro Glu Leu Ser Ser Arg Asp Arg Tyr Asn Ser Asp Asn
        675              680              685

Asp Arg Ser Ser Arg Leu Leu Leu Glu Arg Pro Ser Pro Ile Arg Asp
    690              695              700

Gly Arg Gly Ser Leu Glu Lys Ser Gln Gly Asp Lys Arg Asp Arg Lys
705              710              715              720

Asn Ser Ala Ser Ala Glu Arg Asp Arg Lys His Arg Thr Thr Ala Pro
                725              730              735

Thr Glu Gly Lys Ser Pro Leu Lys Lys Glu Asp Arg Ser Asp Gly Ser
            740              745              750

Ala Pro Ser Thr Ser Thr Ala Ser Ser Lys Leu Lys Ser Pro Ser Gln
        755              760              765

Lys Gln Asp Gly Gly Thr Ala Pro Val Ala Ser Ala Ser Pro Lys Leu
    770              775              780

Cys Leu Ala Trp Gln Gly Met Leu Leu Leu Lys Asn Ser Asn Phe Pro
785              790              795              800

Ser Asn Met His Leu Leu Gln Gly Asp Leu Gln Val Ala Ser Ser Leu
                805              810              815

Leu Val Glu Gly Ser Thr Gly Gly Lys Val Ala Gln Leu Lys Ile Thr
            820              825              830

Gln Arg Leu Arg Leu Asp Gln Pro Lys Leu Asp Glu Val Thr Arg Arg
        835              840              845

Ile Lys Val Ala Gly Pro Asn Gly Tyr Ala Ile Leu Leu Ala Val Pro
    850              855              860

Gly Ser Ser Asp Ser Arg Ser Ser Ser Ser Ala Ala Ser Asp Thr
865              870              875              880

Ala Thr Ser Thr Gln Arg Pro Leu Arg Asn Leu Val Ser Tyr Leu Lys
                885              890              895

Gln Lys Gln Ala Ala Gly Val Ile Ser Leu Pro Val Gly Gly Asn Lys
            900              905              910

Asp Lys Glu Asn Thr Gly Val Leu His Ala Phe Pro Pro Cys Glu Phe
        915              920              925

Ser Gln Gln Phe Leu Asp Ser Pro Ala Lys Ala Leu Ala Lys Ser Glu
    930              935              940

Glu Asp Tyr Leu Val Met Ile Ile Val Arg Ala Lys Leu Val Glu Gln
945              950              955              960

Arg Met Lys Ile Trp Asn Ser Lys Leu
                965
```

-continued

```
<210> SEQ ID NO 9
<211> LENGTH: 3423
<212> TYPE: DNA
<213> ORGANISM: Homo sapiens
<220> FEATURE:
<221> NAME/KEY: CDS
<222> LOCATION: (84)..(3014)

<400> SEQUENCE: 9
ggcgccttcc tggagcgcgg ggagatgtaa agatagacaa ataattttcc caatgagact      60
gtagaagaga gagcaattgg cca atg agg act gcg ggg cgg gac cct gtg ccg    113
                         Met Arg Thr Ala Gly Arg Asp Pro Val Pro
                           1               5                  10 cgg cgg agt cca aga tgg cgg cgt gcg gtt ccg ctg tgt gaa acg agc      161
Arg Arg Ser Pro Arg Trp Arg Arg Ala Val Pro Leu Cys Glu Thr Ser
                 15                  20                  25 gcg ggg cgg cgg gtt act cag ctc cgc gga gac gac ctc cga cga ccc      209
Ala Gly Arg Arg Val Thr Gln Leu Arg Gly Asp Asp Leu Arg Arg Pro
             30                  35                  40 gca aca atg aag gga aaa gag cgc tcg cca gtg aag gcc aaa cgc tcc      257
Ala Thr Met Lys Gly Lys Glu Arg Ser Pro Val Lys Ala Lys Arg Ser
         45                  50                  55 cgt ggt ggt gag gac tcg act tcc cgc ggt gag cgg agc aag aag tta      305
Arg Gly Gly Glu Asp Ser Thr Ser Arg Gly Glu Arg Ser Lys Lys Leu
     60                  65                  70 ggg ggc tct ggt ggc agc aat ggg agc agc agc gga aag acc gat agc      353
Gly Gly Ser Gly Gly Ser Asn Gly Ser Ser Ser Gly Lys Thr Asp Ser
 75                  80                  85                  90 ggc ggt ggg tcg cgg cgg agt ctc ctc ctg gac aag tcc agc agt cga      401
Gly Gly Gly Ser Arg Arg Ser Leu Leu Leu Asp Lys Ser Ser Ser Arg
                 95                 100                 105 ggt ggc agc cgc gag tat gat acc ggt ggg ggc agc tcc agt agc cgc      449
Gly Gly Ser Arg Glu Tyr Asp Thr Gly Gly Gly Ser Ser Ser Ser Arg
             110                 115                 120 ttg cat agt tat agc tcc ccg agc acc aaa aat tct tcg ggc ggg ggc      497
Leu His Ser Tyr Ser Ser Pro Ser Thr Lys Asn Ser Ser Gly Gly Gly
         125                 130                 135 gag tcg cgc agc agc tcc cgg ggt gga ggc ggg gag tca cgt tcc tct      545
Glu Ser Arg Ser Ser Ser Arg Gly Gly Gly Gly Glu Ser Arg Ser Ser
     140                 145                 150 ggg gcc gcc tcc tca gct ccc ggc ggg ggg gac ggc gcg gaa tac aag      593
Gly Ala Ala Ser Ser Ala Pro Gly Gly Gly Asp Gly Ala Glu Tyr Lys
155                 160                 165                 170 act ctg aag ata agc gag ttg ggg tcc cag ctt agt gac gaa gcg gtg      641
Thr Leu Lys Ile Ser Glu Leu Gly Ser Gln Leu Ser Asp Glu Ala Val
                175                 180                 185 gag gac ggc ctg ttt cat gag ttc aaa cgc ttc ggt gat gta agt gtg      689
Glu Asp Gly Leu Phe His Glu Phe Lys Arg Phe Gly Asp Val Ser Val
            190                 195                 200 aaa atc agt cat ctg tcg ggt tct ggc agc ggg gat gag cgg gta gcc      737
Lys Ile Ser His Leu Ser Gly Ser Gly Ser Gly Asp Glu Arg Val Ala
        205                 210                 215 ttt gtg aac ttc cgg cgg cca gag gac gcg cgg gcg gcc aag cat gcc      785
Phe Val Asn Phe Arg Arg Pro Glu Asp Ala Arg Ala Ala Lys His Ala
    220                 225                 230 aga ggc cgc ctg gtg ctc tat gac cgg cct ctg aag ata gaa gct gtg      833
Arg Gly Arg Leu Val Leu Tyr Asp Arg Pro Leu Lys Ile Glu Ala Val
235                 240                 245                 250 tat gtg agc cgg cgc cgc agc cgc tcc cct tta gac aaa gat act tat      881
```

```
                        -continued

Tyr Val Ser Arg Arg Ser Arg Ser Pro Leu Asp Lys Asp Thr Tyr
            255                 260                 265 cct cca tca gcc agt gtg gtc ggg gcc tct gta ggt ggt cac cgg cac      929
Pro Pro Ser Ala Ser Val Val Gly Ala Ser Val Gly Gly His Arg His
            270                 275                 280 ccc cct gga ggt ggt gga ggc cag aga tca ctt tcc cct ggt ggc gct      977
Pro Pro Gly Gly Gly Gly Gly Gln Arg Ser Leu Ser Pro Gly Gly Ala
            285                 290                 295 gct ttg gga tac aga gac tac cgg ctg cag cag ttg gct ctt ggc cgc     1025
Ala Leu Gly Tyr Arg Asp Tyr Arg Leu Gln Gln Leu Ala Leu Gly Arg
            300                 305                 310 ctg ccc cct cca cct ccg cca cca ttg cct cga gac ctg gag aga gaa     1073
Leu Pro Pro Pro Pro Pro Pro Pro Leu Pro Arg Asp Leu Glu Arg Glu
315                 320                 325                 330 aga gac tac ccg ttc tat gag aga gtg cgc cct gca tac agt ctt gag     1121
Arg Asp Tyr Pro Phe Tyr Glu Arg Val Arg Pro Ala Tyr Ser Leu Glu
                335                 340                 345 cca agg gtg gga gct gga gca ggt gct gct cct ttc aga gaa gtg gat     1169
Pro Arg Val Gly Ala Gly Ala Gly Ala Ala Pro Phe Arg Glu Val Asp
            350                 355                 360 gag att tca ccc gag gat gat cag cga gct aac cgg acg ctc ttc ttg     1217
Glu Ile Ser Pro Glu Asp Asp Gln Arg Ala Asn Arg Thr Leu Phe Leu
            365                 370                 375 ggc aac cta gac atc act gta acg gag agt gat tta aga agg gcg ttt     1265
Gly Asn Leu Asp Ile Thr Val Thr Glu Ser Asp Leu Arg Arg Ala Phe
            380                 385                 390 gat cgc ttt gga gtc atc aca gaa gta gat atc aag agg cct tct cgc     1313
Asp Arg Phe Gly Val Ile Thr Glu Val Asp Ile Lys Arg Pro Ser Arg
395                 400                 405                 410 ggc cag act agt act tac ggc ttt ctc aaa ttt gag aac tta gat atg     1361
Gly Gln Thr Ser Thr Tyr Gly Phe Leu Lys Phe Glu Asn Leu Asp Met
                415                 420                 425 tct cac cgg gcc aaa tta gca atg tct ggc aaa att ata att cgg aat     1409
Ser His Arg Ala Lys Leu Ala Met Ser Gly Lys Ile Ile Ile Arg Asn
            430                 435                 440 cct atc aaa att ggt tat ggt aaa gct aca ccc acc acc cgc ctc tgg     1457
Pro Ile Lys Ile Gly Tyr Gly Lys Ala Thr Pro Thr Thr Arg Leu Trp
            445                 450                 455 gtg gga ggc ctg gga cct tgg gtt cct ctt gct gcc ctg gca cga gaa     1505
Val Gly Gly Leu Gly Pro Trp Val Pro Leu Ala Ala Leu Ala Arg Glu
            460                 465                 470 ttt gat cga ttt ggc acc ata cgc acc ata gac tac cga aaa ggt gat     1553
Phe Asp Arg Phe Gly Thr Ile Arg Thr Ile Asp Tyr Arg Lys Gly Asp
475                 480                 485                 490 agt tgg gca tat atc cag tat gaa agc ctg gat gca gcg cat gct gcc     1601
Ser Trp Ala Tyr Ile Gln Tyr Glu Ser Leu Asp Ala Ala His Ala Ala
                495                 500                 505 tgg acc cat atg cgg ggc ttc cca ctt ggt ggc cca gat cga cgc ctt     1649
Trp Thr His Met Arg Gly Phe Pro Leu Gly Gly Pro Asp Arg Arg Leu
            510                 515                 520 aga gta gac ttt gcc gac acc gaa cat cgt tac cag cag cag tat ctg     1697
Arg Val Asp Phe Ala Asp Thr Glu His Arg Tyr Gln Gln Gln Tyr Leu
            525                 530                 535 cag cct ctg ccc ttg act cat tat gag ctg gtg aca gat gct ttt gga     1745
Gln Pro Leu Pro Leu Thr His Tyr Glu Leu Val Thr Asp Ala Phe Gly
            540                 545                 550 cat cgg gca cca gac cct ttg agg ggt gct cgg gat agg aca cca ccc     1793
His Arg Ala Pro Asp Pro Leu Arg Gly Ala Arg Asp Arg Thr Pro Pro
555                 560                 565                 570
```

```
tta cta tac aga gat cgt gat agg gac ctt tat cct gac tct gat tgg      1841
Leu Leu Tyr Arg Asp Arg Asp Arg Asp Leu Tyr Pro Asp Ser Asp Trp
            575                 580                 585 gtg cca ccc cca ccc cca gtc cga gaa cgc agc act cgg act gca gct      1889
Val Pro Pro Pro Pro Pro Val Arg Glu Arg Ser Thr Arg Thr Ala Ala
        590                 595                 600 act tct gtg cct gct tat gag cca ctg gat agc cta gat cgc agg cgg      1937
Thr Ser Val Pro Ala Tyr Glu Pro Leu Asp Ser Leu Asp Arg Arg Arg
    605                 610                 615 gat ggt tgg tcc ttg gac cgg gac aga ggt gat cga gat ctg ccc agc      1985
Asp Gly Trp Ser Leu Asp Arg Asp Arg Gly Asp Arg Asp Leu Pro Ser
620                 625                 630 agc aga gac cag cct agg aag cga agg ctg cct gag gag agt gga gga      2033
Ser Arg Asp Gln Pro Arg Lys Arg Arg Leu Pro Glu Glu Ser Gly Gly
635                 640                 645                 650 cgt cat ctg gat agg tct cct gag agt gac cgc cca cga aaa cgt cac      2081
Arg His Leu Asp Arg Ser Pro Glu Ser Asp Arg Pro Arg Lys Arg His
                655                 660                 665 tgc gct cct tct cct gac cgc agt cca gaa ttg agc agt agc cgg gat      2129
Cys Ala Pro Ser Pro Asp Arg Ser Pro Glu Leu Ser Ser Ser Arg Asp
            670                 675                 680 cgt tac aac agc gac aat gat cga tct tcc cgt ctt ctc ttg gaa agg      2177
Arg Tyr Asn Ser Asp Asn Asp Arg Ser Ser Arg Leu Leu Leu Glu Arg
        685                 690                 695 ccc tct cca atc aga gac gga cga ggt agt ttg gag aag agc cag ggt      2225
Pro Ser Pro Ile Arg Asp Gly Arg Gly Ser Leu Glu Lys Ser Gln Gly
    700                 705                 710 gac aag cga gac cgt aaa aac tct gca tca gct gaa cga gat agg aag      2273
Asp Lys Arg Asp Arg Lys Asn Ser Ala Ser Ala Glu Arg Asp Arg Lys
715                 720                 725                 730 cac cgg aca act gct ccc act gag gga aaa agc cct ctg aaa aaa gaa      2321
His Arg Thr Thr Ala Pro Thr Glu Gly Lys Ser Pro Leu Lys Lys Glu
                735                 740                 745 gac cgc tct gat ggg agt gca cct agc acc agc act gct tcc tcc aag      2369
Asp Arg Ser Asp Gly Ser Ala Pro Ser Thr Ser Thr Ala Ser Ser Lys
            750                 755                 760 ctg aag tcc ccg tcc cag aaa cag gat ggg ggg aca gcc cct gtg gca      2417
Leu Lys Ser Pro Ser Gln Lys Gln Asp Gly Gly Thr Ala Pro Val Ala
        765                 770                 775 tca gcc tct ccc aaa ctc tgt ttg gcc tgg cag ggc atg ctt cta ctg      2465
Ser Ala Ser Pro Lys Leu Cys Leu Ala Trp Gln Gly Met Leu Leu Leu
    780                 785                 790 aag aac agc aac ttt cct tcc aac atg cat ctg ttg cag ggt gac ctc      2513
Lys Asn Ser Asn Phe Pro Ser Asn Met His Leu Leu Gln Gly Asp Leu
795                 800                 805                 810 caa gtg gct agt agt ctt ctt gtg gag ggt tca act gga ggc aaa gtg      2561
Gln Val Ala Ser Ser Leu Leu Val Glu Gly Ser Thr Gly Gly Lys Val
                815                 820                 825 gcc cag ctc aag atc act cag cgt ctc cgt ttg gac cag ccc aag ttg      2609
Ala Gln Leu Lys Ile Thr Gln Arg Leu Arg Leu Asp Gln Pro Lys Leu
            830                 835                 840 gat gaa gta act cga cgc atc aaa gta gca ggg ccc aat ggt tat gcc      2657
Asp Glu Val Thr Arg Arg Ile Lys Val Ala Gly Pro Asn Gly Tyr Ala
        845                 850                 855 att ctt ttg gct gtg cct gga agt tct gac agc cgg tcc tcc tct tcc      2705
Ile Leu Leu Ala Val Pro Gly Ser Ser Asp Ser Arg Ser Ser Ser Ser
    860                 865                 870 tca gct gca tca gac act gcc act tct act cag agg cca ctt agg aac      2753
Ser Ala Ala Ser Asp Thr Ala Thr Ser Thr Gln Arg Pro Leu Arg Asn
875                 880                 885                 890
```

```
ctt gtg tcc tat tta aag caa aag cag gca gcc ggg gtg atc agc ctc      2801
Leu Val Ser Tyr Leu Lys Gln Lys Gln Ala Ala Gly Val Ile Ser Leu
                895                 900                 905 cct gtg ggg ggc aac aaa gac aag gaa aac acc ggg gtc ctt cat gcc      2849
Pro Val Gly Gly Asn Lys Asp Lys Glu Asn Thr Gly Val Leu His Ala
            910                 915                 920 ttc cca cct tgt gag ttc tcc cag cag ttc ctg gat tcc cct gcc aag      2897
Phe Pro Pro Cys Glu Phe Ser Gln Gln Phe Leu Asp Ser Pro Ala Lys
        925                 930                 935 gca ctg gcc aaa tct gaa gaa gat tac ctg gtc atg atc att gtc cgt      2945
Ala Leu Ala Lys Ser Glu Glu Asp Tyr Leu Val Met Ile Ile Val Arg
    940                 945                 950 ggg ttt ggt ttt cag ata gga gtt agg tat gag aac aag aag aga gaa      2993
Gly Phe Gly Phe Gln Ile Gly Val Arg Tyr Glu Asn Lys Lys Arg Glu
955                 960                 965                 970 aac ttg gcg ctg acc ctg tta tagtggttat agtggtgtcc ctaaagggag         3044
Asn Leu Ala Leu Thr Leu Leu
                975 gaaatgattt cagcaaaact ggttgaacag cggatgaaga tatggaattc aaagctctaa    3104 tggaccttt  tgaagagaag ttgtggctta tgtggagttt acatgggcct ctgatggaag    3164 aaagctaatc tgtttagtat ttgtgcattt tactaaaatg gcagcttaaa gttgtgtatc    3224 tgctattgtg atgccaatgc cggtgtttta agtggaaaaa aaatgacctc tttgatttgt    3284 gctgtgtaca caagatttct ggaaaagtaa agaaaaaccc ttttatggc tcacacagct     3344 taagagtagc tgtctctcaa acgtgcgctc acagttgagc tgcttttgtt ttattctaaa    3404 taaattgttt cttttgagg                                                 3423
```

<210> SEQ ID NO 10
<211> LENGTH: 977
<212> TYPE: PRT
<213> ORGANISM: Homo sapiens

<400> SEQUENCE: 10

```
Met Arg Thr Ala Gly Arg Asp Pro Val Pro Arg Arg Ser Pro Arg Trp
1               5                   10                  15

Arg Arg Ala Val Pro Leu Cys Glu Thr Ser Ala Gly Arg Arg Val Thr
            20                  25                  30

Gln Leu Arg Gly Asp Asp Leu Arg Arg Pro Ala Thr Met Lys Gly Lys
        35                  40                  45

Glu Arg Ser Pro Val Lys Ala Lys Arg Ser Arg Gly Gly Glu Asp Ser
    50                  55                  60

Thr Ser Arg Gly Glu Arg Ser Lys Lys Leu Gly Gly Ser Gly Gly Ser
65                  70                  75                  80

Asn Gly Ser Ser Ser Gly Lys Thr Asp Ser Gly Gly Gly Ser Arg Arg
                85                  90                  95

Ser Leu Leu Leu Asp Lys Ser Ser Arg Gly Gly Ser Arg Glu Tyr
            100                 105                 110

Asp Thr Gly Gly Gly Ser Ser Ser Arg Leu His Ser Tyr Ser Ser
        115                 120                 125

Pro Ser Thr Lys Asn Ser Ser Gly Gly Glu Ser Arg Ser Ser
    130                 135                 140

Arg Gly Gly Gly Gly Glu Ser Arg Ser Ser Gly Ala Ala Ser Ala
145                 150                 155                 160

Pro Gly Gly Gly Asp Gly Ala Glu Tyr Lys Thr Leu Lys Ile Ser Glu
                165                 170                 175
```

-continued

Leu Gly Ser Gln Leu Ser Asp Glu Ala Val Glu Asp Gly Leu Phe His
            180                 185                 190

Glu Phe Lys Arg Phe Gly Asp Val Ser Val Lys Ile Ser His Leu Ser
        195                 200                 205

Gly Ser Gly Ser Gly Asp Glu Arg Val Ala Phe Val Asn Phe Arg Arg
    210                 215                 220

Pro Glu Asp Ala Arg Ala Ala Lys His Ala Arg Gly Arg Leu Val Leu
225                 230                 235                 240

Tyr Asp Arg Pro Leu Lys Ile Glu Ala Val Tyr Val Ser Arg Arg
            245                 250                 255

Ser Arg Ser Pro Leu Asp Lys Asp Thr Tyr Pro Pro Ser Ala Ser Val
        260                 265                 270

Val Gly Ala Ser Val Gly Gly His Arg His Pro Gly Gly Gly Gly
    275                 280                 285

Gly Gln Arg Ser Leu Ser Pro Gly Gly Ala Ala Leu Gly Tyr Arg Asp
    290                 295                 300

Tyr Arg Leu Gln Gln Leu Ala Leu Gly Arg Leu Pro Pro Pro Pro Pro
305                 310                 315                 320

Pro Pro Leu Pro Arg Asp Leu Glu Arg Glu Arg Asp Tyr Pro Phe Tyr
            325                 330                 335

Glu Arg Val Arg Pro Ala Tyr Ser Leu Glu Pro Arg Val Gly Ala Gly
        340                 345                 350

Ala Gly Ala Ala Pro Phe Arg Glu Val Asp Glu Ile Ser Pro Glu Asp
    355                 360                 365

Asp Gln Arg Ala Asn Arg Thr Leu Phe Leu Gly Asn Leu Asp Ile Thr
    370                 375                 380

Val Thr Glu Ser Asp Leu Arg Arg Ala Phe Asp Arg Phe Gly Val Ile
385                 390                 395                 400

Thr Glu Val Asp Ile Lys Arg Pro Ser Arg Gly Gln Thr Ser Thr Tyr
            405                 410                 415

Gly Phe Leu Lys Phe Glu Asn Leu Asp Met Ser His Arg Ala Lys Leu
        420                 425                 430

Ala Met Ser Gly Lys Ile Ile Arg Asn Pro Ile Lys Ile Gly Tyr
    435                 440                 445

Gly Lys Ala Thr Pro Thr Thr Arg Leu Trp Val Gly Gly Leu Gly Pro
    450                 455                 460

Trp Val Pro Leu Ala Ala Leu Ala Arg Glu Phe Asp Arg Phe Gly Thr
465                 470                 475                 480

Ile Arg Thr Ile Asp Tyr Arg Lys Gly Asp Ser Trp Ala Tyr Ile Gln
            485                 490                 495

Tyr Glu Ser Leu Asp Ala Ala His Ala Ala Trp Thr His Met Arg Gly
        500                 505                 510

Phe Pro Leu Gly Gly Pro Asp Arg Arg Leu Arg Val Asp Phe Ala Asp
    515                 520                 525

Thr Glu His Arg Tyr Gln Gln Gln Tyr Leu Gln Pro Leu Pro Leu Thr
    530                 535                 540

His Tyr Glu Leu Val Thr Asp Ala Phe Gly His Arg Ala Pro Asp Pro
545                 550                 555                 560

Leu Arg Gly Ala Arg Asp Arg Thr Pro Pro Leu Leu Tyr Arg Asp Arg
            565                 570                 575

Asp Arg Asp Leu Tyr Pro Asp Ser Asp Trp Val Pro Pro Pro Pro
        580                 585                 590

```
Val Arg Glu Arg Ser Thr Arg Thr Ala Ala Thr Ser Val Pro Ala Tyr
        595                 600                 605

Glu Pro Leu Asp Ser Leu Asp Arg Arg Asp Gly Trp Ser Leu Asp
        610                 615                 620

Arg Asp Arg Gly Asp Arg Asp Leu Pro Ser Ser Arg Asp Gln Pro Arg
625                 630                 635                 640

Lys Arg Arg Leu Pro Glu Glu Ser Gly Gly Arg His Leu Asp Arg Ser
                645                 650                 655

Pro Glu Ser Asp Arg Pro Arg Lys Arg His Cys Ala Pro Ser Pro Asp
                660                 665                 670

Arg Ser Pro Glu Leu Ser Ser Arg Asp Arg Tyr Asn Ser Asp Asn
        675                 680                 685

Asp Arg Ser Ser Arg Leu Leu Leu Glu Arg Pro Ser Pro Ile Arg Asp
        690                 695                 700

Gly Arg Gly Ser Leu Glu Lys Ser Gln Gly Asp Lys Arg Asp Arg Lys
705                 710                 715                 720

Asn Ser Ala Ser Ala Glu Arg Asp Arg Lys His Arg Thr Thr Ala Pro
                725                 730                 735

Thr Glu Gly Lys Ser Pro Leu Lys Lys Glu Asp Arg Ser Asp Gly Ser
                740                 745                 750

Ala Pro Ser Thr Ser Thr Ala Ser Ser Lys Leu Lys Ser Pro Ser Gln
        755                 760                 765

Lys Gln Asp Gly Gly Thr Ala Pro Val Ala Ser Ala Ser Pro Lys Leu
        770                 775                 780

Cys Leu Ala Trp Gln Gly Met Leu Leu Lys Asn Ser Asn Phe Pro
785                 790                 795                 800

Ser Asn Met His Leu Leu Gln Gly Asp Leu Gln Val Ala Ser Ser Leu
                805                 810                 815

Leu Val Glu Gly Ser Thr Gly Gly Lys Val Ala Gln Leu Lys Ile Thr
                820                 825                 830

Gln Arg Leu Arg Leu Asp Gln Pro Lys Leu Asp Glu Val Thr Arg Arg
        835                 840                 845

Ile Lys Val Ala Gly Pro Asn Gly Tyr Ala Ile Leu Ala Val Pro
850                 855                 860

Gly Ser Ser Asp Ser Arg Ser Ser Ser Ser Ala Ala Ser Asp Thr
865                 870                 875                 880

Ala Thr Ser Thr Gln Arg Pro Leu Arg Asn Leu Val Ser Tyr Leu Lys
                885                 890                 895

Gln Lys Gln Ala Ala Gly Val Ile Ser Leu Pro Val Gly Gly Asn Lys
        900                 905                 910

Asp Lys Glu Asn Thr Gly Val Leu His Ala Phe Pro Pro Cys Glu Phe
        915                 920                 925

Ser Gln Gln Phe Leu Asp Ser Pro Ala Lys Ala Leu Ala Lys Ser Glu
930                 935                 940

Glu Asp Tyr Leu Val Met Ile Ile Val Arg Gly Phe Gly Phe Gln Ile
945                 950                 955                 960

Gly Val Arg Tyr Glu Asn Lys Lys Arg Glu Asn Leu Ala Leu Thr Leu
                965                 970                 975

Leu

<210> SEQ ID NO 11
<211> LENGTH: 3383
<212> TYPE: DNA
<213> ORGANISM: Homo sapiens
```

```
<220> FEATURE:
<221> NAME/KEY: CDS
<222> LOCATION: (84)..(2954)

<400> SEQUENCE: 11
ggcgccttcc tggagcgcgg ggagatgtaa agatagacaa ataattttcc caatgagact      60
gtagaagaga gagcaattgg cca atg agg act gcg ggg cgg gac cct gtg ccg     113
                         Met Arg Thr Ala Gly Arg Asp Pro Val Pro
                          1               5                  10 cgg cgg agt cca aga tgg cgg cgt gcg gtt ccg ctg tgt gaa acg agc      161
Arg Arg Ser Pro Arg Trp Arg Arg Ala Val Pro Leu Cys Glu Thr Ser
             15                  20                  25 gcg ggg cgg cgg gtt act cag ctc cgc gga gac gac ctc cga cga ccc      209
Ala Gly Arg Arg Val Thr Gln Leu Arg Gly Asp Asp Leu Arg Arg Pro
         30                  35                  40 gca aca atg aag gga aaa gag cgc tcg cca gtg aag gcc aaa cgc tcc      257
Ala Thr Met Lys Gly Lys Glu Arg Ser Pro Val Lys Ala Lys Arg Ser
     45                  50                  55 cgt ggt ggt gag gac tcg act tcc cgc ggt gag cgg agc aag aag tta      305
Arg Gly Gly Glu Asp Ser Thr Ser Arg Gly Glu Arg Ser Lys Lys Leu
 60                  65                  70 ggg ggc tct ggt ggc agc aat ggg agc agc agc gga aag acc gat agc      353
Gly Gly Ser Gly Gly Ser Asn Gly Ser Ser Ser Gly Lys Thr Asp Ser
 75                  80                  85                  90 ggc ggt ggg tcg cgg cgg agt ctc ctc ctg gac aag tcc agc agt cga      401
Gly Gly Gly Ser Arg Arg Ser Leu Leu Leu Asp Lys Ser Ser Ser Arg
                 95                 100                 105 ggt ggc agc cgc gag tat gat acc ggt ggg ggc agc tcc agt agc cgc      449
Gly Gly Ser Arg Glu Tyr Asp Thr Gly Gly Gly Ser Ser Ser Ser Arg
             110                 115                 120 ttg cat agt tat agc tcc ccg agc acc aaa aat tct tcg ggc ggg ggc      497
Leu His Ser Tyr Ser Ser Pro Ser Thr Lys Asn Ser Ser Gly Gly Gly
         125                 130                 135 gag tcg cgc agc agc tcc cgg ggt gga ggc ggg gag tca cgt tcc tct      545
Glu Ser Arg Ser Ser Ser Arg Gly Gly Gly Gly Glu Ser Arg Ser Ser
     140                 145                 150 ggg gcc gcc tcc tca gct ccc ggc ggc ggg gac ggc gcg gaa tac aag      593
Gly Ala Ala Ser Ser Ala Pro Gly Gly Gly Asp Gly Ala Glu Tyr Lys
155                 160                 165                 170 act ctg aag ata agc gag ttg ggg tcc cag ctt agt gac gaa gcg gtg      641
Thr Leu Lys Ile Ser Glu Leu Gly Ser Gln Leu Ser Asp Glu Ala Val
                 175                 180                 185 gag gac ggc ctg ttt cat gag ttc aaa cgc ttc ggt gat gta agt gtg      689
Glu Asp Gly Leu Phe His Glu Phe Lys Arg Phe Gly Asp Val Ser Val
             190                 195                 200 aaa atc agt cat ctg tcg ggt tct ggc agc ggg gat gag cgg gta gcc      737
Lys Ile Ser His Leu Ser Gly Ser Gly Ser Gly Asp Glu Arg Val Ala
         205                 210                 215 ttt gtg aac ttc cgg cgg cca gag gac gcg cgg gcg gcc aag cat gcc      785
Phe Val Asn Phe Arg Arg Pro Glu Asp Ala Arg Ala Ala Lys His Ala
     220                 225                 230 aga ggc cgc ctg gtg ctc tat gac cgg cct ctg aag ata gaa gct gtg      833
Arg Gly Arg Leu Val Leu Tyr Asp Arg Pro Leu Lys Ile Glu Ala Val
235                 240                 245                 250 tat gtg agc cgg cgc cgc agc cgc tcc cct tta gac aaa gat act tat      881
Tyr Val Ser Arg Arg Arg Ser Arg Ser Pro Leu Asp Lys Asp Thr Tyr
                 255                 260                 265 cct cca tca gcc agt gtg gtc ggg gcc tct gta ggt ggt cac cgg cac      929
Pro Pro Ser Ala Ser Val Val Gly Ala Ser Val Gly Gly His Arg His
             270                 275                 280
```

-continued

| | |
|---|---|
| ccc cct gga ggt ggt gga ggc cag aga tca ctt tcc cct ggt ggc gct<br>Pro Pro Gly Gly Gly Gly Gly Gln Arg Ser Leu Ser Pro Gly Gly Ala<br>285                                  290                               295 | 977 |
| gct ttg gga tac aga gac tac cgg ctg cag cag ttg gct ctt ggc cgc<br>Ala Leu Gly Tyr Arg Asp Tyr Arg Leu Gln Gln Leu Ala Leu Gly Arg<br>300                                  305                               310 | 1025 |
| ctg ccc cct cca cct ccg cca cca ttg cct cga gac ctg gag aga gaa<br>Leu Pro Pro Pro Pro Pro Pro Pro Leu Pro Arg Asp Leu Glu Arg Glu<br>315                                  320                           325                   330 | 1073 |
| aga gac tac ccg ttc tat gag aga gtg cgc cct gca tac agt ctt gag<br>Arg Asp Tyr Pro Phe Tyr Glu Arg Val Arg Pro Ala Tyr Ser Leu Glu<br>                       335                              340                           345 | 1121 |
| cca agg gtg gga gct gga gca ggt gct gct cct ttc aga gaa gtg gat<br>Pro Arg Val Gly Ala Gly Ala Gly Ala Ala Pro Phe Arg Glu Val Asp<br>350                                  355                           360 | 1169 |
| gag att tca ccc gag gat gat cag cga gct aac cgg acg ctc ttc ttg<br>Glu Ile Ser Pro Glu Asp Asp Gln Arg Ala Asn Arg Thr Leu Phe Leu<br>                       365                              370                           375 | 1217 |
| ggc aac cta gac atc act gta acg gag agt gat tta aga agg gcg ttt<br>Gly Asn Leu Asp Ile Thr Val Thr Glu Ser Asp Leu Arg Arg Ala Phe<br>380                                  385                           390 | 1265 |
| gat cgc ttt gga gtc atc aca gaa gta gat atc aag agg cct tct cgc<br>Asp Arg Phe Gly Val Ile Thr Glu Val Asp Ile Lys Arg Pro Ser Arg<br>395                                  400                           405                   410 | 1313 |
| ggc cag act agt act tac ggc ttt ctc aaa ttt gag aac tta gat atg<br>Gly Gln Thr Ser Thr Tyr Gly Phe Leu Lys Phe Glu Asn Leu Asp Met<br>                       415                              420                           425 | 1361 |
| tct cac cgg gcc aaa tta gca atg tct ggc aaa att ata att cgg aat<br>Ser His Arg Ala Lys Leu Ala Met Ser Gly Lys Ile Ile Ile Arg Asn<br>430                                  435                           440 | 1409 |
| cct atc aaa att ggt tat ggt aaa gct aca ccc acc acc cgc ctc tgg<br>Pro Ile Lys Ile Gly Tyr Gly Lys Ala Thr Pro Thr Thr Arg Leu Trp<br>                       445                              450                           455 | 1457 |
| gtg gga ggc ctg gga cct tgg gtt cct ctt gct gcc ctg gca cga gaa<br>Val Gly Gly Leu Gly Pro Trp Val Pro Leu Ala Ala Leu Ala Arg Glu<br>460                                  465                           470 | 1505 |
| ttt gat cga ttt ggc acc ata cgc acc ata gac tac cga aaa ggt gat<br>Phe Asp Arg Phe Gly Thr Ile Arg Thr Ile Asp Tyr Arg Lys Gly Asp<br>475                                  480                           485                   490 | 1553 |
| agt tgg gca tat atc cag tat gaa agc ctg gat gca gcg cat gct gcc<br>Ser Trp Ala Tyr Ile Gln Tyr Glu Ser Leu Asp Ala Ala His Ala Ala<br>                       495                              500                           505 | 1601 |
| tgg acc cat atg cgg ggc ttc cca ctt ggt ggc cca gat cga cgc ctt<br>Trp Thr His Met Arg Gly Phe Pro Leu Gly Gly Pro Asp Arg Arg Leu<br>510                                  515                           520 | 1649 |
| aga gta gac ttt gcc gac acc gaa cat cgt tac cag cag cag tat ctg<br>Arg Val Asp Phe Ala Asp Thr Glu His Arg Tyr Gln Gln Gln Tyr Leu<br>                       525                              530                           535 | 1697 |
| cag cct ctg ccc ttg act cat tat gag ctg gtg aca gat gct ttt gga<br>Gln Pro Leu Pro Leu Thr His Tyr Glu Leu Val Thr Asp Ala Phe Gly<br>540                                  545                           550 | 1745 |
| cat cgg gca cca gac cct ttg agg ggt gct cgg gat agg aca cca ccc<br>His Arg Ala Pro Asp Pro Leu Arg Gly Ala Arg Asp Arg Thr Pro Pro<br>555                                  560                           565                   570 | 1793 |
| tta cta tac aga gat cgt gat agg gac ctt tat cct gac tct gat tgg<br>Leu Leu Tyr Arg Asp Arg Asp Arg Asp Leu Tyr Pro Asp Ser Asp Trp<br>                       575                              580                           585 | 1841 |
| gtg cca ccc cca ccc cca gtc cga gaa cgc agc act cgg act gca gct<br>Val Pro Pro Pro Pro Pro Val Arg Glu Arg Ser Thr Arg Thr Ala Ala | 1889 |

-continued

|     |     |     |     | 590 |     |     |     |     | 595 |     |     |     |     | 600 |     |      |
|-----|-----|-----|-----|-----|-----|-----|-----|-----|-----|-----|-----|-----|-----|-----|-----|------|
| act | tct | gtg | cct | gct | tat | gag | cca | ctg | gat | agc | cta | gat | cgc | agg | cgg | 1937 |
| Thr | Ser | Val | Pro | Ala | Tyr | Glu | Pro | Leu | Asp | Ser | Leu | Asp | Arg | Arg | Arg |      |
|     |     | 605 |     |     |     | 610 |     |     |     | 615 |     |     |     |     |     |      |

```
gat ggt tgg tcc ttg gac cgg gac aga ggt gat cga gat ctg ccc agc      1985
Asp Gly Trp Ser Leu Asp Arg Asp Arg Gly Asp Arg Asp Leu Pro Ser
        620                 625                 630 agc aga gac cag cct agg aag cga agg ctg cct gag gag agt gga gga      2033
Ser Arg Asp Gln Pro Arg Lys Arg Arg Leu Pro Glu Glu Ser Gly Gly
635                 640                 645                 650 cgt cat ctg gat agg tct cct gag agt gac cgc cca cga aaa cgt cac      2081
Arg His Leu Asp Arg Ser Pro Glu Ser Asp Arg Pro Arg Lys Arg His
                    655                 660                 665 tgc gct cct tct cct gac cgc agt cca gaa ttg agc agt agc cgg gat      2129
Cys Ala Pro Ser Pro Asp Arg Ser Pro Glu Leu Ser Ser Ser Arg Asp
                670                 675                 680 cgt tac aac agc gac aat gat cga tct tcc cgt ctt ctc ttg gaa agg      2177
Arg Tyr Asn Ser Asp Asn Asp Arg Ser Ser Arg Leu Leu Leu Glu Arg
            685                 690                 695 ccc tct cca atc aga gac gga cga ggt agt ttg gag aag agc cag ggt      2225
Pro Ser Pro Ile Arg Asp Gly Arg Gly Ser Leu Glu Lys Ser Gln Gly
700                 705                 710 gac aag cga gac cgt aaa aac tct gca tca gct gaa cga gat agg aag      2273
Asp Lys Arg Asp Arg Lys Asn Ser Ala Ser Ala Glu Arg Asp Arg Lys
715                 720                 725                 730 cac cgg aca act gct ccc act gag gga aaa agc cct ctg aaa aaa gaa      2321
His Arg Thr Thr Ala Pro Thr Glu Gly Lys Ser Pro Leu Lys Lys Glu
                    735                 740                 745 gac cgc tct gat ggg agt gca cct agc acc agc act gct tcc tcc aag      2369
Asp Arg Ser Asp Gly Ser Ala Pro Ser Thr Ser Thr Ala Ser Ser Lys
                750                 755                 760 ctg aag tcc ccg tcc cag aaa cag gat ggg ggg aca gcc cct gtg gca      2417
Leu Lys Ser Pro Ser Gln Lys Gln Asp Gly Gly Thr Ala Pro Val Ala
            765                 770                 775 tca gcc tct ccc aaa ctc tgt ttg gcc tgg cag ggc atg ctt cta ctg      2465
Ser Ala Ser Pro Lys Leu Cys Leu Ala Trp Gln Gly Met Leu Leu Leu
780                 785                 790 aag aac agc aac ttt cct tcc aac atg cat ctg ttg cag ggt gac ctc      2513
Lys Asn Ser Asn Phe Pro Ser Asn Met His Leu Leu Gln Gly Asp Leu
795                 800                 805                 810 caa gtg gct agt agt ctt ctt gtg gag ggt tca act gga ggc aaa gtg      2561
Gln Val Ala Ser Ser Leu Leu Val Glu Gly Ser Thr Gly Gly Lys Val
                    815                 820                 825 gcc cag ctc aag atc act cag cgt ctc cgt ttg gac cag ccc aag ttg      2609
Ala Gln Leu Lys Ile Thr Gln Arg Leu Arg Leu Asp Gln Pro Lys Leu
                830                 835                 840 gat gaa gta act cga cgc atc aaa gta gca ggg ccc aat ggt tat gcc      2657
Asp Glu Val Thr Arg Arg Ile Lys Val Ala Gly Pro Asn Gly Tyr Ala
            845                 850                 855 att ctt ttg gct gtg cct gga agt tct gac agc cgg tcc tcc tct tcc      2705
Ile Leu Leu Ala Val Pro Gly Ser Ser Asp Ser Arg Ser Ser Ser Ser
860                 865                 870 tca gct gca tca gac act gcc act tct act cag agg cca ctt agg aac      2753
Ser Ala Ala Ser Asp Thr Ala Thr Ser Thr Gln Arg Pro Leu Arg Asn
875                 880                 885                 890 ctt gtg tcc tat tta aag caa aag cag gca gcc ggg gtg atc agc ctc      2801
Leu Val Ser Tyr Leu Lys Gln Lys Gln Ala Ala Gly Val Ile Ser Leu
                    895                 900                 905 cct gtg ggg ggc aac aaa gac aag gaa aac acc ggg gtc ctt cat gcc      2849
```

```
Pro Val Gly Gly Asn Lys Asp Lys Glu Asn Thr Gly Val Leu His Ala
            910                 915                 920 ttc cca cct tgt gag ttc tcc cag cag ttc ctg gat tcc cct gcc aag      2897
Phe Pro Pro Cys Glu Phe Ser Gln Gln Phe Leu Asp Ser Pro Ala Lys
        925                 930                 935 gca ctg gcc aaa tct gaa gaa gat tac ctg gtc atg atc att gtc cgt      2945
Ala Leu Ala Lys Ser Glu Glu Asp Tyr Leu Val Met Ile Ile Val Arg
        940                 945                 950 ggt gcg tcc taaagtccgt gtgtaacttg tatttactac tttgacatgg              2994
Gly Ala Ser
955 ttcctgttttt gtgatgtgta atggatacag catcagatgc aattttcttt ttagttgtta   3054
gttgtagcat tttctttttt atatttttat aaacgtcttt aaaatagaaa tcaggacagt    3114
ttagctattt ttttgtttgt ttagctatta ttttaagtga aagggatgcc ctaaaggtag    3174
caggcaggca gacagatttg ctttaattag gagttcccac ccttatgagt aattttttt     3234 ctctattcag ttgttttttt tttaatcttg agcttaaaaa atcctcagag ttacaaaacc    3294
aaaattttga aaagtcagaa tttggagaaa ggagtccact gaccatataa agagagtaat    3354
agccacctaa aaaaaaaaaa aaaaaaaaa                                      3383
```

<210> SEQ ID NO 12
<211> LENGTH: 957
<212> TYPE: PRT
<213> ORGANISM: Homo sapiens

<400> SEQUENCE: 12

```
Met Arg Thr Ala Gly Arg Asp Pro Val Pro Arg Arg Ser Pro Arg Trp
1               5                   10                  15

Arg Arg Ala Val Pro Leu Cys Glu Thr Ser Ala Gly Arg Arg Val Thr
            20                  25                  30

Gln Leu Arg Gly Asp Asp Leu Arg Arg Pro Ala Thr Met Lys Gly Lys
        35                  40                  45

Glu Arg Ser Pro Val Lys Ala Lys Arg Ser Arg Gly Gly Glu Asp Ser
    50                  55                  60

Thr Ser Arg Gly Glu Arg Ser Lys Lys Leu Gly Ser Gly Gly Ser
65                  70                  75                  80

Asn Gly Ser Ser Ser Gly Lys Thr Asp Ser Gly Gly Ser Arg Arg
                85                  90                  95

Ser Leu Leu Leu Asp Lys Ser Ser Arg Gly Gly Ser Arg Glu Tyr
            100                 105                 110

Asp Thr Gly Gly Gly Ser Ser Ser Arg Leu His Ser Tyr Ser Ser
        115                 120                 125

Pro Ser Thr Lys Asn Ser Ser Gly Gly Glu Ser Arg Ser Ser Ser
    130                 135                 140

Arg Gly Gly Gly Glu Ser Arg Ser Gly Ala Ala Ser Ser Ala
145                 150                 155                 160

Pro Gly Gly Gly Asp Gly Ala Glu Tyr Lys Thr Leu Lys Ile Ser Glu
                165                 170                 175

Leu Gly Ser Gln Leu Ser Asp Glu Ala Val Glu Asp Gly Leu Phe His
            180                 185                 190

Glu Phe Lys Arg Phe Gly Asp Val Ser Val Lys Ile Ser His Leu Ser
        195                 200                 205

Gly Ser Gly Ser Gly Asp Glu Arg Val Ala Phe Val Asn Phe Arg Arg
    210                 215                 220
```

-continued

```
Pro Glu Asp Ala Arg Ala Ala Lys His Ala Arg Gly Arg Leu Val Leu
225                 230                 235                 240

Tyr Asp Arg Pro Leu Lys Ile Glu Ala Val Tyr Val Ser Arg Arg Arg
                245                 250                 255

Ser Arg Ser Pro Leu Asp Lys Asp Thr Tyr Pro Pro Ser Ala Ser Val
            260                 265                 270

Val Gly Ala Ser Val Gly Gly His Arg His Pro Pro Gly Gly Gly Gly
        275                 280                 285

Gly Gln Arg Ser Leu Ser Pro Gly Gly Ala Ala Leu Gly Tyr Arg Asp
    290                 295                 300

Tyr Arg Leu Gln Gln Leu Ala Leu Gly Arg Leu Pro Pro Pro Pro Pro
305                 310                 315                 320

Pro Pro Leu Pro Arg Asp Leu Glu Arg Glu Arg Asp Tyr Pro Phe Tyr
                325                 330                 335

Glu Arg Val Arg Pro Ala Tyr Ser Leu Glu Pro Arg Val Gly Ala Gly
            340                 345                 350

Ala Gly Ala Ala Pro Phe Arg Glu Val Asp Glu Ile Ser Pro Glu Asp
        355                 360                 365

Asp Gln Arg Ala Asn Arg Thr Leu Phe Leu Gly Asn Leu Asp Ile Thr
    370                 375                 380

Val Thr Glu Ser Asp Leu Arg Arg Ala Phe Asp Arg Phe Gly Val Ile
385                 390                 395                 400

Thr Glu Val Asp Ile Lys Arg Pro Ser Arg Gly Gln Thr Ser Thr Tyr
                405                 410                 415

Gly Phe Leu Lys Phe Glu Asn Leu Asp Met Ser His Arg Ala Lys Leu
            420                 425                 430

Ala Met Ser Gly Lys Ile Ile Ile Arg Asn Pro Ile Lys Ile Gly Tyr
        435                 440                 445

Gly Lys Ala Thr Pro Thr Thr Arg Leu Trp Val Gly Gly Leu Gly Pro
    450                 455                 460

Trp Val Pro Leu Ala Ala Leu Ala Arg Glu Phe Asp Arg Phe Gly Thr
465                 470                 475                 480

Ile Arg Thr Ile Asp Tyr Arg Lys Gly Asp Ser Trp Ala Tyr Ile Gln
                485                 490                 495

Tyr Glu Ser Leu Asp Ala Ala His Ala Ala Trp Thr His Met Arg Gly
            500                 505                 510

Phe Pro Leu Gly Gly Pro Asp Arg Arg Leu Arg Val Asp Phe Ala Asp
        515                 520                 525

Thr Glu His Arg Tyr Gln Gln Gln Tyr Leu Gln Pro Leu Pro Leu Thr
    530                 535                 540

His Tyr Glu Leu Val Thr Asp Ala Phe Gly His Arg Ala Pro Asp Pro
545                 550                 555                 560

Leu Arg Gly Ala Arg Asp Arg Thr Pro Pro Leu Leu Tyr Arg Asp Arg
                565                 570                 575

Asp Arg Asp Leu Tyr Pro Asp Ser Asp Trp Val Pro Pro Pro Pro
            580                 585                 590

Val Arg Glu Arg Ser Thr Arg Thr Ala Ala Thr Ser Val Pro Ala Tyr
        595                 600                 605

Glu Pro Leu Asp Ser Leu Asp Arg Arg Asp Gly Trp Ser Leu Asp
    610                 615                 620

Arg Asp Arg Gly Asp Arg Asp Leu Pro Ser Ser Arg Asp Gln Pro Arg
625                 630                 635                 640

Lys Arg Arg Leu Pro Glu Glu Ser Gly Gly Arg His Leu Asp Arg Ser
```

```
                    645                 650                 655
    Pro Glu Ser Asp Arg Pro Arg Lys Arg His Cys Ala Pro Ser Pro Asp
                660                 665                 670

Arg Ser Pro Glu Leu Ser Ser Ser Arg Asp Arg Tyr Asn Ser Asp Asn
                675                 680                 685

Asp Arg Ser Ser Arg Leu Leu Leu Glu Arg Pro Ser Pro Ile Arg Asp
                690                 695                 700

Gly Arg Gly Ser Leu Glu Lys Ser Gln Gly Asp Lys Arg Asp Arg Lys
    705                 710                 715                 720

Asn Ser Ala Ser Ala Glu Arg Asp Arg Lys His Arg Thr Thr Ala Pro
                    725                 730                 735

Thr Glu Gly Lys Ser Pro Leu Lys Lys Glu Asp Arg Ser Asp Gly Ser
                740                 745                 750

Ala Pro Ser Thr Ser Thr Ala Ser Ser Lys Leu Lys Ser Pro Ser Gln
                755                 760                 765

Lys Gln Asp Gly Gly Thr Ala Pro Val Ala Ser Ala Pro Lys Leu
                770                 775                 780

Cys Leu Ala Trp Gln Gly Met Leu Leu Lys Asn Ser Asn Phe Pro
    785                 790                 795                 800

Ser Asn Met His Leu Leu Gln Gly Asp Leu Gln Val Ala Ser Leu
                    805                 810                 815

Leu Val Glu Gly Ser Thr Gly Gly Lys Val Ala Gln Leu Lys Ile Thr
                820                 825                 830

Gln Arg Leu Arg Leu Asp Gln Pro Lys Leu Asp Glu Val Thr Arg Arg
                835                 840                 845

Ile Lys Val Ala Gly Pro Asn Gly Tyr Ala Ile Leu Leu Ala Val Pro
    850                 855                 860

Gly Ser Ser Asp Ser Arg Ser Ser Ser Ser Ala Ala Ser Asp Thr
    865                 870                 875                 880

Ala Thr Ser Thr Gln Arg Pro Leu Arg Asn Leu Val Ser Tyr Leu Lys
                    885                 890                 895

Gln Lys Gln Ala Ala Gly Val Ile Ser Leu Pro Val Gly Gly Asn Lys
                900                 905                 910

Asp Lys Glu Asn Thr Gly Val Leu His Ala Phe Pro Pro Cys Glu Phe
                915                 920                 925

Ser Gln Gln Phe Leu Asp Ser Pro Ala Lys Ala Leu Ala Lys Ser Glu
    930                 935                 940

Glu Asp Tyr Leu Val Met Ile Ile Val Arg Gly Ala Ser
    945                 950                 955

<210> SEQ ID NO 13
<211> LENGTH: 4447
<212> TYPE: DNA
<213> ORGANISM: Homo sapiens
<220> FEATURE:
<221> NAME/KEY: CDS
<222> LOCATION: (551)..(3346)

<400> SEQUENCE: 13 tcccatctttt cccaccctct tggttgccgc tggccacacg ccctccgctg gcggcgactt      60
ctcagctccg tgcgcccggg ctggacagtg agcctcgaga ggagacgcgg gcggctagag     120
ccggagtggg gcgagccgcg gaacccggcc gggagccgcg cgaggcgtga tcggagggta     180
tggttggcat ggaattgaat tcatctgtc tgtgggaatt gtaagcaaga ttgccatcac      240
gaaagccaaa gtggatttct ccagtgtggt gtgcctgccc ccttccgtca ttgctgtgaa     300
```

```
tgggctggac ggaggagggg ccggcgaaaa tgatgatgaa ccagtgctcg tgtccttatc    360
tgcggcaccc agtccccaga gtgaagctgt tgccaatgaa ctgcaggagc tctccttgca    420
gcccgagctg accctaggcc tccaccctgg caggaatccc aatttgcctc cacttagtga    480
gcggaagaat gtgctacagt tgaaactcca gcagcgccgg acccgggaag aactggtgag    540
ccaagggatc atg ccg cct ttg aaa agt cca gcc gca ttt cat gag cag        589
            Met Pro Pro Leu Lys Ser Pro Ala Ala Phe His Glu Gln
              1               5                   10 aga agg agc ttg gag cgg gcc agg aca gag gac tat ctc aaa cgg aag        637
Arg Arg Ser Leu Glu Arg Ala Arg Thr Glu Asp Tyr Leu Lys Arg Lys
         15                  20                  25 att cgt tcc cgg ccg gag aga tcg gag ctg gtc agg atg cac att ttg        685
Ile Arg Ser Arg Pro Glu Arg Ser Glu Leu Val Arg Met His Ile Leu
 30                  35                  40                  45 gaa gag acc tcg gct gag cca tcc ctc cag gcc aag cag ctg aag ctg        733
Glu Glu Thr Ser Ala Glu Pro Ser Leu Gln Ala Lys Gln Leu Lys Leu
                 50                  55                  60 aag aga gcc aga cta gcc gat gac ctc aat gag aag att gca cag agg        781
Lys Arg Ala Arg Leu Ala Asp Asp Leu Asn Glu Lys Ile Ala Gln Arg
             65                  70                  75 cct ggc ccc atg gag ctg gtg gag aag aac atc ctt cct gtt gag tcc        829
Pro Gly Pro Met Glu Leu Val Glu Lys Asn Ile Leu Pro Val Glu Ser
         80                  85                  90 agc ctg aag gaa gcc atc att gtg ggc cag gtg aac tat ccc aaa gta        877
Ser Leu Lys Glu Ala Ile Ile Val Gly Gln Val Asn Tyr Pro Lys Val
     95                 100                 105 gca gac agc tct tcc ttc gat gag gac agc agc gat gcc tta tcc ccc        925
Ala Asp Ser Ser Ser Phe Asp Glu Asp Ser Ser Asp Ala Leu Ser Pro
110                 115                 120                 125 gag cag cct gcc agc cat gag tcc cag ggt tct gtg ccg tca ccc ctg        973
Glu Gln Pro Ala Ser His Glu Ser Gln Gly Ser Val Pro Ser Pro Leu
                130                 135                 140 gag gcc cga gtc agc gaa cca ctg ctc agt gcc acc tct gca tcc ccc       1021
Glu Ala Arg Val Ser Glu Pro Leu Leu Ser Ala Thr Ser Ala Ser Pro
            145                 150                 155 acc cag gtt gtg tct caa ctt ccg atg ggc cgg gat tcc aga gaa atg       1069
Thr Gln Val Val Ser Gln Leu Pro Met Gly Arg Asp Ser Arg Glu Met
        160                 165                 170 ctt ttc ctg gca gag cag cct cct ctg cct ccc cca cct ctg ctg cct       1117
Leu Phe Leu Ala Glu Gln Pro Pro Leu Pro Pro Pro Leu Leu Pro
    175                 180                 185 ccc agc ctc acc aat gga acc act atc ccc act gcc aag tcc acc ccc       1165
Pro Ser Leu Thr Asn Gly Thr Thr Ile Pro Thr Ala Lys Ser Thr Pro
190                 195                 200                 205 aca ctc att aag caa agc caa ccc aag tct gcc agt gag aag tca cag       1213
Thr Leu Ile Lys Gln Ser Gln Pro Lys Ser Ala Ser Glu Lys Ser Gln
                210                 215                 220 cgc agc aag aag gcc aag gag ctg aag cca aag gtg aag aag ctc aag       1261
Arg Ser Lys Lys Ala Lys Glu Leu Lys Pro Lys Val Lys Lys Leu Lys
            225                 230                 235 tac cac cag tac atc ccc ccg gac cag aag cag gac agg ggg gca ccc       1309
Tyr His Gln Tyr Ile Pro Pro Asp Gln Lys Gln Asp Arg Gly Ala Pro
        240                 245                 250 ccc atg gac tca tcc tac gcc aag atc ctg cag cag cag cag ctc ttc       1357
Pro Met Asp Ser Ser Tyr Ala Lys Ile Leu Gln Gln Gln Gln Leu Phe
255                 260                 265 ctc cag ctg cag atc ctc aac cag cag cag cag cag cac cac aac tac       1405
Leu Gln Leu Gln Ile Leu Asn Gln Gln Gln Gln Gln His His Asn Tyr
```

```
                 270                   275                   280                   285
cag gcc atc ctg cct gcc ccg cca aag tca gca ggc gag gcc ctg gga    1453
Gln Ala Ile Leu Pro Ala Pro Pro Lys Ser Ala Gly Glu Ala Leu Gly
                 290                   295                   300 agc agc ggg acc ccc cca gta cgc agc ctc tcc act acc aat agc agc    1501
Ser Ser Gly Thr Pro Pro Val Arg Ser Leu Ser Thr Thr Asn Ser Ser
        305                   310                   315 tcc agc tcg ggc gcc cct ggg ccc tgt ggg ctg gca cgt cag aac agc    1549
Ser Ser Ser Gly Ala Pro Gly Pro Cys Gly Leu Ala Arg Gln Asn Ser
        320                   325                   330 acc tca ctg act ggc aag ccg gga gcc ctg ccg gcc aac ctg gac gac    1597
Thr Ser Leu Thr Gly Lys Pro Gly Ala Leu Pro Ala Asn Leu Asp Asp
        335                   340                   345 atg aag gtg gca gag ctg aag cag gag ctg aag ttg cga tca ctg cct    1645
Met Lys Val Ala Glu Leu Lys Gln Glu Leu Lys Leu Arg Ser Leu Pro
350                   355                   360                   365 gtc tcg ggc acc aaa act gag ctg att gag cgc ctt cga gcc tat caa    1693
Val Ser Gly Thr Lys Thr Glu Leu Ile Glu Arg Leu Arg Ala Tyr Gln
                 370                   375                   380 gac caa atc agc cct gtg cca gga gcc ccc aag gcc cct gcc gcc acc    1741
Asp Gln Ile Ser Pro Val Pro Gly Ala Pro Lys Ala Pro Ala Ala Thr
        385                   390                   395 tct atc ctg cac aag gct ggc gag gtg gtg gta gcc ttc cca gcg gcc    1789
Ser Ile Leu His Lys Ala Gly Glu Val Val Val Ala Phe Pro Ala Ala
        400                   405                   410 cgg ctg agc acg ggg cca gcc ctg gtg gca gca ggc ctg gct cca gct    1837
Arg Leu Ser Thr Gly Pro Ala Leu Val Ala Ala Gly Leu Ala Pro Ala
415                   420                   425 gag gtg gtg gtg gcc acg gtg gcc agc agt ggg gtg gtg aag ttt ggc    1885
Glu Val Val Val Ala Thr Val Ala Ser Ser Gly Val Val Lys Phe Gly
430                   435                   440                   445 agc acg ggc tcc acg ccc ccc gtg tct ccc acc ccc tcg gag cgc tca    1933
Ser Thr Gly Ser Thr Pro Pro Val Ser Pro Thr Pro Ser Glu Arg Ser
                 450                   455                   460 ctg ctc agc acg ggc gat gaa aac tcc acc ccc ggg gac acc ttt ggt    1981
Leu Leu Ser Thr Gly Asp Glu Asn Ser Thr Pro Gly Asp Thr Phe Gly
        465                   470                   475 gag atg gtg aca tca cct ctg acg cag ctg acc ctg cag gcc tcg cca    2029
Glu Met Val Thr Ser Pro Leu Thr Gln Leu Thr Leu Gln Ala Ser Pro
480                   485                   490 ctg cag atc ctc gtg aag gag gag ggc ccc cgg gcc ggg tcc tgt tgc    2077
Leu Gln Ile Leu Val Lys Glu Glu Gly Pro Arg Ala Gly Ser Cys Cys
495                   500                   505 ctg agc cct ggg ggg cgg gcg gag cta gag ggg cgc gac aag gac cag    2125
Leu Ser Pro Gly Gly Arg Ala Glu Leu Glu Gly Arg Asp Lys Asp Gln
510                   515                   520                   525 atg ctg cag gag aaa gac aag cag atc gag gcg ctg acg cgc atg ctc    2173
Met Leu Gln Glu Lys Asp Lys Gln Ile Glu Ala Leu Thr Arg Met Leu
                 530                   535                   540 cgg cag aag cag cag ctg gtg gag cgg ctc aag ctg cag ctg gag cag    2221
Arg Gln Lys Gln Gln Leu Val Glu Arg Leu Lys Leu Gln Leu Glu Gln
        545                   550                   555 gag aag cga gcc cag cag ccc gcc ccc gcc ccc gcc ccc ctc ggc acc    2269
Glu Lys Arg Ala Gln Gln Pro Ala Pro Ala Pro Ala Pro Leu Gly Thr
        560                   565                   570 ccc gtg aag cag gag aac agc ttc tcc agc tgc cag ctg agc cag cag    2317
Pro Val Lys Gln Glu Asn Ser Phe Ser Ser Cys Gln Leu Ser Gln Gln
575                   580                   585 ccc ctg ggc ccc gct cac cca ttc aac ccc agc ctg gcg gcc cca gcc    2365
```

```
                Pro Leu Gly Pro Ala His Pro Phe Asn Pro Ser Leu Ala Ala Pro Ala
                590                 595                 600                 605 acc aac cac ata gac cct tgt gct gtg gcc ccg ggg ccc ccg tcc gtg      2413
Thr Asn His Ile Asp Pro Cys Ala Val Ala Pro Gly Pro Pro Ser Val
            610                 615                 620 gtg gtg aag cag gaa gcc ttg cag cct gag ccc gag ccg gtc ccc gcc      2461
Val Val Lys Gln Glu Ala Leu Gln Pro Glu Pro Glu Pro Val Pro Ala
        625                 630                 635 ccc cag ttg ctt ctg ggg cct cag ggc ccc agc ctc atc aag ggg gtt      2509
Pro Gln Leu Leu Leu Gly Pro Gln Gly Pro Ser Leu Ile Lys Gly Val
        640                 645                 650 gca cct ccc acc ctc atc acc gac tcc aca ggg acc cac ctt gtc ctc      2557
Ala Pro Pro Thr Leu Ile Thr Asp Ser Thr Gly Thr His Leu Val Leu
    655                 660                 665 acc gtg acc aat aag aat gca gac agc cct ggc ctg tcc agt ggg agc      2605
Thr Val Thr Asn Lys Asn Ala Asp Ser Pro Gly Leu Ser Ser Gly Ser
670                 675                 680                 685 ccc cag cag ccc tcg tcc cag cct ggc tct cca gcg cct gcc ccc tct      2653
Pro Gln Gln Pro Ser Ser Gln Pro Gly Ser Pro Ala Pro Ala Pro Ser
                690                 695                 700 gcc cag atg gac ctg gag cac cca ctg cag ccc ctc ttt ggg acc ccc      2701
Ala Gln Met Asp Leu Glu His Pro Leu Gln Pro Leu Phe Gly Thr Pro
        705                 710                 715 act tct ctg ctg aag aag gaa cca cct ggc tat gag gaa gcc atg agc      2749
Thr Ser Leu Leu Lys Lys Glu Pro Pro Gly Tyr Glu Glu Ala Met Ser
        720                 725                 730 cag cag ccc aaa cag cag gaa aat ggt tcc tca agc cag cag atg gac      2797
Gln Gln Pro Lys Gln Gln Glu Asn Gly Ser Ser Ser Gln Gln Met Asp
735                 740                 745 gac ctg ttt gac att ctc att cag agc gga gaa att tca gca gat ttc      2845
Asp Leu Phe Asp Ile Leu Ile Gln Ser Gly Glu Ile Ser Ala Asp Phe
750                 755                 760                 765 aag gag ccg cca tcc ctg cca ggg aag gag aag cca tcc ccg aag aca      2893
Lys Glu Pro Pro Ser Leu Pro Gly Lys Glu Lys Pro Ser Pro Lys Thr
                770                 775                 780 gtc tgt ggg tcc ccc ctg gca gca cag cca tca cct tct gct gag ctc      2941
Val Cys Gly Ser Pro Leu Ala Ala Gln Pro Ser Pro Ser Ala Glu Leu
            785                 790                 795 ccc cag gct gcc cca cct cct cca ggc tca ccc tcc ctc cct gga cgc      2989
Pro Gln Ala Ala Pro Pro Pro Gly Ser Pro Ser Leu Pro Gly Arg
        800                 805                 810 ctg gag gac ttc ctg gag agc agc acg ggg ctg ccc ctg ctg acc agt      3037
Leu Glu Asp Phe Leu Glu Ser Ser Thr Gly Leu Pro Leu Leu Thr Ser
    815                 820                 825 ggg cat gac ggg cca gag ccc ctt tcc ctc att gac gac ctc cat agc      3085
Gly His Asp Gly Pro Glu Pro Leu Ser Leu Ile Asp Asp Leu His Ser
830                 835                 840                 845 cag atg ctg agc agc act gcc atc ctg gac cac ccc ccg tca ccc atg      3133
Gln Met Leu Ser Ser Thr Ala Ile Leu Asp His Pro Pro Ser Pro Met
            850                 855                 860 gac acc tcg gaa ttg cac ttt gtt cct gag ccc agc agc acc atg ggc      3181
Asp Thr Ser Glu Leu His Phe Val Pro Glu Pro Ser Ser Thr Met Gly
        865                 870                 875 ctg gac ctg gct gat ggc cac ctg gac agc atg gac tgg ctg gag ctg      3229
Leu Asp Leu Ala Asp Gly His Leu Asp Ser Met Asp Trp Leu Glu Leu
    880                 885                 890 tcg tca ggt ggt ccc gtg ctg agc cta gcc ccc ctc agc acc aca gcc      3277
Ser Ser Gly Gly Pro Val Leu Ser Leu Ala Pro Leu Ser Thr Thr Ala
895                 900                 905
```

-continued

```
ccc agc ctc ttc tcc aca gac ttc ctc gat ggc cat gat ttg cag ctg     3325
Pro Ser Leu Phe Ser Thr Asp Phe Leu Asp Gly His Asp Leu Gln Leu
910                 915                 920                 925 cac tgg gat tcc tgc ttg tag ctctctggct caagacgggg tggggaaggg        3376
His Trp Asp Ser Cys Leu
                930 gctgggagcc aggtactcc aatgcgtggc tctcctgcgt gattcggcct ctccacatgg    3436
ttgtgagtct tgacaatcac agcccctgct ttttcccttc cctgggaggc tagaacagag   3496
aagcccttac tcctggttca gtgccacgca gggcagagga gagcagctgt caagaagcag   3556
ccctggctct cacgctgggg ttttggacac acggtcaggg tcaggccat ttcagcttga    3616
cctccttttt tgaggtcagg gggcactgtc tgtctggcta caatttggct aaggtaggtg   3676
aagcctggcc aggcgggagg cttctcttct gacccaggc tgagacaggt taaggggtga    3736
atctccttcc tttctctccc tgctttgctg tgaagggaga aattagcctg ggcctctacc   3796
ccctattccc tgtgtctgcc aaccccagga tcccagggct ccctgccatt ttagtgtctt   3856
ggtgtagtgt aaccattag tggttggtgg caacaatttt atgtacaggt gtatatacct    3916
ctatattata tatcgacata catatatatt tttgggggg ggcggacagg agatgggtgc    3976
aactccctcc catcctactc tcacagaagg gcctggatgc aaggttaccc ttgagctgtg   4036
tgccacagtc tggtgcccag tctggcatgc agctacccag gcccacccat cacgtgtgat   4096
tgacatgtag gtaccctgcc acggcctatg ccccacctgc cctgcttcct ggctccttat   4156
cagtgccatg agggcagagg tgctacctgg ccttcctgcc aggagctctc cacccactca   4216
cattccgtcc ccgccgcctc actgcagcca gcgtggtcct aggacaggag gagcttcggg   4276
cccagcttca ccctgcggtg gggctgaggg gtggccatct cctgccctgg ggccactggc   4336
ttcacattct gggctgactc atagggagt aggggtggag tcaccaaaac cagtgctggg    4396
acaaagatgg ggaaggtgtg tgaactttt aaaataaaca caaaaacaca g             4447
```

<210> SEQ ID NO 14
<211> LENGTH: 931
<212> TYPE: PRT
<213> ORGANISM: Homo sapiens

<400> SEQUENCE: 14

```
Met Pro Pro Leu Lys Ser Pro Ala Ala Phe His Glu Gln Arg Arg Ser
1               5                   10                  15

Leu Glu Arg Ala Arg Thr Glu Asp Tyr Leu Lys Arg Lys Ile Arg Ser
            20                  25                  30

Arg Pro Glu Arg Ser Glu Leu Val Arg Met His Ile Leu Glu Glu Thr
        35                  40                  45

Ser Ala Glu Pro Ser Leu Gln Ala Lys Gln Leu Lys Leu Lys Arg Ala
    50                  55                  60

Arg Leu Ala Asp Asp Leu Asn Glu Lys Ile Ala Gln Arg Pro Gly Pro
65                  70                  75                  80

Met Glu Leu Val Glu Lys Asn Ile Leu Pro Val Glu Ser Ser Leu Lys
                85                  90                  95

Glu Ala Ile Ile Val Gly Gln Val Asn Tyr Pro Lys Val Ala Asp Ser
            100                 105                 110

Ser Ser Phe Asp Glu Asp Ser Ser Asp Ala Leu Ser Pro Glu Gln Pro
        115                 120                 125

Ala Ser His Glu Ser Gln Gly Ser Val Pro Ser Pro Leu Glu Ala Arg
    130                 135                 140
```

```
Val Ser Glu Pro Leu Leu Ser Ala Thr Ser Ala Ser Pro Thr Gln Val
145                 150                 155                 160

Val Ser Gln Leu Pro Met Gly Arg Asp Ser Arg Glu Met Leu Phe Leu
            165                 170                 175

Ala Glu Gln Pro Pro Leu Pro Pro Pro Leu Leu Pro Pro Ser Leu
        180                 185                 190

Thr Asn Gly Thr Thr Ile Pro Thr Ala Lys Ser Thr Pro Thr Leu Ile
        195                 200                 205

Lys Gln Ser Gln Pro Lys Ser Ala Ser Glu Lys Ser Gln Arg Ser Lys
        210                 215                 220

Lys Ala Lys Glu Leu Lys Pro Lys Val Lys Lys Leu Lys Tyr His Gln
225                 230                 235                 240

Tyr Ile Pro Pro Asp Gln Lys Gln Asp Arg Gly Ala Pro Pro Met Asp
                245                 250                 255

Ser Ser Tyr Ala Lys Ile Leu Gln Gln Gln Leu Phe Leu Gln Leu
            260                 265                 270

Gln Ile Leu Asn Gln Gln Gln Gln His His Asn Tyr Gln Ala Ile
        275                 280                 285

Leu Pro Ala Pro Pro Lys Ser Ala Gly Glu Ala Leu Gly Ser Ser Gly
    290                 295                 300

Thr Pro Pro Val Arg Ser Leu Ser Thr Thr Asn Ser Ser Ser Ser Ser
305                 310                 315                 320

Gly Ala Pro Gly Pro Cys Gly Leu Ala Arg Gln Asn Ser Thr Ser Leu
                325                 330                 335

Thr Gly Lys Pro Gly Ala Leu Pro Ala Asn Leu Asp Asp Met Lys Val
            340                 345                 350

Ala Glu Leu Lys Gln Glu Leu Lys Leu Arg Ser Leu Pro Val Ser Gly
            355                 360                 365

Thr Lys Thr Glu Leu Ile Glu Arg Leu Arg Ala Tyr Gln Asp Gln Ile
    370                 375                 380

Ser Pro Val Pro Gly Ala Pro Lys Ala Pro Ala Ala Thr Ser Ile Leu
385                 390                 395                 400

His Lys Ala Gly Glu Val Val Ala Phe Pro Ala Ala Arg Leu Ser
                405                 410                 415

Thr Gly Pro Ala Leu Val Ala Ala Gly Leu Ala Pro Ala Glu Val Val
            420                 425                 430

Val Ala Thr Val Ala Ser Ser Gly Val Val Lys Phe Gly Ser Thr Gly
            435                 440                 445

Ser Thr Pro Pro Val Ser Pro Thr Pro Ser Glu Arg Ser Leu Leu Ser
    450                 455                 460

Thr Gly Asp Glu Asn Ser Thr Pro Gly Asp Thr Phe Gly Glu Met Val
465                 470                 475                 480

Thr Ser Pro Leu Thr Gln Leu Thr Leu Gln Ala Ser Pro Leu Gln Ile
            485                 490                 495

Leu Val Lys Glu Glu Gly Pro Arg Ala Gly Ser Cys Cys Leu Ser Pro
        500                 505                 510

Gly Gly Arg Ala Glu Leu Glu Gly Arg Asp Lys Asp Gln Met Leu Gln
        515                 520                 525

Glu Lys Asp Lys Gln Ile Glu Ala Leu Thr Arg Met Leu Arg Gln Lys
        530                 535                 540

Gln Gln Leu Val Glu Arg Leu Lys Leu Gln Leu Glu Gln Glu Lys Arg
545                 550                 555                 560

Ala Gln Gln Pro Ala Pro Ala Pro Ala Pro Leu Gly Thr Pro Val Lys
```

```
                    565                 570                 575
Gln Glu Asn Ser Phe Ser Ser Cys Gln Leu Ser Gln Gln Pro Leu Gly
            580                 585                 590

Pro Ala His Pro Phe Asn Pro Ser Leu Ala Ala Pro Ala Thr Asn His
        595                 600                 605

Ile Asp Pro Cys Ala Val Ala Pro Gly Pro Ser Val Val Lys
    610                 615                 620

Gln Glu Ala Leu Gln Pro Glu Pro Val Pro Ala Pro Gln Leu
625                 630                 635                 640

Leu Leu Gly Pro Gln Gly Pro Ser Leu Ile Lys Gly Val Ala Pro Pro
                645                 650                 655

Thr Leu Ile Thr Asp Ser Thr Gly Thr His Leu Val Leu Thr Val Thr
            660                 665                 670

Asn Lys Asn Ala Asp Ser Pro Gly Leu Ser Ser Gly Ser Pro Gln Gln
            675                 680                 685

Pro Ser Gln Pro Gly Ser Pro Ala Pro Ala Pro Ser Ala Gln Met
    690                 695                 700

Asp Leu Glu His Pro Leu Gln Pro Leu Phe Gly Thr Pro Thr Ser Leu
705                 710                 715                 720

Leu Lys Lys Glu Pro Pro Gly Tyr Glu Glu Ala Met Ser Gln Gln Pro
                725                 730                 735

Lys Gln Gln Glu Asn Gly Ser Ser Gln Gln Met Asp Asp Leu Phe
            740                 745                 750

Asp Ile Leu Ile Gln Ser Gly Glu Ile Ser Ala Asp Phe Lys Glu Pro
            755                 760                 765

Pro Ser Leu Pro Gly Lys Glu Lys Pro Ser Pro Lys Thr Val Cys Gly
    770                 775                 780

Ser Pro Leu Ala Ala Gln Pro Ser Pro Ser Ala Glu Leu Pro Gln Ala
785                 790                 795                 800

Ala Pro Pro Pro Gly Ser Pro Ser Leu Pro Gly Arg Leu Glu Asp
                805                 810                 815

Phe Leu Glu Ser Ser Thr Gly Leu Pro Leu Leu Thr Ser Gly His Asp
            820                 825                 830

Gly Pro Glu Pro Leu Ser Leu Ile Asp Asp Leu His Ser Gln Met Leu
            835                 840                 845

Ser Ser Thr Ala Ile Leu Asp His Pro Pro Ser Pro Met Asp Thr Ser
850                 855                 860

Glu Leu His Phe Val Pro Glu Pro Ser Ser Thr Met Gly Leu Asp Leu
865                 870                 875                 880

Ala Asp Gly His Leu Asp Ser Met Asp Trp Leu Glu Leu Ser Ser Gly
                885                 890                 895

Gly Pro Val Leu Ser Leu Ala Pro Leu Ser Thr Thr Ala Pro Ser Leu
            900                 905                 910

Phe Ser Thr Asp Phe Leu Asp Gly His Asp Leu Gln Leu His Trp Asp
        915                 920                 925

Ser Cys Leu
    930

<210> SEQ ID NO 15
<211> LENGTH: 24
<212> TYPE: DNA
<213> ORGANISM: synthetic construct

<400> SEQUENCE: 15
```

-continued aggctggact caacaggaag gatg                                    24

<210> SEQ ID NO 16
<211> LENGTH: 23
<212> TYPE: DNA
<213> ORGANISM: synthetic construct

<400> SEQUENCE: 16
cctggcccgc tccaagctcc ttc                                     23

<210> SEQ ID NO 17
<211> LENGTH: 23
<212> TYPE: DNA
<213> ORGANISM: synthetic construct

<400> SEQUENCE: 17
ctgctcatga aatgcggctg gac                                     23

<210> SEQ ID NO 18
<211> LENGTH: 22
<212> TYPE: DNA
<213> ORGANISM: synthetic construct

<400> SEQUENCE: 18
tctcccagca gttcctggat tc                                      22

<210> SEQ ID NO 19
<211> LENGTH: 24
<212> TYPE: DNA
<213> ORGANISM: synthetic construct

<400> SEQUENCE: 19
ctggctctct tcagcttcag ctgc                                    24

<210> SEQ ID NO 20
<211> LENGTH: 22
<212> TYPE: DNA
<213> ORGANISM: synthetic construct

<400> SEQUENCE: 20
tctccttgca gcccgagctg ac                                      22

<210> SEQ ID NO 21
<211> LENGTH: 24
<212> TYPE: DNA
<213> ORGANISM: synthetic construct

<400> SEQUENCE: 21
ccatcagagg cccatgtaaa ctcc                                    24

<210> SEQ ID NO 22
<211> LENGTH: 24
<212> TYPE: DNA
<213> ORGANISM: synthetic construct

<400> SEQUENCE: 22
gttacacacg gactttagga cgca                                    24

<210> SEQ ID NO 23
<211> LENGTH: 23
<212> TYPE: DNA
<213> ORGANISM: synthetic construct

<400> SEQUENCE: 23

-continued

```
catgcttcta ctgaagaaca gca                                              23

<210> SEQ ID NO 24
<211> LENGTH: 21
<212> TYPE: DNA
<213> ORGANISM: synthetic construct

<400> SEQUENCE: 24
aatccaggaa ctgctgggag a                                                21

<210> SEQ ID NO 25
<211> LENGTH: 20
<212> TYPE: DNA
<213> ORGANISM: synthetic construct

<400> SEQUENCE: 25
actggttgaa cagcggatga                                                  20

<210> SEQ ID NO 26
<211> LENGTH: 20
<212> TYPE: DNA
<213> ORGANISM: synthetic construct

<400> SEQUENCE: 26
aactgtgagc gcacgtttga                                                  20

<210> SEQ ID NO 27
<211> LENGTH: 21
<212> TYPE: DNA
<213> ORGANISM: synthetic construct

<400> SEQUENCE: 27
gtcctaaagt ccgtgtgtaa c                                                21

<210> SEQ ID NO 28
<211> LENGTH: 21
<212> TYPE: DNA
<213> ORGANISM: synthetic construct

<400> SEQUENCE: 28
ggtcagtgga ctcctttctc c                                                21

<210> SEQ ID NO 29
<211> LENGTH: 22
<212> TYPE: DNA
<213> ORGANISM: synthetic construct

<400> SEQUENCE: 29
gctgttgcca atgaactgca gg                                               22
```